(12) United States Patent
Matsui et al.

(10) Patent No.: US 7,557,123 B2
(45) Date of Patent: Jul. 7, 2009

(54) HETEROCYCLIC COMPOUND AND MEDICINAL USE THEREOF

(75) Inventors: Hiroshi Matsui, Nara (JP); Hideo Kobayashi, Uji (JP); Satoru Azukizawa, Kyoto (JP); Masayasu Kasai, Kyoto (JP); Akihisa Yoshimi, Takatsuki (JP); Hiroaki Shirahase, Nagaokakyo (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 1059 days.

(21) Appl. No.: 10/478,862

(22) PCT Filed: May 27, 2002

(86) PCT No.: PCT/JP02/05097

§ 371 (c)(1), (2), (4) Date: Nov. 25, 2003

(87) PCT Pub. No.: WO02/096880

PCT Pub. Date: Dec. 5, 2002

(65) Prior Publication Data

US 2004/0220215 A1 Nov. 4, 2004

(30) Foreign Application Priority Data

May 29, 2001 (JP) .............................. 2001-161489

(51) Int. Cl.
A61K 31/47 (2006.01)
C07D 217/02 (2006.01)
C07D 401/02 (2006.01)

(52) U.S. Cl. ...................................... 514/307; 546/146
(58) Field of Classification Search ........................ None
See application file for complete search history.

(56) References Cited

U.S. PATENT DOCUMENTS

| | | | | |
|---|---|---|---|---|
| 4,572,912 A | 2/1986 | Yoshioka et al. | ............. | 514/369 |
| 4,687,777 A | 8/1987 | Meguro et al. | ............... | 514/342 |
| 5,002,953 A | 3/1991 | Hindley | ........................ | 514/275 |
| 6,872,732 B2 * | 3/2005 | Matsui et al. | ................ | 514/307 |

FOREIGN PATENT DOCUMENTS

| | | |
|---|---|---|
| WO | 93/23378 | 11/1993 |
| WO | 97/31907 | 9/1997 |
| WO | 98/00137 | 1/1998 |
| WO | 98/00403 | 1/1998 |
| WO | 00/08002 | 2/2000 |
| WO | 01/40192 | 6/2001 |
| WO | 02/12193 | 2/2002 |
| WO | 02/096904 | 12/2002 |

OTHER PUBLICATIONS

Database XP-002239188, Bioorganic & Medicinal Chemistry, vol. 4, No. 1, 1994, pp. 57-62.
Margaret M. Faul et al., "Synthesis of 2-Phenyloxazole Derivatives Containing Amino Acids as Insulin Sensitivity Enhancers for Treatment of Type II Diabetes", Heterocycles, Apr. 1, 2001, vol. 55, No. 4, pp. 689-704.

* cited by examiner

Primary Examiner—Zinna N Davis
(74) Attorney, Agent, or Firm—Wenderoth, Lind & Ponack, LLP.

(57) ABSTRACT

The novel heterocyclic compound of the present invention is a novel heterocyclic compound having the formula (I)

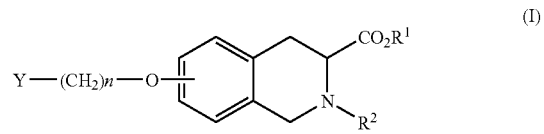

Y:

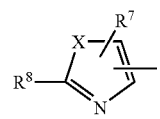

$R^{15}$—C($R^{14}$)=N—O—
wherein $R^1$ is H or $C_{1-6}$ alkyl, $R^2$ is H, —CO—C($R^4$)=C($R^4$)—$R^5$ wherein $R^4$ is H or $C_{1-4}$ alkyl, and $R^5$ is $C_{4-8}$ alkyl, $C_{2-8}$ alkenyl and the like, and the like, Y is the following group wherein X is O or S, $R^7$ is the same as $R^4$, $R^8$ is $R^{10}$—C($R^9$)=C($R^9$)— wherein $R^9$ is the same as $R^4$, $R^{10}$ is $C_{3-6}$ alkyl and the like, and the like, $R^{14}$ is the same as $R^4$, and $R^{15}$ is aryl and the like, Y—($CH_2$)n-O— is bonded to the 6- or 7-position of the tetrahydroisoquinoline skeleton, and n is an integer of 1 to 4, or a pharmaceutically acceptable salt thereof. The compound (I) of the present invention is useful as a hypoglycemic agent, a hypolipidemic agent, an insulin resistance improver, a therapeutic agent of diabetes, a therapeutic agent of diabetic complications, a glucose tolerance improver, an anti-arteriosclerosis agent, an anti-obesity agent, an antiinflammatory agent, an agent for the prophylaxis or treatment of PPAR-mediated diseases or an agent for the prophylaxis or treatment of syndrome X.

27 Claims, No Drawings

HETEROCYCLIC COMPOUND AND MEDICINAL USE THEREOF

This application is a U.S. National Stage of International Application No. PCT/JP02/05097, filed May 27, 2002.

TECHNICAL FIELD OF THE INVENTION

The present invention relates to a novel heterocyclic compound and a pharmaceutically acceptable salt thereof, which have a hypoglycemic action, a blood hypolipidemic action, an insulin resistance-improving action and a PPAR (peroxisome proliferator-activated receptor)-activating action. The present invention also relates to a pharmaceutical composition comprising the above-mentioned novel heterocyclic compound or a pharmaceutically acceptable salt thereof. Furthermore, the present invention relates to a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X, all of which comprising the above-mentioned novel heterocyclic compound or a pharmaceutically acceptable salt thereof.

BACKGROUND OF THE INVENTION

As a therapeutic agent of diabetes, biguanide compounds having, as a main action, an inhibitory action on glucose absorption via the intestinal tract and on glucose release from the liver, sulfonylurea compounds having an accelerating action on insulin secretion as a main action, insulin and the like. have been employed. However, biguanide compounds cause lactic acidosis, and sulfonylurea compounds sometimes cause serious hypoglycemia due to their strong hypoglycemic action. Therefore, a due care should be given when in use of these compounds. In recent years, there have been active researches and developments of a therapeutic agent of diabetes, which is free of these defects, with the consequence that various compounds having an insulin resistance-improving action have been found.

The insulin resistance plays an important role as a cause of non-insulin dependent diabetes mellitus (NIDDM), along with decrease in the insulin secretion. As an agent that improves insulin resistance, various thiazolidine compounds are known. Examples of such compound include 5-[4-[(6-hydroxy-2,5,7,8-tetramethylchroman-2-yl)methoxy]benzyl]-2,4-thiazolidinedione (general name: troglitazone) is described in U.S. Pat. No. 4,572,912 and EP0139421B1, 5-[[4-[2-(5-ethyl-pyridin-2-yl)ethoxy]phenyl]-methyl]-2,4-thiazolidinedione (general name: pioglitazone) is described in U.S. Pat. No. 4,687,777 and EP0193256B1, and 5-[[4-[2-[N-methyl-N-(pyridin-2-yl)amino]ethoxy]phenyl]methyl]-2,4-thiazolidinedione (general name: rosiglitazone) is described in U.S. Pat. No. 5,002,953 and EP0306228B1. However, these pharmaceutical agents that improve insulin resistance may cause side effects such as hepatopathy, retention of fluid, edema, megalocardia, obesity and the like. Thus, the development of a highly safe insulin resistance improver effective for NIDDM has been desired.

SUMMARY OF THE INVENTION

It is therefore an object of the present invention to provide a compound having a hypoglycemic action, a blood hypolipidemic action, an insulin resistance-improving action and a PPAR activating action, which has a structure completely different from that of conventional compounds and which is highly safe, thereby to increase the diversity in and to broaden the range of selection from hypoglycemic agents, hypolipidemic agents, insulin resistance improvers, therapeutic agents of diabetes, therapeutic agents of diabetic complications, glucose intolerance improvers, anti-arteriosclerosis agents, anti-obesity agents, antiinflammatory agents, agents for the prophylaxis or treatment of PPAR-mediated diseases and agents for the prophylaxis or treatment of syndrome X.

The present inventors have conducted intensive studies in an attempt to solve the above-mentioned problems and found that a novel heterocyclic compound of the formula (I)

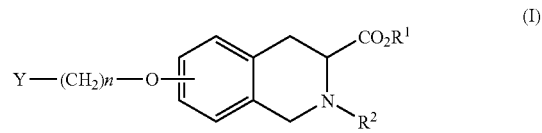

wherein $R^1$ is a hydrogen atom or $C_{1-6}$ alkyl;

$R^2$ is a hydrogen atom, —CO—$R^3$ wherein $R^3$ is $C_{2-6}$ alkyl optionally substituted by halogen, —CO—C($R^4$)=C($R^4$)—$R^5$ wherein $R^4$ is optionally the same as the other $R^4$ and is a hydrogen atom or $C_{1-4}$ alkyl, and $R^5$ is $C_{1-8}$ alkyl, $C_{2-8}$ alkenyl, aryl or aromatic heterocycle, —CO—C≡C—$R^6$ wherein $R^6$ is $C_{1-8}$ alkyl,

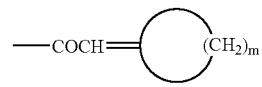

wherein m is an integer of 2 to 7, aryl, optionally substituted aryl $C_{1-3}$ alkyl, $C_{1-6}$ alkyl optionally substituted by halogen, $C_{2-6}$ alkenyl, $C_{3-8}$ cycloalkyl or $C_{3-8}$ cycloalkyl $C_{1-3}$ alkyl;

Y is

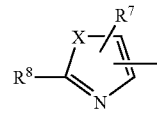

wherein $R^7$ is a hydrogen atom or $C_{1-4}$ alkyl, $R^8$ is $C_{5-8}$ alkyl, $C_{4-8}$ cycloalkyl, $C_{1-4}$ alkylthio $C_{1-6}$ alkyl, $R^{10}$—C($R^9$)=C($R^9$)— wherein $R^9$ is optionally the same as the other $R^9$ and is a hydrogen atom or $C_{1-4}$ alkyl and $R^{10}$ is $C_{1-6}$ alkyl optionally substituted by halogen, $C_{2-8}$ alkenyl, aryl, an aromatic heterocyclic, $C_{3-8}$ cycloalkyl, $C_{3-8}$ cycloalkyl $C_{1-3}$ alkyl, $C_{1-4}$ alkoxy $C_{1-6}$ alkyl, $C_{1-4}$ alkylthio $C_{1-6}$ alkyl or $C_{1-6}$ alkyl substituted by ($R^9$)$_2$N— wherein $R^9$ is optionally the same as the other $R^9$ and is a hydrogen atom or $C_{1-4}$ alkyl, $R^3$, —CO—N($R^{11}$)— wherein $R^{11}$ is a hydrogen atom or $C_{1-4}$ alkyl and $R^{12}$ is $C_{1-6}$ alkyl or aryl, $R^{13}$-Z- wherein $R^{13}$ is $C_{1-8}$ alkyl or aryl and Z is an oxygen atom or a sulfur atom, or

wherein k is an integer of 2 to 7 and X is an oxygen atom or a sulfur atom, or
$R^{15}$—C($R^{14}$)=N—O— wherein $R^{14}$ is a hydrogen atom or $C_{1-4}$ alkyl and $R^{15}$ is aryl or an aromatic heterocycle;
Y—$(CH_2)_n$—O— is bonded to the 6- or 7-position of a tetrahydroisoquinoline skeleton; and
n is an integer of 1 to 4 and a pharmaceutically acceptable salt thereof have a hypoglycemic action, a blood hypolipidemic action, an insulin resistance-improving action and a PPAR activating action, as well as high safety.

Accordingly, the present invention provides the following.

[1] A novel heterocyclic compound of the formula (I)

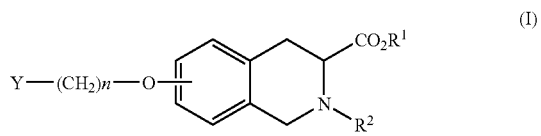

wherein
$R^1$ is a hydrogen atom or $C_{1-6}$ alkyl;
$R^2$ is a hydrogen atom, —CO—$R^3$ wherein $R^3$ is $C_{2-6}$ alkyl optionally substituted by halogen, —CO—C($R^4$)=C($R^4$)—$R^5$ wherein $R^4$ is optionally the same as the other $R^4$ and is a hydrogen atom or $C_{1-4}$ alkyl, and $R^5$ is $C_{1-8}$ alkyl, $C_{2-8}$ alkenyl, aryl or an aromatic heterocycle, —CO—C≡C—$R^6$ wherein $R^6$ is $C_{1-8}$ alkyl,

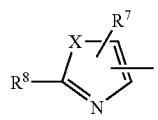

wherein m is an integer of 2 to 7, aryl, optionally substituted aryl $C_{1-3}$ alkyl, $C_{1-6}$ alkyl optionally substituted by halogen, $C_{2-6}$ alkenyl, $C_{3-8}$ cycloalkyl or $C_{3-8}$ cycloalkyl $C_{1-3}$ alkyl;
Y is

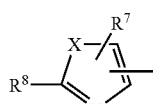

wherein $R^7$ is a hydrogen atom or $C_{1-4}$ alkyl, $R^8$ is $C_{5-8}$ alkyl, $C_{4-8}$ cycloalkyl, $C_{1-4}$ alkylthio $C_{1-6}$ alkyl, $R^{10}$—C($R^9$)=C($R^9$)— wherein $R^9$ is optionally the same as the other $R^9$ and is a hydrogen atom, or $C_{1-4}$ alkyl and $R^{10}$ is $C_{1-6}$ alkyl optionally substituted by halogen, $C_{2-8}$ alkenyl, aryl, an aromatic heterocycle, $C_{3-8}$ cycloalkyl, $C_{3-8}$ cycloalkyl $C_{1-3}$ alkyl, $C_{1-4}$ alkoxy $C_{1-6}$ alkyl, $C_{1-4}$ alkylthio $C_{1-6}$ alkyl or $C_{1-6}$ alkyl substituted by ($R^9$)$_2$N— wherein $R^9$ is optionally the same as the other $R^9$ and is a hydrogen atom or $C_{1-4}$ alkyl, $R^{12}$—CO—N($R^{11}$)— wherein $R^{11}$ is a hydrogen atom or $C_{1-4}$ alkyl and $R^{12}$ is $C_{1-6}$ alkyl or aryl, $R^{13}$-Z- wherein $R^{13}$ is $C_{1-8}$ alkyl or aryl and Z is an oxygen atom or a sulfur atom, or

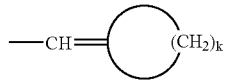

wherein k is an integer of 2 to 7 and X is an oxygen atom or a sulfur atom, or $R^{15}$—C($R^{14}$)=N—O— wherein $R^{14}$ is a hydrogen atom or $C_{1-4}$ alkyl and $R^{15}$ is aryl or an aromatic heterocycle;
Y—$(CH_2)_n$—O— is bonded to the 6- or 7-position of a tetrahydroisoquinoline skeleton; and
n is an integer of 1 to 4, or a pharmaceutically acceptable salt thereof.

[2] The novel heterocyclic compound of [1] above, wherein, in the formula (I), $R^2$ is an optionally substituted aryl $C_{1-3}$ alkyl, $C_{1-6}$ alkyl optionally substituted by halogen, $C_{2-6}$ alkenyl, $C_{3-8}$ cycloalkyl, $C_{3-8}$ cycloalkyl $C_{1-3}$ alkyl or

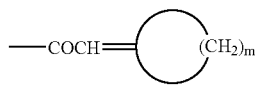

wherein m is an integer of 2 to 7, or a pharmaceutically acceptable salt thereof.

[3] The novel heterocyclic compound of [1] above, wherein, in the formula (I), Y is

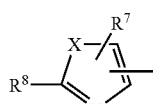

wherein $R^7$ is a hydrogen atom or $C_{1-4}$ alkyl, $R^8$ is $C_{1-4}$ alkylthio $C_{1-6}$ alkyl, $R^{10}$—C($R^9$)=C($R^9$)— wherein $R^9$ is optionally the same as the other $R^9$ and is a hydrogen atom or $C_{1-4}$ alkyl, $R^{10}$ is $C_{1-6}$ alkyl optionally substituted by halogen, $C_{3-8}$ cycloalkyl, $C_{3-8}$ cycloalkyl $C_{1-3}$ alkyl, $C_{1-4}$ alkoxy $C_{1-6}$ alkyl, $C_{1-4}$ alkylthio $C_{1-6}$ alkyl, $C_{1-6}$ alkyl substituted by ($R^9$)$_2$N— wherein $R^9$ is optionally the same as the other $R^9$ and is a hydrogen atom or $C_{1-4}$ alkyl, or

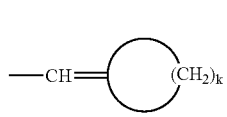

wherein k is an integer of 2 to 7, and X is an oxygen atom or a sulfur atom, or a pharmaceutically acceptable salt thereof.

[4] The novel heterocyclic compound of [1] above, wherein, in the formula (I), $R^2$ is a hydrogen atom, —CO—$R^3$ wherein $R^3$ is $C_{2-6}$ alkyl optionally substituted by halogen, —COC $(R^4)=C(R^4)$—$R^5$ wherein $R^4$ is optionally the same as the other $R^4$ and is a hydrogen atom or $C_{1-4}$ alkyl and $R^5$ is $C_{1-8}$ alkyl, $C_{2-8}$ alkenyl, aryl or aromatic heterocycle, —CO—C≡C—$R^6$ wherein $R^6$ is $C_{1-8}$ alkyl, or aryl, Y is

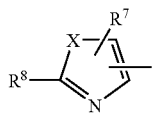

wherein $R^7$ is a hydrogen atom or $C_{1-4}$ alkyl, $R^8$ is $C_{5-8}$ alkyl, $C_{4-8}$ cycloalkyl, $R^{10}$—$C(R^9)=C(R^9)$— wherein $R^9$ is optionally the same as the other $R^9$ and is a hydrogen atom or $C_{1-4}$ alkyl, $R^{10}$ is $C_{1-6}$ alkyl, $C_{2-8}$ alkenyl, aryl or aromatic heterocycle, $R^{12}$—CO—N($R^{11}$)— wherein $R^{11}$ is a hydrogen atom or $C_{1-4}$ alkyl, and $R^{12}$ is $C_{1-6}$ alkyl or aryl, or $R^{13}$-Z- wherein $R^{13}$ is $C_{1-8}$ alkyl or aryl and Z is an oxygen atom or a sulfur atom, and X is an oxygen atom or a sulfur atom, or $R^{15}$—C($R^{14}$)=N—O— wherein $R^{14}$ is a hydrogen atom or $C_{1-4}$ alkyl and $R^{15}$ is aryl or aromatic heterocycle, or a pharmaceutically acceptable salt thereof.

[5] The novel heterocyclic compound of [2] or [3] above, wherein, in the formula (I), Y—(CH$_2$)n-O— is bonded to the 7-position of a tetrahydroisoquinoline skeleton and n is 2, or a pharmaceutically acceptable salt thereof.

[6] The novel heterocyclic compound of [4] above, wherein, in the formula (I), Y—(CH$_2$)n-O— is bonded to the 7-position of a tetrahydroisoquinoline skeleton and n is 2, or a pharmaceutically acceptable salt thereof.

[7] The novel heterocyclic compound of [6] above, wherein, in the formula (I), Y is

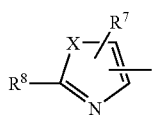

wherein $R^7$ is a hydrogen atom or $C_{1-4}$ alkyl, $R^8$ is $R^{10}$—C($R^9$)=C($R^9$)— wherein $R^9$ is optionally the same as the other $R^9$ and is a hydrogen atom or $C_{1-4}$ alkyl, and $R^{10}$ is $C_{1-6}$ alkyl, $C_{2-8}$ alkenyl or aryl, or a pharmaceutically acceptable salt thereof.

[8] The novel heterocyclic compound of [6] above, wherein, in the formula (I), Y is

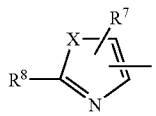

wherein $R^7$ is a hydrogen atom or $C_{1-4}$ alkyl, $R^8$ is $R^{13}$-Z- wherein $R^{13}$ is $C_{1-8}$ alkyl or aryl, and Z is a sulfur atom, or a pharmaceutically acceptable salt thereof.

[9] The novel heterocyclic compound of [6] above, wherein, in the formula (I), Y is

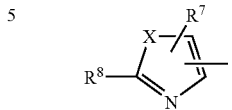

wherein $R^7$ is a hydrogen atom or $C_{1-4}$ alkyl and $R^8$ is $C_{5-8}$ alkyl or $C_{4-8}$ cycloalkyl, or a pharmaceutically acceptable salt thereof.

[10] The novel heterocyclic compound of [5] above, wherein, in the formula (I), Y is

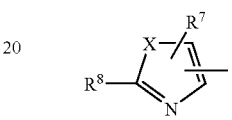

wherein $R^7$ is a hydrogen atom or $C_{1-4}$ alkyl and $R^8$ is $R^{10}$—C($R^9$)=C($R^9$)— wherein $R^9$ is optionally the same as the other $R^9$ and is a hydrogen atom or $C_{1-4}$ alkyl and $R^{10}$ is $C_{3-8}$ cycloalkyl, or a pharmaceutically acceptable salt thereof.

[11] The novel heterocyclic compound of any of [7] to [10] above, wherein, in the formula (I), $R^2$ is —CO—C($R^4$)=C($R^4$)—$R^5$ wherein $R^4$ is a hydrogen atom and $R^5$ is $C_{1-8}$ alkyl or $C_{2-8}$ alkenyl, or a pharmaceutically acceptable salt thereof.

[12] The novel heterocyclic compound of any of [7] to [10] above, wherein, in the formula (I), $R^2$ is —CO—C≡C—$R^6$ wherein $R^6$ is $C_{1-8}$ alkyl, or a pharmaceutically acceptable salt thereof.

[13] The novel heterocyclic compound of [6] above, wherein, in the formula (I), Y is

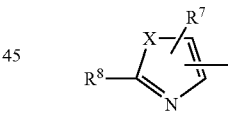

wherein $R^7$ is $C_{1-4}$ alkyl, $R^8$ is $R^{10}$—C($R^9$)=C($R^9$)— wherein $R^9$ is optionally the same as the other $R^9$ and is a hydrogen atom or $C_{1-4}$ alkyl and $R^{10}$ is $C_{1-6}$ alkyl, and X is an oxygen atom, or a pharmaceutically acceptable salt thereof.

[14] The novel heterocyclic compound of [6] above, wherein, in the formula (I), Y is

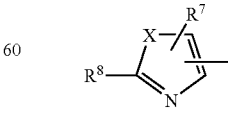

wherein $R^7$ is $C_{1-4}$ alkyl, $R^8$ is $R^{10}$—C($R^9$)=C($R^9$)— wherein $R^9$ is a hydrogen atom and $R^{10}$ is aryl, and X is an oxygen atom, or a pharmaceutically acceptable salt thereof.

[15] The novel heterocyclic compound of [4] or [5] above, wherein, in the formula (I), Y is selected from the following (a) to (n):

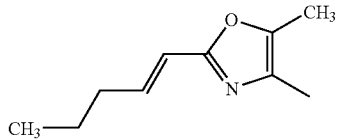 (a)

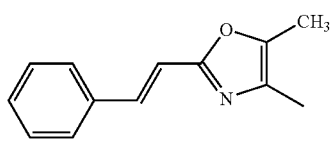 (b)

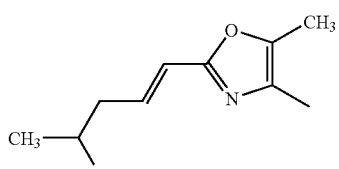 (c)

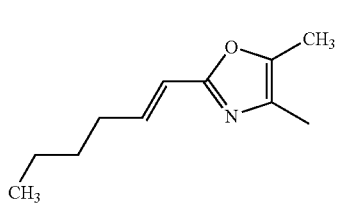 (d)

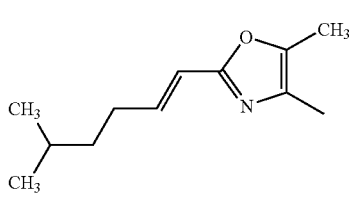 (e)

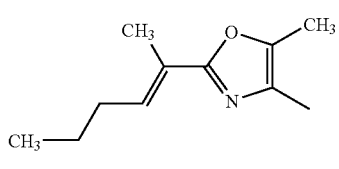 (f)

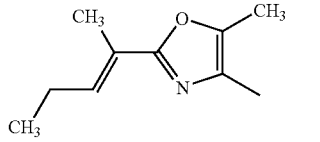 (g)

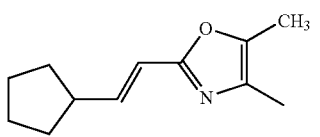 (h)

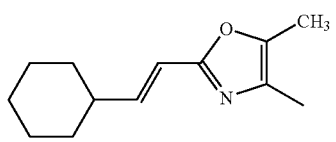 (i)

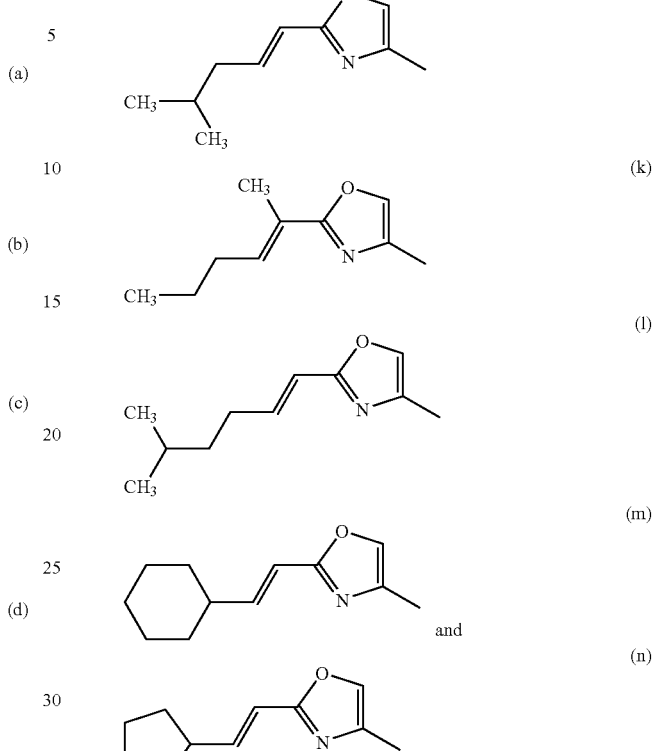

or a pharmaceutically acceptable salt thereof.

[16] The novel heterocyclic compound of [1] above, wherein the compound of the formula (I) is any of the following (1) to (16):

(1) 2-(2,4-hexadienoyl)-7-[2-(5-methyl-2-styryloxazol-4-yl)ethoxy]-1,2,3,4-tetrahydroisoquinoline-(3S)-carboxylic acid, (2) 2-(2-heptenoyl)-7-[2-(5-methyl-2-styryloxazol-4-yl)ethoxy]-1,2,3,4-tetrahydroisoquinoline-(3S)-carboxylic acid, (3) 2-(2-hexynoyl)-7-[2-(5-methyl-2-styryloxazol-4-yl)ethoxy]-1,2,3,4-tetrahydroisoquinoline-(3S)-carboxylic acid, (4) 7-[2-(5-methyl-2-styryloxazol-4-yl)ethoxy]-2-pentafluoropropionyl-1,2,3,4-tetrahydroisoquinoline-(3S)-carboxylic acid, (5) 2-(2-heptenoyl)-7-[2-(5-methyl-2-styrylthiazol-4-yl)ethoxy]-1,2,3,4-tetrahydroisoquinoline-(3S)-carboxylic acid, (6) 2-(2,4-hexadienoyl)-7-[2-(5-methyl-2-(1-penten-1-yl)oxazol-4-yl)ethoxy]-1,2,3,4-tetrahydroisoquinoline-(3S)-carboxylic acid, (7) 2-(2-heptenoyl)-7-[2-(5-methyl-2-(1-penten-1-yl)oxazol-4-yl)ethoxy]-1,2,3,4-tetrahydroisoquinoline-(3S)-carboxylic acid, (8) 2-(2-hexynoyl)-7-[2-(5-methyl-2-(1-penten-1-yl)oxazol-4-yl)ethoxy]-1,2,3,4-tetrahydroisoquinoline-(3S)-carboxylic acid, (9) 2-(2,4-hexadienoyl)-7-[2-(5-methyl-2-(1,3-pentadien-1-yl)oxazol-4-yl)ethoxy]-1,2,3,4-tetrahydroisoquinoline-(3S)-carboxylic acid,

(10) 2-(2,4-hexadienoyl)-7-[2-(5-methyl-2-pentyloxazol-4-yl)ethoxy]-1,2,3,4-tetrahydroisoquinoline-(3S)-carboxylic acid,
(11) 7-[2-(2-cyclopentyl-5-methyloxazol-4-yl)ethoxy]-2-(2,4-hexadienoyl)-1,2,3,4-tetrahydroisoquinoline-(3S)-carboxylic acid,
(12) 7-[2-(2-cyclohexyl-5-methyloxazol-4-yl)ethoxy]-2-(2,4-hexadienoyl)-1,2,3,4-tetrahydroisoquinoline-(3S)-carboxylic acid,
(13) 7-[2-(2-benzoylaminothiazol-5-yl)ethoxy]-2-(2-heptenoyl)-1,2,3,4-tetrahydroisoquinoline-(3S)-carboxylic acid,
(14) 7-[2-(2-butyrylaminothiazol-5-yl)ethoxy]-2-(2-heptenoyl)-1,2,3,4-tetrahydroisoquinoline-(3S)-carboxylic acid,
(15) 2-(2-heptenoyl)-7-[2-(4-methyl-2-phenylsulfanylthiazol-5-yl)ethoxy]-1,2,3,4-tetrahydroisoquinoline-(3S)-carboxylic acid, and
(16) 2-(2-heptenoyl)-7-[2-(1-phenylethylideneaminoxy)ethoxy]-1,2,3,4-tetrahydroisoquinoline-(3S)-carboxylic acid, or a pharmaceutically acceptable salt thereof.

[17] The novel heterocyclic compound of [1] above, wherein the compound of the formula (I) is any of the following (1) to (3):
(1) 7-[2-(5-methyl-2-styryloxazol-4-yl)ethoxy]-2-pentafluoropropionyl-1,2,3,4-tetrahydroisoquinoline-(3S)-carboxylic acid,
(2) 2-(2-heptenoyl)-7-[2-(5-methyl-2-(trans-1-penten-1-yl)oxazol-4-yl)ethoxy]-1,2,3,4-tetrahydroisoquinoline-(3S)-carboxylic acid, and
(3) 2-(2-hexynoyl)-7-[2-(5-methyl-2-(trans-1-penten-1-yl)oxazol-4-yl)ethoxy]-1,2,3,4-tetrahydroisoquinoline-(3S)-carboxylic acid, or a pharmaceutically acceptable salt thereof.

[18] The novel heterocyclic compound of [1] above, wherein the compound of the formula (I) is any of the following (1) to (17):
(1) 2-(2,4-hexadienoyl)-7-{2-[5-methyl-2-(4-methyl-1-penten-1-yl)oxazol-4-yl]ethoxy}-1,2,3,4-tetrahydroisoquinoline-(3S)-carboxylic acid,
(2) 2-(2-heptenoyl)-7-{2-[5-methyl-2-(4-methyl-1-penten-1-yl)oxazol-4-yl]ethoxy}-1,2,3,4-tetrahydroisoquinoline-(3S)-carboxylic acid,
(3) 2-(2,4-hexadienoyl)-7-{2-[2-(1-hexen-1-yl)-5-methyloxazol-4-yl]ethoxy}-1,2,3,4-tetrahydroisoquinoline-(3S)-carboxylic acid,
(4) 2-(2,4-hexadienoyl)-7-{2-[5-methyl-2-(5-methyl-1-hexen-1-yl)oxazol-4-yl]ethoxy}-1,2,3,4-tetrahydroisoquinoline-(3S)-carboxylic acid,
(5) 2-(2,4-hexadienoyl)-7-{2-[5-methyl-2-(1-methyl-1-penten-1-yl)oxazol-4-yl]ethoxy}-1,2,3,4-tetrahydroisoquinoline-(3S)-carboxylic acid,
(6) 2-(2,4-hexadienoyl)-7-{2-[5-methyl-2-(1-methyl-1-buten-1-yl)oxazol-4-yl]ethoxy}-1,2,3,4-tetrahydroisoquinoline-(3S)-carboxylic acid,
(7) 2-(2-hexenoyl)-7-{2-[5-methyl-2-(4-methyl-1-penten-1-yl)oxazol-4-yl]ethoxy}-1,2,3,4-tetrahydroisoquinoline-(3S)-carboxylic acid,
(8) 7-{2-[5-methyl-2-(1-penten-1-yl)oxazol-4-yl]ethoxy}-2-(2,2,3,3,3-pentafluoropropionyl)-1,2,3,4-tetrahydroisoquinoline-(3S)-carboxylic acid,
(9) 7-{2-[2-(4,4-dimethyl-1-penten-1-yl)-5-methyloxazol-4-yl]ethoxy}-2-(2,4-hexadienoyl)-1,2,3,4-tetrahydroisoquinoline-(3S)-carboxylic acid,
(10) 2-(2,4-hexadienoyl)-7-{2-[5-methyl-2-(3-methyl-1-buten-1-yl)oxazol-4-yl]ethoxy}-1,2,3,4-tetrahydroisoquinoline-(3S)-carboxylic acid,
(11) 2-(2,4-hexadienoyl)-7-(2-{5-methyl-2-[2-(1-methylcyclohexan-1-yl)vinyl]oxazol-4-yl}ethoxy)-1,2,3,4-tetrahydroisoquinoline-3S)-carboxylic acid,
(12) 7-{2-[2-(3,3-dimethyl-1-buten-1-yl)-5-methyloxazol-4-yl]ethoxy}-2-(2,4-hexadienoyl)-1,2,3,4-tetrahydroisoquinoline-(3S)-carboxylic acid,
(13) 2-(2,4-hexadienoyl)-7-{2-[2-(3-methoxy-1-propen-1-yl)-5-methyloxazol-4-yl]ethoxy}-1,2,3,4-tetrahydroisoquinoline-(3S)-carboxylic acid,
(14) 7-{2-[2-(2-cyclopentylvinyl)-5-methyloxazol-4-yl]ethoxy}-2-(2,4-hexadienoyl)-1,2,3,4-tetrahydroisoquinoline-(3S)-carboxylic acid,
(15) 7-{2-[2-(2-cyclohexylvinyl)-5-methyloxazol-4-yl]ethoxy}-2-(2,4-hexadienoyl)-1,2,3,4-tetrahydroisoquinoline-(3S)-carboxylic acid,
(16) 2-(3-butenyl)-7-{2-[5-methyl-2-(4-methyl-1-penten-1-yl)oxazol-4-yl]ethoxcy}-1,2,3,4-tetrahydroisoquinoline-(3S)-carboxylic acid, and
(17) 7-{2-[5-methyl-2-(4-methyl-1-penten-1-yl)oxazol-4-yl]ethoxy}-2-(4-pentenyl)-1,2,3,4-tetrahydroisoquinoline-(3S)-carboxylic acid, or a pharmaceutically acceptable salt thereof.

[19] The novel heterocyclic compound of [1] above, wherein the compound of the formula (I) is any of the following (1) to (8):
(1) 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic acid,
(2) 2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic acid,
(3) 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid,
(4) 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylic acid,
(5) 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid,
(6) 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylic acid,
(7) 2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylic acid, and
(8) 2-(2-hexenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, or a pharmaceutically acceptable salt thereof.

[20] The novel heterocyclic compound of [1] above, wherein the compound of the formula (I) is any of the following (1) to (6):
(1) 7-{2-[5-methyl-2-(trans-1-penten-1-yl)oxazol-4-yl]ethoxy}-2-(2,2,3,3,3-pentafluoropropionyl)-1,2,3,4-tetrahydroisoquinoline-(3S)-carboxylic acid,
(2) 7-{2-[2-(4,4-dimethyl-trans-1-penten-1-yl)-5-methyloxazol-4-yl]ethoxy}-2-(2,4-hexadienoyl)-1,2,3,4-tetrahydroisoquinoline-(3S)-carboxylic acid,
(3) 2-(2,4-hexadienoyl)-7-(2-[5-methyl-2-(3-methyl-trans-1-buten-1-yl)oxazol-4-yl]ethoxy}-1,2,3,4-tetrahydroisoquinoline-(3S)-carboxylic acid, (4) 2-(2,4-hexadienoyl)-7-(2-{5-methyl-2-[2-trans-(1-methylcyclohexan-1-yl)vinyl]oxazol-4-yl}ethoxy)-1,2,3,4-tetrahydroisoquinoline-(3S)-carboxylic acid,
(5) 7-{2-[2-(3,3-dimethyl-trans-1-buten-1-yl)-5-methyloxazol-4-yl]ethoxy}-2-(2,4-hexadienoyl)-1,2,3,4-tetrahydroisoquinoline-(3S)-carboxylic acid, and
(6) 2-(2,4-hexadienoyl)-7-{2-[2-(3-methoxy-trans-1-propen-1-yl)-5-methyloxazol-4-yl]ethoxy}-1,2,3,4-tetrahydroisoquinoline-(3S)-carboxylic acid, or a pharmaceutically acceptable salt thereof.

[21] The novel heterocyclic compound of [1] above, wherein the compound of the formula (I) is the following (1) or (2):
(1) 7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylic acid,
(2) 7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylic acid, or a pharmaceutically acceptable salt thereof.

[22] The novel heterocyclic compound of [1] above, wherein the compound of the formula (I) is the following (1) or (2):
(1) 2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic acid,
(2) 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid, or a pharmaceutically acceptable salt thereof.

[23] The novel heterocyclic compound of [1] above, wherein the compound of the formula (I) is any of the following (1) to (9):
(1) 2-(2,4-hexadienoyl)-7-{2-[2-(4-methyl-trans-1-penten-1-yl)oxazol-4-yl]ethoxy}-1,2,3,4-tetrahydroisoquinoline-(3S)-carboxylic acid,
(2) 7-(2-[2-(trans-2-cyclopentylvinyl)oxazol-4-yl]ethoxy)-2-(2,4-hexadienoyl)-1,2,3,4-tetrahydroisoquinoline-(3S)-carboxylic acid,
(3) 7-{2-[2-(trans-2-cyclohexylvinyl)oxazol-4-yl]ethoxy}-2-(2,4-hexadienoyl)-1,2,3,4-tetrahydroisoquinoline-(3S)-carboxylic acid,
(4) 2-(2-heptenoyl)-7-{2-[2-(4-methyl-trans-1-penten-1-yl)oxazol-4-yl]ethoxy}-1,2,3,4-tetrahydroisoquinoline-(3S)-carboxylic acid,
(5) 2-(2-hexenoyl)-7-{2-[2-(4-methyl-trans-1-penten-1-yl)oxazol-4-yl]ethoxy}-1,2,3,4-tetrahydroisoquinoline-(3S)-carboxylic acid,
(6) 2-(2,4-hexadienoyl)-7-{2-[2-(trans-1-hexen-1-yl)oxazol-4-yl]ethoxy}-1,2,3,4-tetrahydroisoquinoline-(3S)-carboxylic acid,
(7) 2-(2,4-hexadienoyl)-7-{2-[2-(1-methyl-trans-1-penten-1-yl)oxazol-4-yl]ethoxy}-1,2,3,4-tetrahydroisoquinoline-(3S)-carboxylic acid,
(8) 2-(2,4-hexadienoyl)-7-{2-[2-(1-methyl-trans-1-buten-1-yl)oxazol-4-yl]ethoxy}-1,2,3,4-tetrahydroisoquinoline-(3S)-carboxylic acid and
(9) 2-(2,4-hexadienoyl)-7-{2-[(5-methyl-trans-1-hexen-1-yl)oxazol-4-yl]ethoxy}-1,2,3,4-tetrahydroisoquinoline-(3S)-carboxylic acid, or a pharmaceutically acceptable salt thereof.

[24] A pharmaceutical composition containing the novel heterocyclic compound of any of [1] to [23] above, or a pharmaceutically acceptable salt thereof.

[25] A pharmaceutical agent containing the novel heterocyclic compound of any of [1] to [23] above, or a pharmaceutically acceptable salt thereof, which agent is selected from the group consisting of a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases or an agent for the prophylaxis or treatment of syndrome X.

[26] A method for the prophylaxis or treatment of hyperglycemia, hyperlipidemia, diseases caused by insulin resistance, diabetes, diabetic complication, impaired glucose tolerance, arteriosclerosis, obesity, inflammation, PPAR-mediated disease or syndrome X, which comprises administering a pharmaceutically effective amount of the heterocyclic compound of any of [1] to

[23] above or a pharmaceutically acceptable salt thereof to a patient.

[27] Use of a novel heterocyclic compound of any of [1] to [23] above or a pharmaceutically acceptable salt thereof for the production of a pharmaceutical composition for the prophylaxis or treatment of hyperglycemia, hyperlipidemia, diseases caused by insulin resistance, diabetes, diabetic complication, impaired glucose tolerance, arteriosclerosis, obesity, inflammation, PPAR-mediated disease or syndrome X.

DETAILED DESCRIPTION OF THE INVENTION

Each symbol used in the present specification is explained in the following.

The $C_{1-4}$ alkyl for $R^4$, $R^7$, $R^9$, $R^{11}$ and $R^{14}$ is a linear or branched chain alkyl having 1 to 4 carbon atoms, such as methyl, ethyl, propyl, isopropyl, butyl, isobutyl, sec-butyl, tert-butyl and the like, preferably methyl, ethyl, propyl and isopropyl.

The $C_{1-6}$ alkyl for $R^1$, $R^{10}$ and $R^{12}$ is a linear or branched chain alkyl having 1 to 6 carbon atoms, such as methyl, ethyl, propyl, isopropyl, butyl, isobutyl, sec-butyl, tert-butyl, pentyl, isopentyl, neopentyl, hexyl and the like, preferably methyl, ethyl, propyl, tert-butyl, butyl, isobutyl and isopentyl.

The $C_{1-8}$ alkyl for $R^5$, $R^6$ and $R^{13}$ is a linear or branched chain alkyl having 1 to 8 carbon atoms, such as methyl, ethyl, propyl, isopropyl, butyl, isobutyl, sec-butyl, tert-butyl, pentyl, isopentyl, neopentyl, hexyl, heptyl, octyl and the like, preferably methyl, ethyl, propyl, tert-butyl, butyl, pentyl and hexyl.

The $C_{5-8}$ alkyl for $R^8$ is a linear or branched chain alkyl having 5 to 8 carbon atoms, such as pentyl, isopentyl, neopentyl, hexyl, heptyl, octyl and the like, preferably pentyl, neopentyl and hexyl.

In the $C_{2-6}$ alkyl optionally substituted by halogen for $R^3$, halogen is chlorine atom, bromine atom, iodine atom or fluorine atom. The $C_{2-6}$ alkyl is a linear or branched chain alkyl having 2 to 6 carbon atoms, such as ethyl, propyl, isopropyl, butyl, isobutyl, tert-butyl, pentyl, neopentyl, hexyl and the like. The $C_{2-6}$ alkyl substituted by halogen is exemplified by 2-chloroethyl, 2-bromethyl, 2-iodoethyl, 2-fluoroethyl, 2,2-difluoroethyl, 2,2,2-trifluoroethyl, pentafluoroethyl, 2,2,3,3-tetrafluoropropyl, 3,3,3-trifluoropropyl, 4,4,4-trifluorobutyl, 5,5,5-trifluoropentyl, 6,6,6-trifluorohexyl and the like, preferably 2-fluoroethyl, 2,2-difluoroethyl, 2,2,2-trifluoroethyl, pentafluoroethyl and 2,2,3,3-tetrafluoropropyl.

In the $C_{1-6}$ alkyl optionally substituted by halogen for $R^2$ and $R^{10}$, halogen is chlorine atom, bromine atom, iodine atom or fluorine atom. The $C_{1-6}$ alkyl is a linear or branched chain alkyl having 1 to 6 carbon atoms, such as methyl, ethyl, propyl, isopropyl, butyl, isobutyl, tert-butyl, pentyl, neopentyl, hexyl and the like. The $C_{1-6}$ alkyl substituted by halogen is exemplified by fluoromethyl, difluoromethyl, trifluoromethyl, chloromethyl, dichloromethyl, trichloromethyl, bromomethyl, dibromomethyl, tribromomethyl, 2-chloroethyl, 2-bromoethyl, 2-iodoethyl, 2-fluoroethyl, 2,2-difluoroethyl, 2,2,2-trifluoroethyl, pentafluoroethyl, 2,2,3,3-tetrafluoropropyl, 3-fluoropropyl, 3,3-difluoropropyl 3,3,3,2,2-pentafluoropropyl, 3,3,3-trifluoropropyl, 4,4,4-trifluorobutyl, 5,5,5-trifluoropentyl, 6,6,6-trifluorohexyl and the like, preferably 3-fluoropropyl, 3,3-difuoropropyl, trifluoromethyl, 2,2,2-trifluoroethyl, 2,2-difluoroethyl, 3,3,3-trifluoropropyl and 3,3,3,2,2-pentafluoropropyl.

The $C_{3-8}$ cycloalkyl for $R^2$ and $R^{10}$ is cycloalkyl having 3 to 8 carbon atoms, such as cyclopropyl, cyclobutyl, cyclopentyl, cyclohexyl, cycloheptyl, cyclooctyl and the like, preferably cyclopropyl, cyclobutyl, cyclopentyl and cyclohexyl.

The $C_{4-8}$ cycloalkyl for $R^8$ is cycloalkyl having 4 to 8 carbon atoms, such as cyclobutyl, cyclopentyl, cyclohexyl, cycloheptyl, cyclooctyl and the like, preferably cyclopentyl and cyclohexyl.

The $C_{2-8}$ alkenyl for $R^5$ and $R^{10}$ is a linear or branched chain alkenyl having 2 to 8 carbon atoms, such as vinyl, 1-propenyl, 2-propenyl, isopropenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl and the like, preferably 1-propenyl, 1-butenyl, 1-pentenyl and 1-hexenyl.

The $C_{2-6}$ alkenyl for $R^2$ is a linear or branched alkenyl having 2 to 6 carbon atoms, such as vinyl, 1-propenyl, 2-propenyl, isopropenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 1-hexenyl, 2-hexenyl, 3-hexenyl, 4-hexenyl, 5-hexenyl and the like, preferably 3-butenyl, 4-pentenyl and 5-hexenyl.

As the aryl for $R^2$, $R^5$, $R^{10}$, $R^{12}$, $R^{13}$ and $R^{15}$, phenyl, naphthyl and the like, preferably phenyl, are exemplified.

As the aromatic heterocycle for $R^5$, $R^{10}$ and $R^{15}$, a monocyclic hetero ring and fused hetero ring having at least one hetero atom selected from the group consisting of oxygen atom, nitrogen atom and sulfur atom are preferable. The fused heterocycle in the present invention is a two ring system, which encompasses one having hetero atoms on both rings. Preferable monocyclic hetero ring is a 5- or 6-membered ring. The hetero ring constituting a preferable fused hetero ring is 5- or 6-membered hetero ring, and the ring without a hetero ring constituting a preferable fused heterocycle is a 5 or 6-membered ring. The aromatic hetero ring is, for example, a monocyclic hetero ring such as furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl or pyrazinyl and the like; a fused hetero ring such as indolyl, isoindolyl, indolinyl, isoindolinyl, indazolyl, benzofuranyl, benzothiophenyl, benzoimidazolyl, benzoxazolyl, benzothiazolyl, quinolyl, isoquinolyl, benzoxazinyl, benzothiazinyl, furo[2,3-b]pyridyl, thieno[2,3-b]pyridyl, naphthyridinyl, imidazopyridyl, oxazolopyridyl, thiazolopyridyl and the like, which are preferably furyl, thienyl, pyridyl, oxazolyl, thiazolyl, indolyl, indolinyl, benzofuranyl, benzothiophenyl, quinolyl and isoquinolyl.

The $C_{3-8}$ cycloalkyl $C_{1-3}$ alkyl for $R^2$ and $R^{10}$ is that wherein the cycloalkyl moiety has 3 to 8 carbon atoms and the alkyl moiety is a linear or branched chain alkyl having 1 to 3 carbon atoms, such as cyclopropylmethyl, cyclobutylmethyl, cyclopentylmethyl, cyclohexylmethyl, cycloheptylmethyl, yclooctylmethyl, cyclopropylethyl, cyclobutylethyl, yclopentylethyl, cyclohexylethyl, cycloheptylethyl, cyclooctylethyl, cyclopropylpropyl, cyclobutylpropyl, cyclopentylpropyl, cyclohexylpropyl, cycloheptylpropyl, cyclooctylpropyl, 1-methylcyclopentyl-1-yl, 1-methylcyclohexyl-1-yl and the like. Preferred are cyclopropylmethyl, cyclopropylethyl, 1-methylcyclopentyl-1-yl, 1-methylcyclohexyl-1-yl, cyclopentylmethyl and cyclohexylmethyl.

The $C_{1-4}$ alkoxy $C_{1-6}$ alkyl for $R^{10}$ is that wherein the alkoxy moiety is a linear or branched chain alkyl having 1 to 4 carbon atoms and the alkyl moiety is a linear or branched chain alkyl having 1 to 6 carbon atoms, such as methoxymethyl, ethoxymethyl, propyloxymethyl, isopropyloxymethyl, butoxymethyl, methoxyethyl, ethoxyethyl, propyloxyethyl, butoxyethyl, methoxypropyl, ethoxypropyl, propyloxypropyl, butoxypropyl, methoxybutyl, ethoxybutyl, propyloxybutyl, butoxybutyl, methoxypentyl, ethoxypentyl, propyloxypentyl, butoxypentyl, methoxyhexyl, ethoxyhexyl, propyloxyhexyl, butoxyhexyl and the like. Preferred are methoxymethyl, methoxyethyl, ethoxymethyl, propyloxymethyl, isopropyloxymethyl and ethoxyethyl.

The optionally substituted aryl $C_{1-3}$ alkyl for $R^2$ is aryl substituted by at least one linear or branched chain alkyl having 1 to 3 carbon atoms, such as that wherein the aryl moiety is phenyl, naphthyl and the like and the alkyl moiety is a linear or branched alkyl having 1 to 3 carbon atoms. When it is not substituted by the above-mentioned substituent, it is, for example, benzyl, 1-naphthylmethyl, 2-naphthylmethyl, 2-phenylethyl, 2-(1-naphthyl)ethyl, 2-(2-naphthyl)ethyl, 3-phenylpropyl, 3-(1-naphthyl)propyl, 3-(2-naphthyl)propyl, 1-phenylethyl, 2-phenylpropyl, 1-(1-naphthyl)ethyl, 1-(2-naphthyl)ethyl, 1-(1-naphthyl)propyl, 1-(2-naphthyl)propyl, 2-(1-naphthyl)propyl, 2-(2-naphthyl)propyl and the like. Preferred are benzyl, 2-phenylethyl, 3-phenylpropyl, 1-naphthylmethyl and 2-naphthylmethyl. Examples of the substituent include $C_{1-4}$ alkyl, $C_{1-4}$ alkoxy, hydroxy, halogen atom (e.g., chlorine, bromine, iodine, fluorine), nitro, amino and the like. The number of the substituent is preferably 1 or 2.

The $C_{1-4}$ alkylthio $C_{1-6}$ alkyl for $R^8$ and $R^{10}$ is that wherein the alkyl moiety of the alkylthio moiety is a linear or branched chain alkyl having 1 to 4 carbon atoms and the alkyl moiety is a linear or branched chain alkyl having 1 to 6 carbon atoms, such as methylthiomethyl, methylthioethyl, methylthiopropyl, methylthiobutyl, methylthiopentyl, methylthiohexyl, ethylthiomethyl, ethylthioethyl, ethylthiopropyl, ethylthiobutyl, ethylthiopentyl, ethylthiohexyl, propylthiomethyl, propylthioethyl, propylthiopropyl, propylthiobutyl, propylthiopentyl, propylthiohexyl, isopropylthiomethyl, butylthiomethyl, butylthioethyl, butylthiopropyl, butylthiobutyl, butylthiopentyl, butylthiohexyl and the like. Preferred are methylthiomethyl, methylthioethyl, ethylthiomethyl, ethylthioethyl, isopropylthiomethyl and methylthiopropyl.

The $C_{1-6}$ alkyl substituted by $(R^9)_2N-$, wherein $R^9$ is optionally the same as the other $R^9$ and is a hydrogen atom or $C_{1-4}$ alkyl, for $R^{10}$ is that wherein the alkyl moiety, which is alkyl having 1 to 6 carbon atoms, is substituted by the aforementioned $(R^9)_2N-$. Examples of such $C_{1-6}$ alkyl substituted by $(R^9)_2N-$ include aminomethyl, methylaminomethyl, dimethylaminomethyl, aminoethyl, methylaminoethyl, dimethylaminoethyl, aminopropyl, dimethylaminopropyl, aminobutyl, aminopentyl, aminohexyl, diethylaminomethyl, diethylaminoethyl, ethylaminoethyl and the like. Preferred are aminomethyl, methylaminomethyl, dimethylaminomethyl, aminoethyl, methylaminoethyl, dimethylaminoethyl, aminopropyl and dimethylaminopropyl.

$R^1$ is preferably a hydrogen atom.

Preferable $R^2$ is —CO—C($R^4$)=C($R^4$)—$R^5$ wherein $R^4$ is a hydrogen atom and $R^5$ is $C_{1-8}$ alkyl or $C_{2-8}$ alkenyl, or —CO—C≡C—$R^6$ wherein $R^6$ is $C_{1-8}$ alkyl, or $C_{2-6}$ alkenyl.

In the formula (I), Y—(CH$_2$)n-O— is preferably bonded to the 7-position of the tetrahydroisoquinoline skeleton. In Y—(CH$_2$)n-O—, n is preferably 2.

Y is preferably a group of the formula

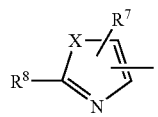

wherein each symbol is as defined above.

More preferable Y is that wherein, in the above-mentioned formula, (1) $R^7$ is a hydrogen atom or $C_{1-4}$ alkyl, $R^8$ is $R^{10}$—C($R^9$)=C($R^9$)— wherein $R^9$ is optionally the same as the other $R^9$ and is a hydrogen atom or $C_{1-4}$ alkyl and $R^1$ is $C_{1-6}$ alkyl, $C_{2-8}$ alkenyl or aryl, (2) $R^7$ is a hydrogen atom or $C_{1-4}$ alkyl, $R^8$ is $R^{13}$-Z- wherein $R^{13}$ is $C_{1-8}$ alkyl or aryl and Z is a sulfur atom, (3) $R^7$ is a hydrogen atom or $C_{1-4}$ alkyl and $R^8$ is $C_{5-8}$ alkyl or $C_{4-8}$ cycloalkyl, (4) $R^7$ is a hydrogen atom or $C_{1-4}$ alkyl, $R^8$ is $R^{10}$—C($R^9$)=C($R^9$)— wherein $R^9$ is a hydrogen atom and $R^{10}$ is $C_{3-8}$ cycloalkyl, and more preferable Y is that wherein, in the above-mentioned formula, (5) $R^7$ is $C_{1-4}$ alkyl, $R^8$ is $R^{10}$—C($R^9$)=C($R^9$)— wherein $R^9$ is optionally the same as the other $R^9$ and is a hydrogen atom or $C_{1-4}$ alkyl, $R^{10}$ is $C_{1-6}$ alkyl, and X is an oxygen atom, or (6) $R^7$ is $C_{1-4}$ alkyl, $R^8$ is $R^{10}$—C($R^9$)=C($R^9$)— wherein $R^9$ is a hydrogen atom, $R^{10}$ is aryl, and X is an oxygen atom.

X for Y is preferably an oxygen atom.

Particularly preferable Y is selected from the following (a) to (n).

(a)

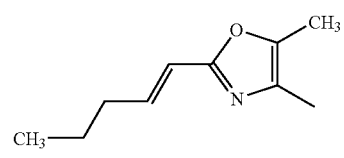

(b)

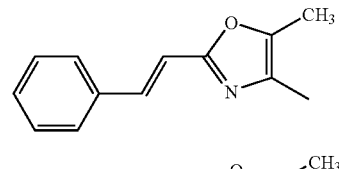

(c)

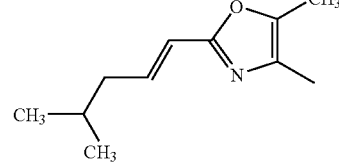

-continued (d)

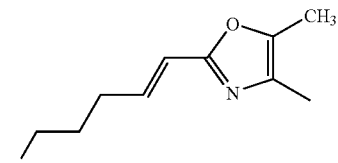

(e)

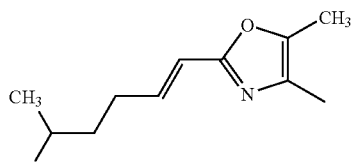

(f)

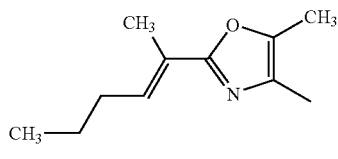

(g)

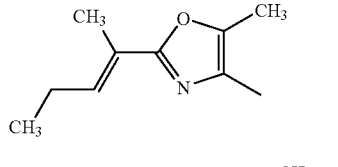

(h)

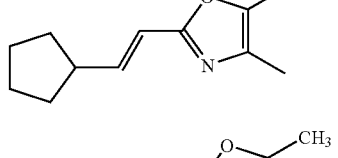

(i)

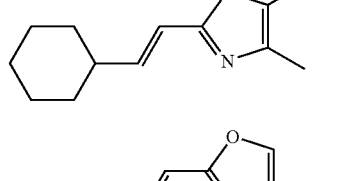

(j)

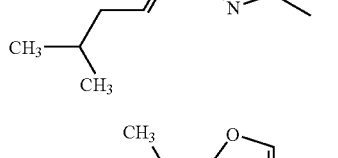

(k)

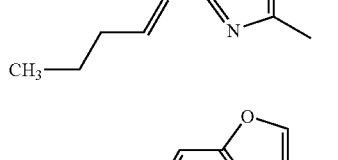

(l)

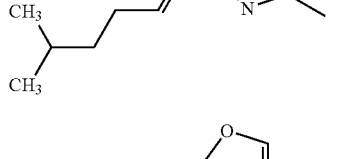

(m)

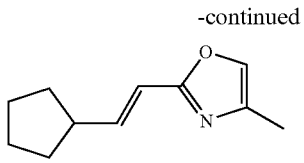
(n)

The heterocyclic compound (I) comprises stereoisomers due to an asymmetric carbon at the 3-position carbon of 1,2,3,4-tetrahydroisoquinoline ring. The most preferable configuration is

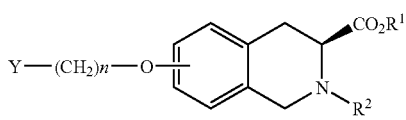

wherein $R^1$, $R^2$, Y and n are as defined above.

When, in the formula (I), $R^2$ is —CO—C($R^4$)=C($R^4$)—$R^5$ wherein $R^4$ and $R^5$ are as defined above, $R^8$ is $R^{10}$—C($R^9$)=C($R^9$)— wherein $R^9$ and $R^{10}$ are as defined above, or Y is $R^{15}$—C($R^{14}$)=N—O— wherein $R^{14}$ and $R^{15}$ are as defined above, stereoisomers (Z form and E form) are present at the double bond or the oxime moiety, both isomers of which are encompassed in the present invention.

The compound (I) of the present invention may form a pharmaceutically acceptable salt.

When the compound (I) has a basic group, an acid addition salt can be formed. The acid for forming such acid addition salt is not particularly limited, as long as it can form a salt with a basic part and is a pharmaceutically acceptable acid. Examples of the acid include inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like.

When the compound (I) has an acidic group such as carboxyl group and the like, for example, alkali metal salts (e.g., sodium salt, potassium salt and the like), alkaline earth metal salts (e.g., calcium salt, magnesium salt and the like), organic base salts (e.g., tert-butylamine salt, triethylamine salt, dicyclohexylamine salt, ethanolamine salt, pyridine salt, and the like) and the like can be formed.

Examples of the heterocyclic compound of the formula (I) and a pharmaceutically acceptable salt thereof include the following:

(1) 2-(2,4-hexadienoyl)-7-[2-(5-methyl-2-styryloxazol-4-yl)ethoxy]-1,2,3,4-tetrahydroisoquinoline-(3S)-carboxylic acid, (2) 2-(2-heptenoyl)-7-[2-(5-methyl-2-styryloxazol-4-yl)ethoxy]-1,2,3,4-tetrahydroisoquinoline-(3S)-carboxylic acid, (3) 2-(2-hexynoyl)-7-[2-(5-methyl-2-styryloxazol-4-yl)ethoxy]-1,2,3,4-tetrahydroisoquinoline-(3S)-carboxylic acid, (4) 7-[2-(5-methyl-2-styryloxazol-4-yl)ethoxy]-2-pentafluoropropionyl-1,2,3,4-tetrahydroisoquinoline-(3S)-carboxylic acid, (5) 2-(2-heptenoyl)-7-[2-(5-methyl-2-styrylthiazol-4-yl)ethoxy]-1,2,3,4-tetrahydroisoquinoline-(3S)-carboxylic acid, (6) 2-(2,4-hexadienoyl)-7-[2-(5-methyl-2-(1-penten-1-yl)oxazol-4-yl)ethoxy]-1,2,3,4-tetrahydroisoquinoline-(3S)-carboxylic acid, (7) 2-(2-heptenoyl)-7-[2-(5-methyl-2-(1-penten-1-yl)oxazol-4-yl)ethoxy]-1,2,3,4-tetrahydroisoquinoline-(3S)-carboxylic acid, (8) 2-(2-hexynoyl)-7-[2-(5-methyl-2-(1-penten-1-yl)oxazol-4-yl)ethoxy]-1,2,3,4-tetrahydroisoquinoline-(3S)-carboxylic acid, (9) 2-(2,4-hexadienoyl)-7-[2-(5-methyl-2-(1,3-pentadien-1-yl)oxazol-4-yl)ethoxy]-1,2,3,4-tetrahydroisoquinoline-(3S)-carboxylic acid,

(10) 2-(2,4-hexadienoyl)-7-[2-(5-methyl-2-pentyloxazol-4-yl)ethoxy]-1,2,3,4-tetrahydroisoquinoline-(3S)-carboxylic acid,

(11) 7-[2-(2-cyclopentyl-5-methyloxazol-4-yl)ethoxy]-2-(2,4-hexadienoyl)-1,2,3,4-tetrahydroisoquinoline-(3S)-carboxylic acid,

(12) 7-[2-(2-cyclohexyl-5-methyloxazol-4-yl)ethoxy]-2-(2,4-hexadienoyl)-1,2,3,4-tetrahydroisoquinoline-(3S)-carboxylic acid,

(13) 7-[2-(2-benzoylaminothiazol-5-yl)ethoxy]-2-(2-heptenoyl)-1,2,3,4-tetrahydroisoquinoline-(3S)-carboxylic acid,

(14) 7-[2-(2-butyrylaminothiazol-5-yl)ethoxy]-2-(2-heptenoyl)-1,2,3,4-tetrahydroisoquinoline-(3S)-carboxylic acid,

(15) 2-(2-heptenoyl)-7-[2-(4-methyl-2-phenylsulfanylthiazol-5-yl)ethoxy]-1,2,3,4-tetrahydroisoquinoline-(3S)-carboxylic acid, and

(16) 2-(2-heptenoyl)-7-[2-(1-phenylethylideneaminoxy)ethoxy]-1,2,3,4-tetrahydroisoquinoline-(3S)-carboxylic acid, and pharmaceutically acceptable salts thereof.

Of the aforementioned examples (1)-(16), the following compounds (1)-(3) and pharmaceutically acceptable salts thereof are particularly preferable, because they have a superior hypoglycemic action, a blood hypolipidemic action, an insulin resistance-improving action and a PPAR (peroxisome proliferator-activated receptor) activating action:

(1) 7-[2-(5-methyl-2-styryloxazol-4-yl)ethoxy]-2-pentafluoropropionyl-1,2,3,4-tetrahydroisoquinoline-(3S)-carboxylic acid, (2) 2-(2-heptenoyl)-7-[2-(5-methyl-2-(trans-1-penten-1-yl)oxazol-4-yl)ethoxy]-1,2,3,4-tetrahydroisoquinoline-(3S)-carboxylic acid, and (3) 2-(2-hexynoyl)-7-[2-(5-methyl-2-(trans-1-penten-1-yl)oxazol-4-yl)ethoxy]-1,2,3,4-tetrahydroisoquinoline-(3S)-carboxylic acid.

The following compounds (1)-(17), and pharmaceutically acceptable salts thereof are preferable examples of the present invention:

(1) 2-(2,4-hexadienoyl)-7-{2-[5-methyl-2-(4-methyl-1-penten-1-yl)oxazol-4-yl]ethoxy}-1,2,3,4-tetrahydroisoquinoline-(3S)-carboxylic acid, (2) 2-(2-heptenoyl)-7-{2-[5-methyl-2-(4-methyl-1-penten-1-yl)oxazol-4-yl]ethoxy}-1,2,3,4-tetrahydroisoquinoline-(3S)-carboxylic acid, (3) 2-(2,4-hexadienoyl)-7-{2-[2-(1-hexen-1-yl)-5-methyloxazol-4-yl]ethoxy}-1,2,3,4-tetrahydroisoquinoline-(3S)-carboxylic acid, (4) 2-(2,4-hexadienoyl)-7-{2-[5-methyl-2-(5-methyl-1-hexen-1-yl)oxazol-4-yl]ethoxy}-1,2,3,4-tetrahydroisoquinoline-(3S)-carboxylic acid, (5) 2-(2,4-hexadienoyl)-7-{2-[5-methyl-2-(1-methyl-1-penten-1-yl)oxazol-4-yl]ethoxy}-1,2,3,4-tetrahydroisoquinoline-(3S)-carboxylic acid, (6) 2-(2,4-hexadienoyl)-7-{2-[5-methyl-2-(1-methyl-1-buten-1-yl)oxazol-4-yl]ethoxy}-1,2,3,4-tetrahydroisoquinoline-(3S)-carboxylic acid, (7) 2-(2-hexenoyl)-7-{2-[5-methyl-2-(4-methyl-1-penten-1-yl)oxazol-4-yl]ethoxy}-1,2,3,4-tetrahydroisoquinoline-(3S)-carboxylic acid, (8) 7-{2-[5-methyl-2-(1-penten-1-yl)oxazol-4-yl]ethoxy}-2-(2,2,3,3,3-pentafluoropropionyl)-1,2,3,4-tetrahydroisoquinoline-(3S)-carboxylic acid, (9) 7-{2-[2-(4,4-dimethyl-1-penten-1-yl)-5-methyloxazol-4-yl]ethoxy}-2-(2,4-hexadienoyl)-1,2,3,4-tetrahydroisoquinoline-(3S)-carboxylic acid,

(10) 2-(2,4-hexadienoyl)-7-{2-[5-methyl-2-(3-methyl-1-buten-1-yl)oxazol-4-yl]ethoxy)-1,2,3,4-tetrahydroisoquinoline-(3S)-carboxylic acid,

(11) 2-(2,4-hexadienoyl)-7-(2-{5-methyl-2-[2-(1-methylcyclohexan-1-yl)vinyl]oxazol-4-yl)}ethoxy)-1,2,3,4-tetrahydroisoquinoline-(3S)-carboxylic acid,

(12) 7-{2-[2-(3,3-dimethyl-1-buten-1-yl)-5-methyloxazol-4-yl]ethoxy}-2-(2,4-hexadienoyl)-1,2,3,4-tetrahydroisoquinoline-(3S)-carboxylic acid,

(13) 2-(2,4-hexadienoyl)-7-{2-[2-(3-methoxy-1-propen-1-yl)-5-methyloxazol-4-yl]ethoxy}-1,2,3,4-tetrahydroisoquinoline-(3S)-carboxylic acid,

(14) 7-{2-[2-(2-cyclopentylvinyl)-5-methyloxazol-4-yl]ethoxy}-2-(2,4-hexadienoyl)-1,2,3,4-tetrahydroisoquinoline-(3S)-carboxylic acid,

(15) 7-{2-[2-(2-cyclohexylvinyl)-5-methyloxazol-4-yl]ethoxy}-2-(2,4-hexadienoyl)-1,2,3,4-tetrahydroisoquinoline-(3S)-carboxylic acid,

(16) 2-(3-butenyl)-7-{2-[5-methyl-2-(4-methyl-1-penten-1-yl)oxazol-4-yl]ethoxy}-1,2,3,4-tetrahydroisoquinoline-(3S)-carboxylic acid, and

(17) 7-{2-[5-methyl-2-(4-methyl-1-penten-1-yl)oxazol-4-yl]ethoxy)-2-(4-pentenyl)-1,2,3,4-tetrahydroisoquinoline-(3S)-carboxylic acid.

In addition, the following compounds (1)-(8), and pharmaceutically acceptable salts thereof are preferable examples of the present invention:

(1) 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic acid, (2) 2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, (3) 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, (4) 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylic acid, (5) 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid, (6) 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylic acid, (7) 2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylic acid, and (8) 2-(2-hexenoyl)-7-(2-[5-methyl-2-(4-methyl-trans-1-penten-1-yl)oxazol-4-yl]ethoxy}-1,2,3,4-tetrahydroisoquinoline-(3S)-carboxylic acid.

Furthermore, the following compounds (1)-(6), and pharmaceutically acceptable salts thereof are preferable examples of the present invention:

(1) 7-{2-[5-methyl-2-(trans-1-penten-1-yl)oxazol-4-yl]ethoxy}-2-(2,2,3,3,3-pentafluoropropionyl)-1,2,3,4-tetrahydroisoquinoline-(3S)-carboxylic acid, (2) 7-{2-[2-(4,4-dimethyl-trans-1-penten-1-yl)-5-methyloxazol-4-yl]ethoxy}-2-(2,4-hexadienoyl)-1,2,3,4-tetrahydroisoquinoline-(3S)-carboxylic acid, (3) 2-(2,4-hexadienoyl)-7-{2-[5-methyl-2-(3-methyl-trans-1-buten-1-yl)oxazol-4-yl]ethoxy}-1,2,3,4-tetrahydroisoquinoline-(3S)-carboxylic acid, (4) 2-(2,4-hexadienoyl)-7-(2-{5-methyl-2-[trans-(1-methylcyclohexan-1-yl)vinyl]oxazol-4-yl}ethoxy)-1,2,3,4-tetrahydroisoquinoline-(3S)-carboxylic acid, (5) 7-(2-[2-(3,3-dimethyl-trans-1-buten-1-yl)-5-methyloxazol-4-yl]ethoxy}-2-(2,4-hexadienoyl)-1,2,3,4-tetrahydroisoquinoline-(3S)-carboxylic acid, and (6) 2-(2,4-hexadienoyl)-7-{2-[2-(3-methoxy-trans-1-propen-1-yl)-5-methyloxazol-4-yl]ethoxy}-1,2,3,4-tetrahydroisoquinoline-(3S)-carboxylic acid.

Moreover, the following compounds (1) and (2), and pharmaceutically acceptable salts thereof are preferable examples of the present invention:

(1) 7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylic acid, and (2) 7-{2-[2-(trans-2-cyclohexylvinyl)-5-methyloxazol-4-yl]ethoxy)-2-(2,4-hexadienoyl)-1,2,3,4-tetrahydroisoquinoline-(3S)-carboxylic acid.

Additionally, the following compounds (1), and (2), and pharmaceutically acceptable salts thereof are preferable examples of the present invention:

(1) 2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic acid, and (2) 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid.

Furthermore, the following compounds (1)-(9), and pharmaceutically acceptable salts thereof are preferable examples of the present invention:

(1) 2-(2,4-hexadienoyl)-7-{2-[2-(4-methyl-trans-1-penten-1-yl)oxazol-4-yl]ethoxy)-1,2,3,4-tetrahydroisoquinoline-(3S)-carboxylic acid, (2) 7-{2-[2-(trans-2-cyclopentylvinyl)oxazol-4-yl]ethoxy)-2-(2,4-hexadienoyl)-1,2,3,4-tetrahydroisoquinoline-(3S)-carboxylic acid, (3) 7-{2-[2-(trans-2-cyclohexylvinyl)oxazol-4-yl]ethoxy}-2-(2,4-hexadienoyl)-1,2,3,4-tetrahydroisoquinoline-(3S)-carboxylic acid, (4) 2-(2-heptenoyl)-7-{2-[2-(4-methyl-trans-1-penten-1-yl)oxazol-4-yl]ethoxy}-1,2,3,4-tetrahydroisoquinoline-(3S)-carboxylic acid, (5) 2-(2-hexenoyl)-7-{2-[2-(4-methyl-trans-1-penten-1-yl)oxazol-4-yl]ethoxy}-1,2,3,4-tetrahydroisoquinoline-(3S)-carboxylic acid, (6) 2-(2,4-hexadienoyl)-7-{2-[2-(trans-hexen-1-yl)oxazol-4-yl]ethoxy}-1,2,3,4-tetrahydroisoquinoline-(3S)-carboxylic acid, (7) 2-(2,4-hexadienoyl)-7-{2-[2-(1-methyl-trans-1-penten-1-yl)oxazol-4-yl]ethoxy}-1,2,3,4-tetrahydroisoquinoline-(3S)-carboxylic acid, (8) 2-(2,4-hexadienoyl)-7-{2-[2-(1-methyl-trans-1-buten-1-yl)oxazol-4-yl]ethoxy}-1,2,3,4-tetrahydroisoquinoline-(3S)-carboxylic acid, and (9) 2-(2,4-hexadienoyl)-7-{2-[(5-methyl-trans-1-hexen-1-yl)oxazol-4-yl]ethoxy}-1,2,3,4-tetrahydroisoquinoline-(3S)-carboxylic acid.

The compound (I) of the present invention and a pharmaceutically acceptable salt thereof can be produced by any of the following production methods.

Production Method 1

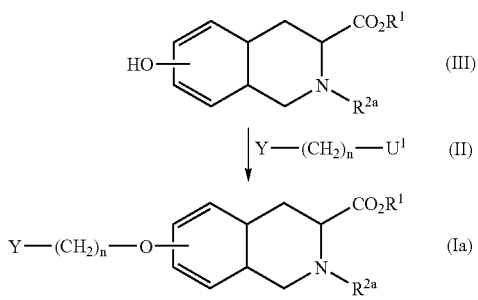

wherein $R^1$, Y and n are as defined above, $R^{2a}$ is —CO—$R^3$ wherein $R^3$ is as defined above, —CO—C($R^4$)=C($R^4$)—$R^5$ wherein $R^4$ and $R^5$ are as defined above, —CO—C≡C—$R^6$ wherein $R^6$ is as defined above, aryl, optionally substituted aryl $C_{1-3}$ alkyl, $C_{1-6}$ alkyl optionally substituted by halogen, $C_{2-6}$ alkenyl, $C_{3-8}$ cycloalkyl or $C_{3-8}$ cycloalkyl $C_{1-3}$ alkyl, and $U^1$ is hydroxy and/or a leaving group such as halogen atom (fluorine atom, chlorine atom, bromine atom, iodine atom) or alkanesulfonyloxy (e.g., ethanesulfonyloxy, ethanesulfonyloxy, propanesulfonyloxy, trifluoromethanesulfonyloxy and the like), arylsulfonyloxy (e.g., phenylsulfonyloxy and tolylsulfonyloxy and the like).

In Production Method 1, a compound having the formula (II) (compound (II)) is reacted with a compound having the formula (III) (compound (III)) to produce a compound having the formula (Ia) (compound (Ia)).

Production Method 1-a: When $U^1$ is hydroxy group, Production Method 1 includes a dehydrating reaction such as Mitsunobu reaction (Reagents for Organic Synthesis by Fieser & Fieser, Vol. 6,645) and the like. The reaction generally proceeds in the presence of a solvent using an azo compound and a phosphine. Examples of the azo compound include di-$C_{1-4}$ alkyl azodicarboxylate (e.g., dimethyl azodicarboxylate, diethyl azodicarboxylate, diisopropyl azodicarboxylate and the like), azodicarboxamide (e.g., 1,1'-azobis(N,N'-dimethylformamide), 1,1'-(azodicarbonyl)dipiperidine and the like) and the like. Examples of the phosphine include triarylphosphine (e.g., triphenylphosphine and the like), tri($C_{1-8}$ alkyl) phosphine (e.g., tri-n-butylphosphine, tri-n-hexylphosphine, tri-n-octylphosphine and the like) and the like.

The solvent to be used in Production Method 1-a is free of any particular limitation as long as it is inert to the reaction. Examples thereof include dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like, a mixture of these, and the like.

The amount of compound (II) to be used in Production Method 1-a is free of any particular limitation, and is generally 1-5 moles, preferably 1-3 moles, per 1 mole of compound (III). The amount of the azo compound and the phosphine to be used is generally 1-3 moles, preferably 1-1.5 moles, per 1 mole of compound (III).

While the reaction conditions in Production Method 1-a, such as reaction temperature, reaction time and the like vary depending on the reaction reagent, reaction solvent and the like to be used, the reaction is generally carried out at −30° C. to 50° C. for 30 min to about a dozen hours.

Production Method 1-b: When $U^1$ is a leaving group such as halogen atom or alkanesulfonyloxy (e.g., methanesulfonyloxy, ethanesulfonyloxy, propanesulfonyloxy, trifluoromethanesulfonyloxy and the like), arylsulfonyloxy (e.g., phenylsulfonyloxy, tolylsulfonyloxy and the like) and the like, Production Method 1-b is performed in a solvent similar to those used in Production Method 1-a in the presence of a base.

The base to be used in Production Method 1-b is free of any particular limitation, and is exemplified by inorganic bases such as alkali metal carbonates (e.g., sodium carbonate, sodium hydrogen carbonate, potassium carbonate, potassium bicarbonate and the like), alkali metal hydroxides (e.g., sodium hydroxide, potassium hydroxide and the like), metal hydride compounds (e.g., sodium hydride, potassium hydride, calcium hydride and the like) and the like; and organic bases such as alkali metal alcoholates (e.g., sodium methoxide, sodium ethoxide, potassium-t-butoxide and the like), amines (e.g., triethylamine, diisopropylethylamine and the like) and the like.

The amount of compound (II) to be used in Production Method 1-b is free of any particular limitation, and is generally 1-5 moles, preferably 1-3 moles, per 1 mole of compound (III). The amount of the base to be used is generally 1-5 moles, preferably 1-3 moles, per 1 mole of compound (III).

In Production Method 1-b, a catalyst can be used in a solvent in the presence of a base. Preferable solvent is toluene and the catalyst is exemplified by quaternary ammonium salts such as tetramethyl ammonium bromide, tetraethyl ammonium bromide, tetrabutyl ammonium bromide, tetraethyl ammonium chloride, tetraethyl ammonium fluoride, benzyltrimethyl ammonium bromide and the like, and tris[2-(2-methoxyethoxy)ethyl]amine. Preferably, tetraethylammonium fluoride or tris[2-(2-methoxyethoxy)ethyl]amine is used. The amount of catalyst to be used is generally 0.1-1 mole, preferably 0.1-0.5 mole, per 1 mole of compound (III).

While the reaction conditions in Production Method 1-b, such as reaction temperature, reaction time and the like vary depending on the reaction reagent, reaction solvent and the like to be used, the reaction is generally carried out at −30° C. to 150° C. for 30 min to about a dozen hours.

In Production Method 1-a and Production Method 1-b, $R^1$ of compound (III) is preferably a $C_{1-6}$ alkyl group. In this case, a compound (Ia) wherein $R^1$ is a $C_{1-6}$ alkyl group is obtained, which is hydrolyzed by a method known per se to give a compound (Ia) wherein $R^1$ is a hydrogen atom.

Production Method 2

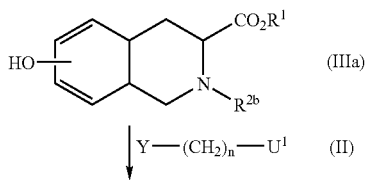

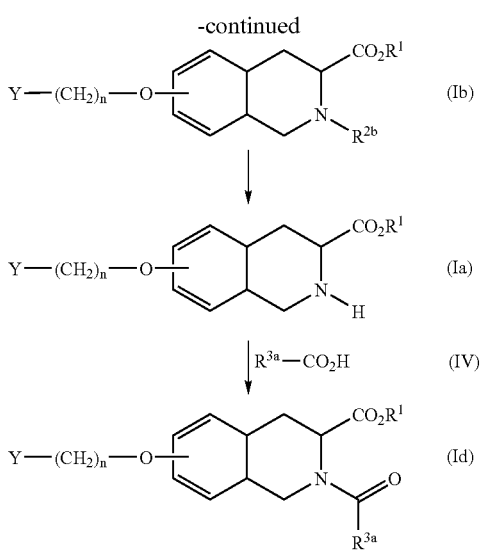

wherein $R^1$, Y, n and $U^1$ are as defined above, $R^{2b}$ is an amino-protecting group, and $R^{3a}$ is $C_{2-6}$ alkyl optionally substituted by halogen, —C($R^4$)=C($R^4$)—$R^5$ wherein $R^4$ and $R^5$ are as defined above, —C≡C—$R^6$ wherein $R^6$ is as defined above or

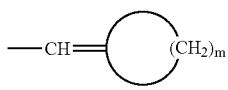

wherein m is an integer of 2 to 7.

The amino-protecting group for $R^{2a}$ is exemplified by formyl, monochloroacetyl, dichloroacetyl, trichloroacetyl, trifluoroacetyl, methoxycarbonyl, ethoxycarbonyl, benzyloxycarbonyl, p-nitrobenzyloxycarbonyl, diphenylmethyloxycarbonyl, methoxymethylcarbonyl, methoxymethyloxycarbonyl, trimethylsilyl, 2,2,2-trichloroethoxycarbonyl, 2-methylsulfonylethyloxycarbonyl, tert-butoxycarbonyl (hereinafter to be also referred to as Boc), trityl and the like.

In Production Method 2, the amino-protecting group of a compound having the formula (Ib) (compound (Ib)) is removed by a method known per se to give a compound having the formula (Ic) (compound (Ic)), which is reacted with a compound having the formula (IV) (compound (IV)) to give a compound having the formula (Id) (compound (Id)). The compound (Ib) can be produced by reacting compound (II) and a compound having the formula (IIIa) (compound (IIIa)) in the reaction mode and reaction conditions similar to those of the reaction between compound (II) and compound (III) in Production Method 1.

In Production Method 2, the compound (IV) is subjected to the reaction not only in the form of a free acid but also in the form of a salt (e.g., salt of sodium, potassium, calcium, triethylamine, pyridine and the like), a reactive derivative (e.g., acid halide such as acid chloride, acid bromide and the like; acid anhydride; mixed acid anhydride with substituted phosphoric acid (e.g., dialkylphosphoric acid and the like), with alkylcarbonate (e.g., monoethyl carbonate and the like), and the like; active amide which is acid amide with imidazole and the like; esters such as cyanomethyl ester, 4-nitrophenyl ester and the like; and the like.

When compound (IV) is used in the form of a free acid or a salt in Production Method 2, the reaction is preferably carried out in the presence of a condensing agent. Examples of the condensing agent include dehydrating agents such as carbodiimide compounds (e.g., N,N'-dicyclohexylcarbodiimide, 1-ethyl-3-(3'-dimethylaminopropyl)carbodiimide, N-cyclohexyl-N'-morpholinoethylcarbodiimide, N-cyclohexyl-N'-(4-diethylaminocyclohexyl)carbodiimide and the like); azolide compounds (e.g., N,N'-carbonyldiimidazole, N,N'-thionyldiimidazole and the like) and the like; and the like. When these condensing agents are used, the reaction is considered to proceed via a reactive derivative of compound (IV).

In Production Method 2, the reaction between compound (Ic) and compound (IV) is generally carried out in an inert solvent. Examples of the solvent include acetone, dioxane, acetonitrile, chloroform, benzene, methylene chloride, ethylene chloride, tetrahydrofuran, ethyl acetate, N,N-dimethylformamide, pyridine, water and the like, mixtures of these and the like. In addition, a base such as triethylamine, pyridine, 4-dimethylaminopyridine, potassium carbonate and the like can be used. When such base is used, the amount of the base to be used is generally 1-5 moles, preferably 1-3 moles, per 1 mole of compound (Ic).

In Production Method 2, the amount of compound (IV) to be used is generally 1-5 moles, preferably 1-3 moles, per 1 mole of compound (Ic).

While the reaction conditions of compound (Ic) and compound (IV) in Production Method 2, such as reaction temperature, reaction time and the like vary depending on the reaction reagent, reaction solvent and the like to be used, the reaction is generally carried out at −30° C. to 150° C. for 30 min to about a dozen hours.

Production Method 3

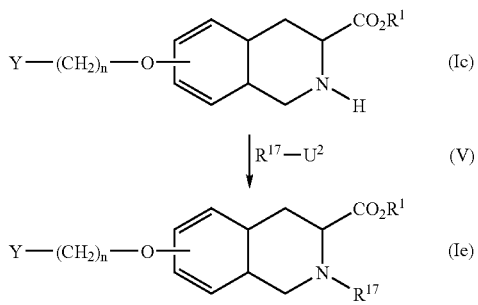

wherein $R^1$, Y and n are as defined above, $R^{17}$ is $C_{1-6}$ alkyl optionally substituted by halogen, $C_{3-8}$ cycloalkyl, $C_{3-8}$ cycloalkyl $C_{1-3}$ alkyl or optionally substituted aryl $C_{1-3}$ alkyl, and $U^2$ is a leaving group such as a halogen atom, alkanesulfonyloxy group (e.g., methanesulfonyloxy, ethanesulfonyloxy, propanesulfonyloxy, trifluoromethanesulfonyloxy and the like), arylsulfonyloxy group (e.g., phenylsulfonyloxy and tolylsulfonyloxy and the like), and the like.

In Production Method 3, compound (Ic) is reacted with a compound having the formula (V) (compound (V)) to give a compound having the formula (Ie) (compound (Ie)).

The reaction between compound (Ic) and compound (V) to form compound (Ie) can be carried out in a solvent inert to the reaction in the presence of a base. Examples of the solvent include dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like, mixtures of these and the like.

The ratio of the molar amounts of compound (Ic) and compound (V) to be used is free of any particular limitation, but 1-5 moles, preferably 1-3 moles, of compound (V) is used, per 1 mole of compound (Ic).

The base to be used in this reaction is free of any particular limitation, and is exemplified by inorganic bases such as alkali metal carbonates (e.g., sodium carbonate, sodium bicarbonate, potassium carbonate, potassium bicarbonate and the like), alkali metal hydroxides (e.g., sodium hydroxide, potassium hydroxide and the like) and the like; alkali metal alcoholates such as sodium methoxide, sodium ethoxide, potassium-t-butoxide and the like; metal hydride compounds such as sodium hydride, potassium hydride, calcium hydride and the like; and organic bases such as triethylamine, diisopropylethylamine and the like.

The ratio of the molar amounts of compound (Ic) and the base to be used is free of any particular limitation, but 1-5 moles, preferably 1-3 moles, of a base is used, per 1 mole of compound (Ic).

While the reaction conditions, such as reaction temperature, reaction time and the like vary depending on the reaction reagent, reaction solvent and the like to be used, the reaction is generally carried out at −30° C. to 150° C. for 30 min to about a dozen hours.

In this production method, $R^1$ of compound (Ic) is preferably alkyl group, whereby compound (Ie) wherein $R^1$ is alkyl group is obtained, which is hydrolyzed by a method known per se to give compound (Ie) wherein $R^1$ is a hydrogen atom.

Production Method 4

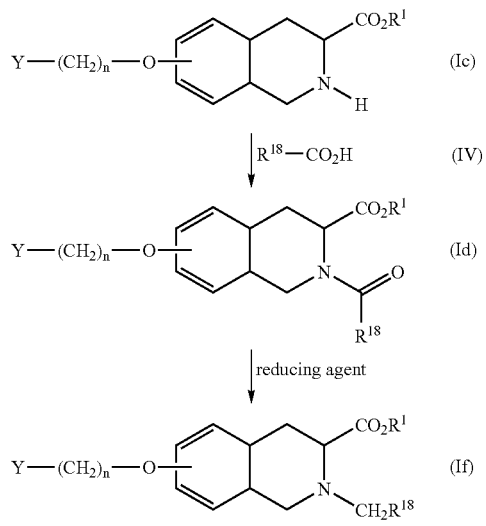

wherein $R^1$, Y and n are as defined above, and $R^{18}$ is a group that makes a group of the formula: —$CH_2R^{18}$ represent $C_{1-6}$ alkyl optionally substituted by halogen, $C_{3-8}$ cycloalkyl, $C_{3-8}$ cycloalkyl $C_{1-3}$ alkyl or optionally substituted aryl $C_{1-3}$ alkyl.

In Production Method 4, compound (Id) obtained by reacting compound (Ic) with compound (IV) is reduced with a suitable reducing agent to produce compound (If).

The $C_{1-6}$ alkyl optionally substituted by halogen, $C_{3-8}$ cycloalkyl, $C_{3-8}$ cycloalkyl $C_{1-3}$ alkyl and optionally substituted aryl $C_{1-3}$ alkyl with regard to $R^{18}$ are as defined with regard to $R^2$.

In Production Method 4, the reaction between compound (Ic) and compound (IV) to give compound (Id) can be carried out in the same reaction mode and reaction conditions as those of compound (Ic) and compound(IV) in Production Method 2.

In Production Method 4, the solvent to be used for the reaction between compound (Id) and reducing agent to give compound (If) is free of any particular limitation as long as it does not adversely affect the reaction, and is exemplified by water, methanol, ethanol, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like, mixtures of these and the like.

The reducing agent to be used for this reaction is not particularly limited and metal hydride complex such as lithium aluminum hydride, sodium cyanoborohydride, sodium borohydride and the like or borane can be used.

The ratio of the molar amounts of compound (Id) and the reducing agent to be used is free of any particular limitation, but 1-5 moles, preferably 1-3 moles, of reducing agent is used per 1 mole of compound (Id).

While the reaction conditions, such as reaction temperature, reaction time and the like vary depending on the reaction reagent, reaction solvent and the like to be used, the reaction is generally carried out at −30° C. to 50° C. for 30 min to about a dozen hours.

Production Method 5

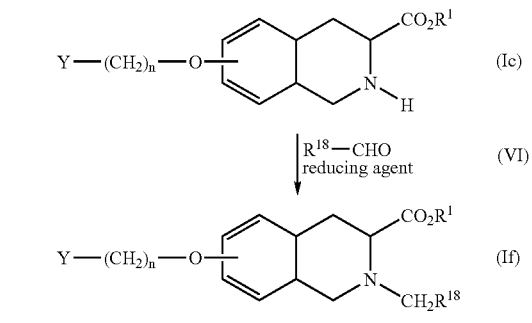

wherein $R^1$, Y, n and $R^{18}$ are as defined above.

In production method 5, compound (Ic) is reacted with compound (VI) in the presence of a suitable reducing agent to produce compound (If).

In Production Method 5, the reaction between compound (Ic) and compound (VI) to give compound (If) is carried out by condensation in a solvent that does not adversely affect the reaction, such as water, methanol, ethanol, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like, mixtures of these and the like, in the presence of a suitable reducing agent.

The reducing agent to be used for this reaction is not particularly limited and metal hydride complex such as lithium aluminum hydride, sodium cyanoborohydride, sodium borohydride and the like or borane can be used.

The ratio of the molar amounts of compound (Ic) and compound (VI) to be used is free of any particular limitation, but 1-5 moles, preferably 1-3 moles, of compound (VI) is used per 1 mole of compound (Ic).

The ratio of the molar amounts of compound (Ic) and the reducing agent to be used is free of any particular limitation, but 1-5 moles, preferably 1-3 moles, of reducing agent is used per 1 mole of compound (Ic).

While the reaction conditions, such as reaction temperature, reaction time and the like vary depending on the reaction reagent, reaction solvent and the like to be used, the reaction is generally carried out at −30° C. to 50° C. for 30 min to about a dozen hours.

When the compound (III) to be used in Production Method 1 is that wherein, in the formula (III), $R^{2a}$ is —CO—$R^3$ wherein $R^3$ is as defined above, —CO—C($R^4$)=C($R^4$)—$R^5$ wherein $R^4$ and $R^5$ are as defined above, —CO—C≡C—$R^6$ wherein $R^6$ is as defined above, $C_{1-6}$ alkyl optionally substituted by halogen, $C_{3-8}$ cycloalkyl, $C_{3-8}$ cycloalkyl $C_{1-3}$ alkyl or optionally substituted aryl $C_{1-3}$ alkyl, the reactions of Production Method I can be carried out in the same reaction mode and reaction conditions as those of the reaction between compound (Ic) and compound (IV) in Production Method 2 or the reaction between compound (Ic) and compound (V) in Production Method 3, or the reaction to obtain compound (If) from compound (Ic) in Production Method 4, using a compound of the formula (IIIa)

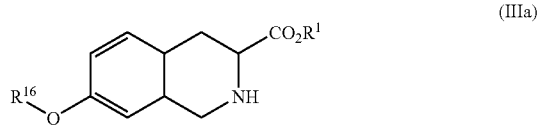

(IIIa)

wherein $R^1$ is as defined above and $R^{16}$ is a hydrogen atom or a hydroxy-protecting group, (compound (IIIa)) as a starting material.

When, in the formula (III), $R^{2a}$ is an amino-protecting group, the amino-protecting group can be introduced by a method known per se, whereby a compound (III), wherein $R^{2a}$ is an amino-protecting group, can be produced.

Examples of the hydroxy-protecting group to be used for this production method include ethers and acetals such as methyl ether, isopropyl ether, tert-butyl ether, benzyl ether, allyl ether, methoxymethyl ether, tetrahydropyranyl ether, p-bromophenacyl ether, trimethylsilyl ether and the like, and esters such as formyl, acetyl, monochloroacetyl, dichloroacetyl, trifluoroacetyl, methoxycarbonyl, ethoxycarbonyl, benzyloxycarbonyl, p-nitrobenzyloxycarbonyl, 2,2,2-trichloroethoxycarbonyl, benzoyl, methanesulfonyl, benzenesulfonyl, p-toluenesulfonyl and the like.

For production of compound (III), $R^{16}$ of compound (IIIa) is preferably a hydroxy-protecting group. The hydroxy-protecting group can be removed by a method known per se to give compound (III) easily.

The heterocyclic compound (I) obtained in the above-mentioned Production Methods 1-5 may be isolated by a conventional method, and optionally purified by a conventional method such as recrystallization, preparative thin-layer chromatography, column chromatography and the like.

The heterocyclic compound (I) may be converted to a pharmaceutically acceptable salt thereof by a method known per se.

A pharmaceutical composition comprising the heterocyclic compound (I) or a pharmaceutically acceptable salt thereof of the present invention may contain an additive and the like. As an additive, exemplified are excipient (e.g., starch, lactose, sugar, calcium carbonate, calcium phosphate and the like), binder (e.g., starch, gum arabic, carboxymethylcellulose, hydroxypropylcellulose, crystalline cellulose and the like), lubricant (e.g., magnesium stearate, talc and the like), disintegrator (e.g., carboxymethylcellulose calcium, talc and the like), and the like.

The above-mentioned components are mixed to give a preparation for oral administration, such as capsule, tablet, powder, granule, dry syrup and the like, or a preparation for parenteral administration, such as injection, suppository and the like, according to a method known per se.

While the dose of the heterocyclic compound (I) or a pharmaceutically acceptable salt thereof may vary according to the administration subject, symptom and other factors, when it is orally administered to an adult patient with, for example, diabetes, diabetic complication or hyperlipidemia, the single dose is approximately 1-500 mg, which is administered 1 to 3 times a day.

The heterocyclic compound (I) and a pharmaceutically acceptable salt thereof of the present invention show a superior hypoglycemic action, a blood hypolipidemic action, an insulin resistance-improving action and a PPAR activating action in mammals (e.g., human, horse, cattle, dog, cat, rat, mouse, hamster and the like), and are useful as a hypoglycemic agent, a hypolipidemic agent, an insulin resistance improver, a therapeutic agent of diabetes, a therapeutic agent of diabetic complication, a glucose intolerance improver, an anti-arteriosclerosis agent, an anti-obesity agent, an antiinflammatory agent, an agent for the prophylaxis or treatment of PPAR-mediated disease or an agent for the prophylaxis or treatment of syndrome X. To be specific, the heterocyclic compound (I) and a pharmaceutically acceptable salt thereof of the present invention are useful for the prophylaxis or treatment of diabetes, diabetic complication, hyperlipidemia, arteriosclerosis, hyperglycemia, diseases caused by insulin resistance glucose intolerance, diseases caused by insulin resistance, obesity, inflammation, PPAR-mediated disease or syndrome X.

The present invention is explained in more detail by Examples and Reference Examples, which are not to be construed. as limitative.

EXAMPLES

Example 1 sodium 2-(2-heptenoyl)-7-[2-(5-methyl-2-(trans-1-penten-1-yl) oxazol-4-yl)ethoxy]-1,2,3,4-tetrahydroisoquinoline-(3S)-carboxylate (1) Methyl 2-(2-heptenoyl)-7-hydroxy-1,2,3,4-tetrahydroisoquinoline-(3S)-carboxylate (500 mg) and 2-[5-methyl-2-(trans-1-penten-1-yl)oxazol-4-yl]ethyl methanesulfonate (650 mg) were dissolved in toluene (15 ml), and potassium carbonate (650 mg) and tetraethylammonium fluoride hydrate (100 mg) were added. The mixture was stirred at 80° C. for 10 h. To the reaction mixture was added ethyl acetate (50 ml), and the mixture was washed with water (30 ml) and saturated brine (30 ml), and dried ($Na_2SO_4$). The solvent was evaporated under reduced pressure and the obtained residue was purified by silica gel column chromatography to give methyl 2-(2-heptenoyl)-7-[2-(5-methyl-2-(trans-1-penten-1-yl)oxazol-4-yl)ethoxy]-1,2,3,4-tetrahydroisoquinoline-(3S)-carboxylate (620 mg).

$^1$H-NMR (CDCl$_3$) δ (ppm); 0.95 (6H, br-t), 1.15-1.75 (6H, m), 2.00-2.45 (4H, m), 2.27 (3H, s), 2.87 (2H, t, J=6.8 Hz), 3.00-3.30 (2H, m), 3.60 (3H, s), 4.15 (2H, t, J=6.8 Hz), 4.50-5.70 (3H, m), 6.18 (1H, d, J=15.8 Hz), 6.35-7.20 (5H, m), 7.04 (1H, d, J=8.2 Hz).

(2) The compound (200 mg) obtained in the above-mentioned (1) was dissolved in a mixture (5 ml) of tetrahydrofuran-methanol (3:1), and 1M aqueous lithium hydroxide solution (1.2 ml) was added. The mixture was stirred at 50° C. for 30 min and acidified with 10% aqueous citric acid solution. The solution was concentrated under reduced pressure and the precipitated gummy material was extracted with ethyl acetate (20 ml). The ethyl acetate layer was washed with saturated brine (10 ml) and dried ($Na_2SO_4$). Ethyl acetate was evaporated under reduced pressure and the obtained residue was purified by silica gel column chromatography to give 2-(2-heptenoyl)-7-[2-(5-methyl-2-(trans-1-penten-1-yl)oxazol-4-yl)ethoxy]-1,2,3,4-tetrahydroisoquinoline-(3S)-carboxylic acid (170 mg). This was dissolved in methanol (2 ml) and 0.586M sodium hydroxide-methanol solution (0.62 ml) was added, and methanol was evaporated under reduced pressure. The obtained residue was dissolved in water (1 ml) and freeze-dried to give the title compound (170 mg).

IR ν (KBr) $cm^{-1}$; 1653, 1595, 1506.

$^1$H-NMR (DMSO-$d_6$) δ (ppm); 0.89 (6H, br-t), 1.10-1.75 (6H, m), 1.90-2.20 (4H, m), 2.25 (3H, s), 2.79 (2H, br-t), 3.00-3.30 (2H, br), 4.07 (2H, br-t), 4.20-5.15 (3H, m), 6.19 (1H, d, J=16.7 Hz), 6.30-6.80 (5H, m), 6.96 (1H, d, J=8.4 Hz).

Example 2

2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic acid (1) Methyl 2-tert-butoxycarbonyl-7-hydroxy-1,2,3,4-tetrahydroisoquinoline-(3S)-carboxylate (0.5 g) and 2-[5-methyl-2-(trans-1-penten-1-yl)oxazol-4-yl]ethyl methanesulfonate (0.67 g) were dissolved in toluene (5 ml), and potassium carbonate (0.68 g) and tetraethylammonium fluoride hydrate (0.12 g) were added. The mixture was stirred at 80° C. for 18 h. To the reaction mixture was added ethyl acetate (20 ml), and the mixture was washed with water (20 ml) and saturated brine (20 ml), and dried ($Na_2SO_4$). The solvent was evaporated under reduced pressure and the obtained residue was purified by silica gel column chromatography to give methyl 2-tert-butoxycarbonyl-7-[2-(5-methyl-2-(trans-1-penten-1-yl)oxazol-4-yl)ethoxy]-1,2,3,4-tetrahydroisoquinoline-(3S)-carboxylate (0.57 g).

IR ν (neat) $cm^{-1}$; 1746, 1698, 1615, 1533, 1505.

$^1$H-NMR (CDCl$_3$) δ (ppm); 0.89 (3H, t, J=7.0 Hz), 1.20-1.80 (11H, m), 2.00-2.40 (2H, m), 2.28 (3H, s), 2.89 (2H, t, J=6.8 Hz), 2.90-3.20 (2H, m), 3.61 (3H, s), 4.15 (2H, t, J=6.8 Hz), 4.40-4.90 (2H, m), 5.00-5.20 (1H, m), 6.18 (1H, d, J=16.1 Hz), 6.73 (1H, dt, J=16.1, 6.8 Hz), 6.50-6.80 (2H, m), 7.01 (1H, d, J=8.4 Hz).

(2) The compound (0.55 g) obtained in the above-mentioned (1) was dissolved in formic acid (3 ml), and 8.78M hydrogen chloride-2-propanol solution (0.39 ml) was added under ice-cooling. The mixture was stirred at room temperature for 30 min and ethyl acetate (20 ml) was added to the reaction mixture. After neutralization with saturated aqueous sodium hydrogen carbonate, two layers were separated and the obtained ethyl acetate layer was washed with saturated brine (10 ml), and dried ($Na_2SO_4$). Ethyl acetate was evaporated under reduced pressure and the obtained residue was purified by silica gel column chromatography to give methyl 7-[2-(5-methyl-2-(trans-1-penten-1-yl)oxazol-4-yl)ethoxy]-1,2,3,4-tetrahydroisoquinoline-(3S)-carboxylate (0.39 g).

IR ν (neat) $cm^{-1}$; 1743, 1505.

$^1$H-NMR (CDCl$_3$) δ (ppm); 0.94 (3H, t, J=7.0 Hz), 1.20-1.70 (2H, m), 2.00-2.40 (3H, m), 2.27 (3H, s), 2.50-3.20 (2H, m), 2.86 (2H, t, J=6.7 Hz), 3.60-3.90 (1H, m), 3.76 (3H, s), 4.05 (2H, s), 4.14 (2H, t, J=6.7 Hz), 6.17 (1H, d, J=16.0 Hz), 6.40-6.80 (1H, m), 6.54 (1H, d, J=2.6 Hz), 6.69 (1H, dd, J=8.3, 2.6 Hz), 6.99 (1H, d, J=8.3 Hz)

(3) The compound (0.36 g) obtained in the above-mentioned (2) was dissolved in methylene chloride (5 ml), and sorbic chloride (0.13 g) and triethylamine (0.17 ml) were added. The mixture was stirred at room temperature for 30 min and ethyl acetate (30 ml) was added. The mixture was washed with 10% aqueous citric acid solution (15 ml) and saturated brine (15 ml), and dried ($Na_2SO_4$). The solvent was evaporated under reduced pressure and the obtained residue was purified by silica gel column chromatography to give methyl 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylate (0.4 g).

IR ν (neat) $cm^{-1}$; 1740, 1655, 1628, 1605, 1506.

$^1$H-NMR (CDCl$_3$) δ (ppm); 0.95 (3H, t, J=6.8 Hz), 1.20-1.70 (2H, m), 1.85 (3H, d, J=5.0 Hz), 2.00-2.40 (2H, m), 2.04 (3H, s), 2.87 (2H, t, J=6.7 Hz), 3.00-3.25 (2H, m), 3.59 (3H, s), 4.15 (2H, t, J=6.7 Hz), 4.50-5.65 (3H, m), 6.00-6.90 (7H, m), 7.03 (1H, d, J=8.2 Hz), 7.15-7.55 (1H, m).

(4) The compound (0.37 g) obtained in the above-mentioned (3) was dissolved in a mixture (9.4 ml) of tetrahydrofuran-methanol (3:1), and 1M aqueous lithium hydroxide solution (2.35 ml) was added and the mixture was stirred at 50° C. for 30 min. The mixture was acidified with 10% aqueous citric acid solution, and the resulting mixture was concentrated under reduced pressure. The precipitated gummy material was extracted with ethyl acetate (50 ml), and the ethyl acetate layer was washed with saturated brine (30 ml), and dried ($Na_2SO_4$). Ethyl acetate was evaporated under reduced pressure and the obtained residue was purified by silica gel column chromatography to give the title compound (0.28 g).

IR ν (Nujol) $cm^{-1}$; 1728, 1651, 1616, 1531, 1504.

$^1$H-NMR (CDCl$_3$) δ (ppm); 0.92 (3H, t, J=6.8 Hz), 1.20-1.75 (2H, m), 1.84 (3H, d, J=4.8 Hz), 2.14 (2H, m), 2.22 (3H, s), 2.65 (2H, br-t), 2.80-3.50 (2H, m), 3.95 (2H, br-t), 4.60-5.10 (3H, m), 5.40-5.65 (1H, m), 6.00-6.80 (5H, m), 7.02 (1H, d, J=8.4 Hz), 7.15-7.55 (1H, m), 9.80-10.50 (1H, br).

Example 3 methyl 2-(2-heptenoyl)-7-[2-(5-methyl-2-(trans-1-penten-1-yl)oxazol-4-yl)ethoxy]-1,2,3,4-tetrahydroisoquinoline-(3S)-carboxylate The compound (210 mg) obtained in Example 2(2) was dissolved in methylene chloride (2.1 ml), and 2-heptenoic acid (105 mg) and 1-ethyl-3-(3'-dimethylaminopropyl)carbodiimide hydrochloride (160 mg) were added. The mixture was stirred at room temperature for 1 h. Ethyl acetate (30 ml) was added, and the mixture was washed with 10% aqueous citric acid solution (15 ml) and saturated brine (15 ml), and dried ($Na_2SO_4$). The solvent was evaporated under reduced pressure, and the obtained residue was purified by silica gel column chromatography to give methyl 2-(2-heptenoyl)-7-[2-(5-methyl-2-(trans-1-penten-1-yl)oxazol-4-yl)ethoxy]-1,2,3,4-tetrahydroisoquinoline-(3S)-carboxylate (200 mg).

The $^1$H-NMR data were the same as those of the compound of Example 1(1).

The compounds of Examples 4-15 were synthesized in the same manner as in Examples 1-3.

Example 4

2-(2-hexynoyl)-7-[2-(5-methyl-2-(trans-1-penten-1-yl)oxazol-4-yl)ethoxy]-1,2,3,4-tetrahydroisoquinoline-(3S)-carboxylic acid IR ν (Nujol) cm$^{-1}$; 2237, 1717, 1684, 1616, 1576, 1506.
$^1$H-NMR (CDCl$_3$) δ (ppm); 0.85-1.20 (6H, m), 1.25-1.90 (4H, m), 2.00-2.50 (4H, m), 2.24 (3H, s), 2.60-3.50 (4H, m), 3.80-4.10 (2H, m), 4.35-5.20 (2H, m), 5.30-5.65 (1H, m), 6.18 (1H, d, J=16.0 Hz) 6.45-6.85 (3H, m), 7.02 (1H, d, J=7.9 Hz), 8.80-9.40 (1H, br).

Example 5

2-(2,4-hexadienoyl)-7-[2-(5-methyl-2-styryloxazol-4-yl)ethoxy]-1,2,3,4-tetrahydroisoquinoline-(3S)-carboxylic acid IR ν (Nujol) cm$^{-1}$; 1729, 1652, 1615, 1575.
$^1$H-NMR (CDCl$_3$) δ (ppm); 1.83 (3H, br-d), 2.28 (3H, s), 2.82 (2H, br-t), 2.90-3.50 (2H, m), 4.03 (2H, br-t), 4.60-5.10 (3H, m), 5.40-5.65 (1H, m), 6.00-6.80 (5H, m), 6.84 (1H, d, J=16.5 Hz), 7.04 (1H, d, J=8.4 Hz), 7.15-7.65 (7H, m), 9.40-10.20 (1H, br).

Example 6

2-(2-heptenoyl)-7-[2-(5-methyl-2-styryloxazol-4-yl)ethoxy)-1,2,3,4-tetrahydroisoquinoline-(3S)-carboxylic acid IR ν (Nujol) cm$^{-1}$; 1740, 1653, 1612, 1553, 1506.
$^1$H-NMR (CDCl$_3$) δ (ppm); 0.70-1.00 (3H, br), 1.10-1.75 (4H, m), 1.90-2.40 (2H, br), 2.29 (3H, s), 2.60-3.40 (4H, m), 3.75-4.20 (2H, m), 4.55-5.10 (2H, m), 5.40-5.70 (1H, m), 6.33 (1H, d, J=15.7 Hz), 6.55-7.25 (5H, m), 7.30-7.70 (6H, m), 8.00-8.80 (1H, br).

Example 7

2-(2-hexynoyl)-7-[2-(5-methyl-2-styryloxazol-4-yl)ethoxy]-1,2,3,4-tetrahydroisoquinoline-(3S)-carboxylic acid IR ν (Nujol) cm$^{-1}$; 2235, 1734, 1630, 1580, 1528, 1504.
$^1$H-NMR (CDCl$_3$) δ (ppm); 0.96,1.04 (3H, t, t, J=6.7 Hz), 1.35-1.80 (2H, m), 2.20-2.50 (2H, m), 2.29 (3H, s), 2.70-3.50 (4H, m), 3.80-4.15 (2H, m), 4.55-5.20 (2H, m), 5.30-5.60 (2H, m), 6.45-6.70 (2H, m), 7.85 (1H, d, J=16.5 Hz), 7.25-7.65 (6H, m), 7.90-8.60 (1H, br).

Example 8

7-[2-(5-methyl-2-styryloxazol-4-yl)ethoxy]-2-pentafluoropropionyl-1,2,3,4-tetrahydroisoquinoline-(3S)-carboxylic acid IR ν (Nujol) cm$^{-1}$; 1732, 1680, 1647, 1614, 1578, 1531, 1506.
$^1$H-NMR (CDCl$_3$+DMSO-d$_6$) δ (ppm); 2.34 (3H, s), 2.91 (2H, t, J=6.6 Hz), 3.10-3.30 (2H, m), 4.18 (2H, t, J=6.6 Hz), 4.40-5.30 (3H, m), 6.50-6.90 (2H, m), 6.84 (1H, d, J=16.5 Hz), 6.90-7.25 (2H, m), 7.30-7.60 (5H, m).

Example 9

2-(2-heptenoyl)-7-[2-(5-methyl-2-styrylthiazol-4-yl)ethoxy]-1,2,3,4-tetrahydroisoquinoline-(3S)-carboxylic acid IR ν (Nujol) cm$^{-1}$; 1732, 1657, 1614, 1585, 1558, 1506.
$^1$H-NMR (CDCl$_3$) δ (ppm); 0.75-1.05 (3H, br), 1.10-1.75 (4H, br), 2.00-2.50 (4H, m), 2.38 (3H, s), 2.70-3.40 (4H, m), 3.90-4.30 (2H, m), 4.50-5.10 (2H, m), 5.35-5.70 (1H, m), 6.10-7.70 (13H, m).

Example 10

2-(2,4-hexadienoyl)-7-[2-(5-methyl-2-(1,3-pentadien-1-yl)oxazol-4-yl)ethoxy]-1,2,3,4-tetrahydroisoquinoline-(3S)-carboxylic acid IR ν (Nujol) cm$^{-1}$; 1730, 1648, 1616, 1456, 1377, 990.
$^1$H-NMR (DMSO-d$_6$) δ (ppm); 1.83 (6H, br-s), 2.27 (3H, s), 2.6-3.4 (4H, m), 4.12 (2H, br-t), 4.2-5.0 (2H, m), 5.18 (1H, br-t), 5.9-7.4 (11H, m).

Example 11

2-(2,4-hexadienoyl)-7-[2-(5-methyl-2-pentyloxazol-4-yl)ethoxy]-1,2,3,4-tetrahydroisoquinoline-(3S)-carboxylic acid IR ν (Nujol) cm$^{-1}$; 1728, 1653, 1616, 1574, 1506.
$^1$H-NMR (CDCl$_3$) δ (ppm); 0.87 (3H, t, J=5.9 Hz), 1.10-1.40 (4H, m), 1.45-1.80 (2H, m), 1.84 (3H, d, J=4.6 Hz), 2.20 (3H, s), 2.65 (2H, t, J=8.1 Hz), 2.73 (2H, br-t, 3.93 (2H, br-t), 4.40-5.10 (3H, m), 5.45-5.70 (1H, m), 6.10-6.80 (5H, m), 7.03 (1H, d, J=8.6 Hz), 7.10-7.50 (1H, m), 9.10-10.00 (1H, br).

Example 12

7-[2-(2-cyclopentyl-5-methyloxazol-4-yl)ethoxy]-2-(2,4-hexadienoyl)-1,2,3,4-tetrahydroisoquinoline-(3S)-carboxylic acid IR ν (Nujol) cm$^{-1}$; 1733, 1652, 1615, 1568.
$^1$H-NMR (CDCl$_3$) δ (ppm); 1.0-2.0 (11H, m), 2.20 (3H, s), 2.77 (2H, t, J=6.0 Hz), 2.8-3.4 (3H, m), 3.93 (2H, t, J=6.4 Hz), 4.6-5.0 (2H, m), 5.54 (1H, br-t), 6.0-6.8 (5H, m), 7.02 (1H, d, J=8.4 Hz), 7.1-7.6 (1H, m), 8.8-9.6 (1H, br).

Example 13

7-[2-(2-cyclohexyl-5-methyloxazol-4-yl)ethoxy]-2-(2,4-hexadienoyl)-1,2,3,4-tetrahydroisoquinoline-(3S)-carboxylic acid IR ν (Nujol) cm$^{-1}$; 1733, 1652, 1616, 1456, 1377, 1260, 999.
$^1$H-NMR (DMSO-d$_6$) δ (ppm); 1.0-2.0 (13H, m), 2.20 (3H, s), 2.77 (2H, t, J=6.4 Hz), 2.8-3.4 (3H, m), 4.09 (2H, t, J=6.4 Hz), 4.2-5.0 (2H, m), 5.17 (1H, br-t), 5.9-7.3 (7H, m).

Example 14

2-(2-heptenoyl)-7-[2-(1-phenylethylideneaminoxy)ethoxy]-1,2,3,4-tetrahydroisoquinoline-(3S)-carboxylic acid IR ν (Nujol) cm$^{-1}$; 1732, 1716, 1651, 1574, 1506.
$^1$H-NMR (CDCl$_3$) δ (ppm); 0.75-1.05 (3H, m), 1.10-1.70 (4H, m), 2.00-2.40 (2H, m), 2.21 (3H, s), 2.80-3.30 (2H, m), 4.10-4.30 (2H, m), 4.40-5.10 (4H, m), 5.30-5.60 (1H, m), 6.15-7.15 (6H, m) 7.25-7.50 (3H, m), 7.60-7.80 (2H, m).

Example 15

2-(2-heptenoyl)-7-[2-(4-methyl-2-phenylsulfanylthiazol-5-yl)ethoxy]-1,2,3,4-tetrahydroisoquinoline-(3S)-carboxylic acid IR ν (Nujol) cm$^{-1}$; 1726, 1612, 1582, 1502.
$^1$H-NMR (DMSO-d$_6$) δ (ppm); 0.70-1.10 (3H, m), 1.20-1.70 (4H, m), 2.00-2.30 (2H, m), 2.29 (3H, s), 2.90-3.60 (5H, m), 4.04 (2H, t, J=5.9 Hz), 4.35-4.95 (2H, m), 5.00-5.30 (1H, m), 6.35-6.90 (4H, m), 7.09 (1H, d, J=7.9 Hz), 7.35-7.70 (5H, m).

Example 16

7-[2-(2-benzoylaminothiazol-5-yl)ethoxy]-2-(2-heptenoyl)-1,2,3,4-tetrahydroisoquinoline-(3S)-carboxylic acid (1) 2-(2-Aminothiazol-5-yl)ethyl methanesulfonate (2.43 g) and methyl 2-tert-butoxycarbonyl-7-hydroxy-1,2,3,4-tetrahydroisoquinoline-(3S)-carboxylate (2.17 g) were dissolved in N,N-dimethylformamide (50 ml), and cesium carbonate (5.20 g) was added. The mixture was stirred at 55° C. for 15 h. To the reaction mixture was added water (200 ml), and the mixture was extracted 3 times with ethyl acetate (100 ml). The ethyl acetate layer was washed twice with water (100 ml) and then with saturated brine (100 ml), and dried (Na$_2$SO$_4$). Ethyl acetate was evaporated under reduced pressure and the obtained residue was purified by column chromatography to give methyl 7-(2-aminothiazol-5-yl)ethoxy-2tert-butoxycarbonyl-1,2,3,4-tetrahydroisoquinoline-(3S)-carboxylate (2.20g).

$^1$H-NMR (CDCl$_3$) δ (ppm); 1.46,1.51 (9H, s, s), 2.80-3.3.0 (4H, m), 3.61 (3H, s), 4.07 (2H, t, J=6.3 Hz), 4.30-4.90 (4H, m), 4.95-5.25 (1H, m), 6.55-6.90 (3H, m), 7.03 (1H, d, J=8.4 Hz).

(2) The compound (500 mg) obtained in the above-mentioned (1) was dissolved in N,N-dimethylformamide (5.0 ml), and triethylamine (0.25 ml) and benzoyl chloride (0.16 ml) were added. The mixture was stirred at 55° C. for 15 h. To the reaction mixture was added water (20 ml), and the mixture was extracted 3 times with ethyl acetate (10 ml). The ethyl acetate layer was washed twice with water (20 ml) and then with saturated brine (20 ml), and dried (Na$_2$SO$_4$). Ethyl acetate was evaporated under reduced pressure and the obtained residue was purified by column chromatography to give methyl 7-(2-benzoylaminothiazol-5-yl)ethoxy-2-tertbutoxycarbonyl-1,2,3,4-tetrahydroisoquinoline-(3S)-carboxylate (535 mg).

IR ν (Nujol) cm$^{-1}$; 1746, 1684, 1605, 1582, 1555, 1535, 1506.
$^1$H-NMR (CDCl$_3$) δ (ppm); 1.46,1.51 (9H, s, s), 2.90-3.30 (5H, m), 3.61 (3H, s), 4.11 (2H, t, J=6.1 Hz), 4.20-4.90 (2H, m), 4.95-5.25 (1H, m), 6.55-6.90 (3H, m), 7.04 (1H, d, J=7.9 Hz), 7.30-7.70 (3H, m), 7.90-8.20 (2H, m).

(3) The compound (535 mg) obtained in the above-mentioned (2) was dissolved in formic acid (2.0 ml), and 8.78M hydrogen chloride-2-propanol solution (0.30 ml) was added under ice-cooling. The mixture was stirred at the same temperature for min. The reaction mixture neutralized with saturated aqueous sodium hydrogen carbonate, extracted with chloroform (30 ml) and dried (Na$_2$SO$_4$). Chloroform was evaporated under reduced pressure to give methyl 7-(2-benzoylaminothiazol-5-yl)ethoxy-1,2,3,4-tetrahydroisoquinoline-(3S)-carboxylate (401 mg).

IR ν (Nujol) cm$^{-1}$; 3161, 1744, 1659, 1603, 1582, 1558, 1535, 1501.
$^1$H-NMR (CDCl$_3$) δ (ppm); 2.90-3.10 (2H, m), 3.19 (2H, t, J=6.1 Hz), 3.60-3.80 (1H, m), 3.77 (3H, s), 4.00-4.30 (4H, m), 6.58 (1H, d, J=2.2 Hz), 6.74 (1H, dd, J=2.2, 8.4 Hz), 6.95-7.10 (2H, m), 7.30-7.60 (3H, m), 7.85-8.10 (2H, m).

(4) The compound (400 mg) obtained in the above-mentioned (3) was dissolved in methylene chloride (5.0 ml), and 2-heptenoic acid (0.19 ml) and 1-ethyl-3-(3'-dimethylaminopropyl)-carbodiimide hydrochloride (265 mg) were added under ice-cooling. The mixture was stirred at room temperature for 1 h, washed with 10% aqueous citric acid solution (10 ml) and then with saturated brine (30 ml), and dried (Na$_2$SO$_4$). Methylene chloride was evaporated under reduced pressure and the obtained residue was purified by column chromatography to give methyl 7-(2-benzoylaminothiazol-5-yl)ethoxy-2-(2-heptenoyl)-1,2,3,4-tetrahydroisoquinoline-(3S)-carboxylate (495 mg).

IR ν (neat) cm$^{-1}$; 3165, 1740, 1661, 1616, 1558, 1533, 1506.
$^1$H-NMR (CDCl$_3$) δ (ppm); 0.80-1.10 (3H, m), 1.20-1.70 (4H, m) 2.00-2.50 (2H, m), 3.00-3.45 (4H, m), 3.60 (3H, s), 4.12 (2H, t, J=5.9 Hz), 4.50-5.00 (2H, m), 5.40-5.60 (1H, m), 6.35 (1H, d, J=15.1 Hz), 6.65-7.20 (4H, m), 7.35-7.70 (3H, m), 7.80-8.15 (2H, m).

(5) The compound (490 mg) obtained in the above-mentioned (4) was dissolved in a mixture (20 ml) of tetrahydrofuran-methanol (3:1), and 1M aqueous lithium hydroxide solution (3.0 ml) was added. The mixture was stirred at 50° C. for 30 min and acidified with 10% aqueous citric acid solution. The solvent was evaporated under reduced pressure. The precipitated crystals were collected by filtration to give the title compound (342 mg).

IR ν (Nujol) cm$^{-1}$; 1734, 1655, 1603, 1560, 1541, 1506.
$^1$H-NMR (CDCl$_3$) δ (ppm); 0.80-1.10 (3H, m), 1.20-1.70 (4H, m), 2.00-2.50 (2H, m), 2.80-3.40 (4H, m), 3.80-4.20 (2H, m), 4.50-5.05 (2H, m), 5.50-5.80 (1H, m), 6.05-7.20 (6H, m), 7.30-7.70 (3H, m), 7.80-8.15 (2H, m), 9.60-11.20 (1H, br).

The compound of Example 17 was synthesized in the same manner as in Example 16.

Example 17

7-[2-(2-butyrylaminothiazol-5-yl)ethoxy]-2-(2-heptenoyl)-1,2,3,4-tetrahydroisoquinoline-(3S)-carboxylic acid IR ν (Nujol) cm$^{-1}$; 3172, 1734, 1692, 1655, 1612, 1562, 1504.
$^1$H-NMR (CDCl$_3$) δ (ppm); 0.94 (6H, t, J=7.0 Hz), 1.10-1.90 (6H, m) 2.10-2.60 (2H, m), 2.80-3.50 (4H, m), 3.80-4.30 (2H, m), 4.40-5.10 (2H, m), 5.55-5.80 (1H, m), 6.10-7.30 (6H, m), 9.60-11.20 (2H. br).

Example 18 methyl 7-(2-[5-methyl-2-(4-methyl-trans-1-penten-1-yl)oxazol-4-yl]ethoxy}-1,2,3,4-tetrahydroiso-quinoline-(3S)-carboxylate (1) Methyl 2-tert-butoxycarbonyl-7-hydroxy-1,2,3,4-tetrahydroisoquinoline-(3S)-carboxylate (1.0 g) and 2-[5-methyl-2-(4-methyl-trans-1-penten-1-yl)oxazol-4-yl]ethyl methanesulfonate (1.4 g) were dissolved in toluene (30 ml), and potassium carbonate (1.35 g) and tetraethylammonium fluoride hydrate (0.2 g) were added. The mixture was stirred at 80° C. for 13 h. To the reaction mixture was added ethyl acetate (50 ml), and the mixture was washed successively with water (50 ml) and saturated brine (30 ml), and dried ($Na_2SO_4$). The solvent was evaporated under reduced pressure and the obtained residue was purified by silica gel column chromatography to give methyl 2-tert-butoxycarbonyl-7-[2-7(5-methyl-2-(4-methyl-trans-1-penten-1-yl)oxazol-4-yl)ethoxy]-1,2,3,4-tetrahydroisoquinoline-(3S)-carboxylate (1.6 g).

IR ν (neat) $cm^{-1}$; 2957, 2928, 2872, 1746, 1701, 1614, 1533, 1506.

$^1$H-NMR ($CDCl_3$) δ (ppm); 0.94 (6H, d, J=6.3 Hz), 1.46, 1.50 (9H, s, s), 1.50-2.00 (1H, m), 2.11 (2H, t, J=6.8 Hz), 2.28 (3H, s), 2.87 (2H, t, J=6.6 Hz), 3.00-3.25 (2H, m), 3.61 (3H, s), 4.15 (2H, t, J=6.6 Hz), 4.45-5.25 (3H, m), 6.15 (1H, d, J=15.8 Hz), 6.45-6.80 (3H, m), 7.01 (1H, d, J=8.8 Hz).

(2) The compound (1.6 g) obtained in the above-mentioned (1) was dissolved in formic acid (8 ml), and 8.78M hydrogen chloride-2-propanol solution (1.1 ml) was added under ice-cooling. The mixture was stirred at room temperature for 15 min. To the reaction mixture were added ethyl acetate and water (50 ml each). After neutralization with sodium bicarbonate, two layers were separated, and the obtained ethyl acetate layer was washed with saturated brine (30 ml) and dried ($Na_2SO_4$). Ethyl acetate was evaporated under reduced pressure and the obtained residue was purified by silica gel column chromatography to give the title compound (1.17 g).

IR ν (neat) $cm^{-1}$; 3344, 2955, 2926, 2870, 1738, 1661, 1641, 1612, 1533, 1504.

$^1$H-NMR ($CDCl_3$) δ (ppm); 0.94 (6H, d, J=6.3 Hz), 1.50-1.95 (1H, m) 2.11 (2H, t, J=6.6 Hz), 2.12 (1H, br-s), 2.28 (3H, s), 2.87 (2H, t, J=6.8 Hz), 2.90-3.10 (2H, m), 3.55-3.90 (1H, m), 3.77 (3H, s), 4.06 (2H, s), 4.14 (2H, t, J=6.8 Hz), 6.16 (1H, d, J=15.8 Hz), 6.40-6.80 (3H, m), 7.00 (1H, d, J=8.4 Hz).

Example 19

2-(2,4-hexadienoyl)-7-{2-[5-methyl-2-(4-methyl-trans-1-penten-1-yl)oxazol-4-yl)ethoxy}-1,2,3,4-tetrahydroisoquinoline-(3S)-carboxylic acid (1) The compound (1.15 g) obtained in Example 18 was dissolved in methylene chloride (20 ml), and sorbic acid chloride (0.45 g) and triethylamine (0.6 ml) were added. The mixture was stirred at room temperature for 15 min and methylene chloride (30 ml) was added. The mixture was washed with water and saturated brine (30 ml each), and dried ($Na_2SO_4$). Methylene chloride was evaporated under reduced pressure and the obtained residue was purified by silica gel column chromatography to give methyl 2-(2,4-hexadienoyl)-7-[2-(5-methyl-2-(4-methyl-trans-1-penten-1-yl)oxazol-4-yl)ethoxy]-1,2,3,4-tetrahydroisoquinoline-(3S)-carboxylate (1.36 g).

IR ν (neat) $cm^{-1}$; 1740, 1655, 1628, 1533, 1508.

$^1$H-NMR ($CDCl_3$) δ (ppm); 0.94 (6H, d, J=6.4 Hz), 1.50-1.95 (4H, m), 2.11 (2H, t, J=7.0 Hz), 2.28 (3H, s), 2.87 (2H, t, J=6.6 Hz), 3.00-3.30 (2H, m), 3.60 (3H, s), 4.15 (2H, t, J=6.6 Hz), 4.50-5.15 (2H, m), 5.40-5.70 (1H, m), 6.00-6.90 (7H, m), 7.04 (1H, d, J=8.2 Hz), 7.15-7.55 (1H, m).

(2) The compound (1.36 g) obtained in the above-mentioned (1) was dissolved in a mixture (16 ml) of tetrahydrofuran-methanol (3:1), and 1M aqueous lithium hydroxide solution (8.3 ml) was added. The mixture was stirred at room temperature for 30 min and acidified with 10% aqueous citric acid solution. The solution was concentrated under reduced pressure and the precipitated gummy material was extracted with ethyl acetate (50 ml). The ethyl acetate layer was washed with saturated brine (30 ml), and dried ($Na_2SO_4$). Ethyl acetate was evaporated under reduced pressure to give the title compound (1.26 g).

IR ν (neat) $cm^{-1}$; 2959, 2930, 2872, 1738, 1651, 1620, 1583, 1533, 1506.

$^1$H-NMR ($CDCl_3$) δ (ppm); 0.92 (6H, d, J=6.4 Hz), 1.45-2.00 (1H, m), 1.84 (3H, d, J=4.9 Hz), 2.09 (2H, t, J=7.0 Hz), 2.23 (3H, s), 2.78 (2H, t, J=6.4 Hz), 2.95-3.40 (2H, m), 4.00 (2H, t, J=6.4 Hz), 4.30-5.65 (3H, m), 5.95-7.55 (9H, m).

Example 20 tert-butylamine 2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylate The compound (1.25 g) obtained in Example 19 was dissolved in methanol (7.0 ml), and tert-butylamine (0.55 ml) was added dropwise. Diisopropyl ether (70 ml) was added and the mixture was stirred at room temperature for 30 min. The precipitated crystals were collected by filtration to give the title compound (1.15 g).

IR ν (neat) $cm^{-1}$; 2741, 2633, 2544, 1653, 1628, 1558, 1506.

$^1$H-NMR ($CDCl_3$) δ (ppm); 0.93 (6H, d, J=6.6 Hz), 0.99 (9H, s) 1.60-2.00 (4H, m), 2.10 (2H, t, J=6.8 Hz), 2.28 (3H, s), 2.86 (2H, t, J=6.8 Hz), 2.90-3.40 (2H, m), 4.11 (2H, t, J=6.8 Hz), 4.30-5.25 (3H, m), 6.00-7.50 (12H, m).

Example 21 methyl 7-{2-[2-(trans-2-cyclopentylvinyl)-5-methyloxazol-4-yl]ethoxy}-1,2,3,4-tetrahydroisoquinoline-(3S)-carboxylate (1) Methyl 2-tert-butoxycarbonyl-7-hydroxy-1,2,3,4-tetrahydroisoquinoline-(3S)-carboxylate (2.93 g) and 2-[2-(trans-2-cyclopentylvinyl)-5-methyloxazol-4-yl]ethyl methanesulfonate (4.29 g) were dissolved in toluene (90 ml), and potassium carbonate (3.95 g) and tetraethylammonium fluoride hydrate (0.75 g) were added. The mixture was stirred at 90° C. for 16 h. To the reaction mixture was added ethyl acetate (30 ml), and the mixture was washed successively with water (50 ml) and saturated brine (50 ml), and dried ($Na_2SO_4$). The solvent was evaporated under reduced pressure and the obtained residue was purified by silica gel column chromatography to give methyl 2-tert-butoxycarbonyl-7-[2-(trans-2-cyclopentylvinyl)-5-methyloxazol-4-yl]oxazol-4-yl]ethoxy]-1,2,3,4-tetrahydroisoquinoline-(3S)-carboxylate (3.9 g).

IR ν (neat) cm$^{-1}$; 2955, 2970, 1742, 1699, 1614, 1533, 1506.

$^1$H-NMR (CDCl$_3$) δ (ppm); 1.20-2.00 (17H, m), 2.27 (3H, s), 2.34-2.74 (1H, m), 2.86 (2H, t, J=6.6 Hz), 2.99-3.20 (2H, m), 3.61 (3H, s), 4.12 (2H, t, J=6.6 Hz), 4.24-5.20 (3H, m), 6.15 (1H, d, J=16.1 Hz), 6.61 (1H, dd, J=16.1, 7.5 Hz), 6.53-6.80 (2H, m), 7.01 (1H, d, J=8.3 Hz).

(2) The compound (3.89 g) obtained in the above-mentioned (1) was dissolved in formic acid (9.7 ml), and 10M hydrogen chloride-2-propanol solution (2.28 ml) was added under ice-cooling. The mixture was stirred at room temperature for 35 min and the reaction mixture was poured into a mixture (200 ml) of diisopropyl ether-n-hexane (1:1) under ice-cooling. The resulting oil was separated by decantation and dissolved in ethyl acetate (100 ml). Water (100 ml) was added, and neutralized with sodium bicarbonate. Two layers were separated, and ethyl acetate layer was washed successively with water and saturated brine (50 ml each), and dried (Na$_2$SO$_4$). Ethyl acetate was evaporated under reduced pressure to give the title compound (3.07 g).

IR ν (neat) cm$^{-1}$; 3344, 2951, 2870, 2777, 2740, 1659, 1643, 1612, 1504.

$^1$H-NMR (CDCl$_3$) δ (ppm); 1.20-1.97 (8H, m), 1.99 (1H, s), 2.27 (3H, s), 2.30-2.77 (1H, m), 2.86 (2H, t, J=6.7 Hz), 2.80-3.10 (2H, m), 3.60-3.83 (1H, m), 3.76 (3H, s), 3.95-4.34 (4H, m), 6.15 (1H, d, J=16.0 Hz), 6.41-6.80 (3H, m), 6.99 (1H, d, J=8.4 Hz).

Example 22 tert-butylamine 7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylate (1) The compound (3.05 g) obtained in Example 21 was dissolved in methylene chloride (30 ml), and sorbic acid chloride (1.12 g) and triethylamine (1.35 ml) were added under ice-cooling. The mixture was stirred at the same temperature for 20 min. The reaction mixture was washed with 10% aqueous citric acid solution and saturated brine (each 20 ml), and dried (Na$_2$SO$_4$). Methylene chloride was evaporated under reduced pressure, and the obtained residue was purified by silica gel column chromatography to give methyl 7-(2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylate (2.49 g).

IR ν (neat) cm$^{-1}$; 3464, 2953, 2870, 1740, 1657, 1628, 1605, 1506.

$^1$H-NMR (CDCl$_3$) δ (ppm); 1.20-1.97 (8H, m), 1.85 (3H, d, J=4.8 Hz), 2.27 (3H, s), 2.40-2.75 (1H, m), 2.86 (2H, t, J=6.5 Hz), 3.00-3.22 (2H, m), 3.59 (3H, s), 4.14 (2H, t, J=6.5 Hz), 4.36-5.00 (2H, m), 5.40-5.60 (1H, m), 6.07-6.80 (5H, m), 6.15 (1H, d, J=16.1 Hz), 6.61 (1H, dd, J=16.1, 7.2 Hz), 7.03 (1H, d, J=8.4 Hz), 7.13-7.50 (1H, m).

(2) The compound (2.48 g) obtained in the above-mentioned (1) was dissolved in a mixture (60 ml) of tetrahydrofuran-methanol (3:1), and 1M aqueous lithium hydroxide solution (14.7 ml) was added. The mixture was stirred at room temperature for 50 min and acidified with 6M hydrochloric acid. The solution was concentrated under reduced pressure and the precipitated gummy material was extracted with ethyl acetate (30 ml). The ethyl acetate layer was washed with saturated brine (30 ml), and dried (Na$_2$SO$_4$). Ethyl acetate was evaporated under reduced pressure and the obtained residue was dissolved in methanol (2.4 ml). After dropwise addition of tert-butylamine (1.0 ml), diisopropyl ether (30 ml) was added, and the mixture was stirred under ice-cooling for 1 h 20 min. The precipitated crystals were collected by filtration to give the title compound (2.41 g).

IR ν (Nujol) cm$^{-1}$; 2731, 2631, 2544, 1653, 1626, 1553, 1506.

$^1$H-NMR (CDCl$_3$) δ (ppm); 0.99 (9H, s), 1.20-2.05 (11H, m), 2.27 (3H, s), 2.38-2.73 (1H, m), 2.85 (2H, t, J=6.5 Hz), 2.90-3.40 (2H, m), 4.10 (2H, t, J=6.5 Hz), 4.26-5.20 (3H, m), 5.86-7.38 (12H, m).

Example 23 methyl 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 2955, 2928, 2872, 1740, 1661, 1622, 1533, 1506.

$^1$H-NMR (CDCl$_3$) δ (ppm); 0.75-2.15 (3H, m), 0.94 (6H, d, J=6.4 Hz), 1.20-2.00 (5H, m), 2.20-2.45 (2H, m), 2.11 (2H, t, J=6.6 Hz), 2.28 (3H, s), 2.87 (2H, t, J=6.8 Hz), 3.00-3.325 (2H, m), 3.60 (3H, s), 4.15 (2H, t, J=6.8 Hz), 4.40-5.60 (3H, m), 6.16 (1H, d, J=16.0 Hz), 6.35-7.20 (6H, m).

Example 24 tert-butylamine-2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 1661, 1616, 1558, 1506.

$^1$H-NMR (CDCl$_3$) δ (ppm); 0.75-2.20 (3H, m), 0.93 (6H, d, J=6.4 Hz), 1.02 (9H, s), 1.20-1.60 (4H, m), 1.60-1.95 (1H, m), 1.95-2.30 (2H, m), 2.10 (2H, t, J=6.6 Hz), 2.28 (3H, s), 2.86 (2H, t, J=6.8 Hz), 3.00-3.40 (2H, m), 4.10 (2H, t, J=6.8 Hz), 4.40-5.20 (3H, m), 6.15 (1H, d, J=16.1 Hz), 6.10-7.20 (9H, m).

Example 25 methyl 7-{2-[2-(trans-1-hexen-1-yl)-5-methyloxazol-4-yl]ethoxy}-1,2,3,4-tetrahydroisoquinoline-(3S)-carboxylate IR ν (neat) cm$^{-1}$; 3346, 2955, 2928, 2872, 1742, 1661, 1612, 1504.

$^1$H-NMR (CDCl$_3$) δ (ppm); 0.72-1.06 (3H, m), 1.06-1.65 (4H, m), 1.96-2.40 (3H, m), 2.27 (3H, s), 2.80-3.02 (2H, m), 2.86 (2H, t, J=6.7 Hz), 3.57-3.74 (1H, m), 3.76 (3H, s), 3.91-4.10 (2H, m), 4.14 (2H, t, J=6.7 Hz), 6.16 (1H, d, J=16.0 Hz), 6.39-6.79 (3H, m), 6.99-(1H, d, J=7.5 Hz).

Example 26 methyl 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylate IR ν (neat) cm$^{-1}$; 3468, 3020, 2957, 2930, 2872, 1740, 1657, 1629, 1605, 1506.

$^1$H-NMR (CDCl$_3$) δ (ppm); 0.75-1.07 (3H, m), 1.20-1.60 (4H, m), 1.85 (3H, d, J=5.0 Hz), 2.08-2.40 (2H, m), 2.27 (3H, s), 2.87 (2H, t, J=6.6 Hz), 3.00-3.25 (2H, m), 3.60 (3H, s), 4.15 (2H, t, J=6.6 Hz), 4.35-5.10 (2H, m), 5.52 (1H, br-t), 5.96-6.84 (7H, m), 7.01 (1H, d, J=8.4 Hz), 7.15-7.50 (1H, m).

Example 27 tert-butylamine 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylate IR ν (Nujol) cm⁻¹; 3400, 2745, 2637, 2548, 2220, 1651, 1626, 1556, 1506.
¹H-NMR (CDCl₃) δ (ppm); 0.75-1.16 (3H, m), 0.98 (9H, s), 1.20-1.60 (4H, m), 1.70-2.00 (3H, m), 2.07-2.40 (2H, m), 2.27 (3H, 30 s), 2.86 (2H, t, J=6.5 Hz), 2.88-3.30 (2H, m), 4.11 (2H, t, J=6.5 Hz), 4.25-5.20 (3H, m), 5.90-7.40 (12H, m).

Example 28 methyl 7-{2-[5-methyl-2-(5-methyl-trans-1-hexen-1-yl)oxazol-4-yl]ethoxy}-1,2,3,4-tetrahydroisoquinoline-(3S)-carboxylate IR ν (neat) cm⁻¹; 3346, 2953, 2926, 2870, 2849, 1742, 1641, 1612, 1533, 1504.
¹H-NMR (CDCl₃) δ (ppm); 0.90 (6H, d, J=6.1 Hz), 1.15-1.73 (3H, m), 1.86 (1H, br-s), 2.04-2.40 (2H, m), 2.27 (3H, s), 2.86 (2H, t, J=6.6 Hz), 2.90-3.06 (2H, m), 3.55-3.75 (1H, m), 3.77 (3H, s), 3.90-4.10 (2H, m), 4.22 (2H, t, J=6.6 Hz), 6.17 (1H, d, J=16.0 Hz), 6.39-6.81 (3H, m), 6.99 (1H, d, J=8.3 Hz).

Example 29 methyl 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylate IR ν (neat) cm⁻¹; 3462, 2955, 2928, 2870, 1740, 1653, 1630, 1533, 1506.
¹H-NMR (CDCl₃) δ (ppm); 0.90 (6H, d, J=6.2 Hz) 1.14-1.72 (3H, m), 1.86 (3H, d, J=5.0 Hz), 2.05-2.40 (2H, m), 2.27 (3H, s), 2.87 (2H, t, J=6.6 Hz, ), 3.00-3.25 (2H, m), 3.60 (3H, s), 4.15 (2H, t, J=6.6 Hz), 4.39-5.20 (2H, m), 5.42-5.65 (1H, m), 6.00-6.87 (7H, m), 7.04 (1H, d, J=8.1 Hz), 7.18-7.51 (1H, m).

Example 30 tert-butylamine 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylate IR ν (Nujol) cm⁻¹; 3400, 2735, 2635, 2550, 1657, 1634, 1558, 1506.
¹H-NMR (CDCl₃) δ (ppm); 0.90 (6H, d, J=6.3 Hz), 0.97 (9H, s), 1.20-1.70 (3H, m), 1.70-1.98 (3H, m), 2.06-2.40 (2H, m), 2.27 (3H, s), 2.86 (2H, t, J=6.4 Hz), 2.90-3.25 (2H, m), 4.10 (2H, t, J=6.4 Hz), 4.25-5.20 (3H, m), 5.72-7.38 (12H, m).

Example 31 methyl 7-{2-[5-methyl-2-(1-methyl-trans-1-penten-1-yl)oxazol-4-yl]ethoxy}-1,2,3,4-tetrahydroisoquinoline-(3S)-carboxylate IR ν (neat) cm⁻¹; 3344, 2957, 2930, 2872, 1742, 1647, 1612, 1504.
¹H-NMR (CDCl₃) δ (ppm); 0.95 (3H, t, J=7.2 Hz), 1.20-1.72 (2H, m), 2.02 (3H, s), 2.03-2.30 (3H, m), 2.27 (3H, s), 2.88 (2H, t, J=6.8 Hz), 2.90-3.10 (2H, m), 3.60-3.80 (1H, m), 3.76 (3H, s), 4.05 (2H, s), 4.14 (2H, t, J=6.8 Hz), 6.30-6.80 (3H, m), 6.99 (1H, d, J=8.4 Hz).

Example 32 methyl 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylate IR ν (neat) cm⁻¹; 3462, 2957, 2930, 2872, 1740, 1655, 1628, 1612, 1533, 1506.
¹H-NMR (CDCl₃) δ (ppm); 0.95 (3H, t, J=7.0 Hz), 1.20-1.75 (2H, m) 1.86 (3H, d, J=5.0 Hz), 2.00-2.30 (2H, m), 2.04 (3H, s), 2.28 (3H, s), 2.89 (2H, t, J=6.5 Hz), 3.02-3.25 (2H, m), 3.60 (3H, s), 4.15 (2H, t, J=6.5 Hz), 4.36-5.00 (2H, m), 5.50 (1H, br-t), 5.92-6.85 (6H, m), 7.03 (1H, d, J=8.1 Hz), 7.15-7.53 (1H, m).

Example 33 tert-butylamine 2-(2,4-hexadienoyl)-7-(2-[5-methyl-2-(1-methyl-trans-1-penten-1-yl)oxazol-4-yl]ethoxy}-1,2,3,4-tetrahydroisoquinoline-(3S)-carboxylate IR ν (Nujol) cm⁻¹; 2748, 2637, 2544, 2220, 1651, 1624, 1600, 1553.
¹H-NMR (CDCl₃) δ (ppm); 0.80-1.08 (3H, m), 0.97 (9H, s), 1.11-1.70 (2H, m), 1.70-1.93 (3H, m), 1.93-2.35 (2H, m), 2.01 (3H, s), 2.27 (3H, s), 2.87 (2H, t, J=6.7 Hz), 2.90-3.40 (2H, m), 4.10 (2H, t, J=6.7 Hz), 4.24-5.20 (3H, m), 5.92-7.38 (11H, m).

Example 34 methyl 7-{2-[5-methyl-2-(1-methyl-trans-1-buten-1-yl)oxazol-4-yl]ethoxy}-1,2,3,4-tetrahydroisoquinoline-(3S)-carboxylate IR ν (neat) cm⁻¹; 2956, 2932, 2875, 1739, 1646, 1611, 1582, 1533, 1505.
¹H-NMR (CDCl₃) δ (ppm); 1.06 (3H, t, J=7.5 Hz), 2.01 (3H, s), 2.10-2.45 (3H, m), 2.27 (3H, s), 2.70-3.20 (4H, m), 3.55-3.90 (1H, m), 3.76 (3H, s), 4.05 (2H, s), 4.14 (2H, t, J=6.8 Hz), 6.25-6.85 (3H, m), 6.99 (1H, d, J=8.6 Hz).

Example 35 methyl 2-(2,4-hexadienoyl)-7-{2-[5-methyl-2-(1-methyl-trans-1-buten-1-yl) oxazol-4-yl]ethoxy}-1,2,3,4-tetrahydroisoquinoline-(3S)-carboxylate.

IR ν (neat) cm⁻¹; 2961, 2933, 2875, 1739, 1652, 1627, 1606, 1534, 1506.
¹H-NMR (CDCl₃) δ (ppm); 1.06 (3H, t, J=7.5 Hz), 1.85 (3H, d, J=5.0 Hz), 2.01 (3H, s), 2.05-2.45 (2H, m), 2.28 (3H, s), 2.89 (2H, t, J=6.4 Hz), 3.00-3.40 (2H, m), 4.15 (2H, t, J=6.4 Hz) 4.30-5.65 (3H, m), 7.03 (1H, d, J=8.4 Hz), 5.90-7.60 (7H, m).

Example 36 tert-butylamine 2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylate IR ν (Nujol) cm$^{-1}$; 2733, 2635, 2550, 1657, 1634, 1611, 1558, 1506.
$^1$H-NMR (CDCl$_3$) δ (ppm); 0.99 (9H, s), 1.05 (3H, t, J=7.5 Hz) 1.65-1.95 (3H, m), 2.01 (3H, s), 2.05-2.45 (2H, m), 2.28 (3H, s), 2.87 (2H, t, J=6.7 Hz), 2.90-3.30 (2H, m), 4.11 (2H, t, J=6.7 Hz), 4.25-5.20 (3H, m), 0.5.90-8.30 (12H, m).

Example 37

7-{2-[5-methyl-2-(trans-1-penten-1-yl)oxazol-4-yl]ethoxy}-2-(2,2,3,3,3-pentafluoropropionyl)-1,2,3,4-tetrahydroisoquinoline-(3S)-carboxylic acid IR ν (Nujol) cm$^{-1}$; 2725, 2509, 1917, 1732, 1682, 1614, 1589, 1531.
$^1$H-NMR (CDCl$_3$) δ (ppm); 0.93 (3H, t, J=7.1 Hz), 1.20-1.70 (2H, m), 2.00-2.38 (2H, m), 2.23 (3H, s), 2.59-2.87 (2H, m), 2.91-3.52 (2H, m), 3.64-4.00 (2H, m), 4.21-5.03 (2H, m), 5.03-5.47 (1H, m), 6.18 (1H, d, J=16.3 Hz), 6.42-6.85 (3H, m), 7.05 (1H, d, J=8.4 Hz), 7.14-7.68 (1H, br).

Example 38 methyl 7-{2-[2-(trans-2-cyclohexylvinyl)-5-methyloxazol-4-yl]ethoxy}-1,2,3,4-tetrahydroisoquinoline-(3S)-carboxylate IR ν (neat) cm$^{-1}$; 2926, 2851, 1740, 1641, 1612, 1582, 1533, 1504.
$^1$H-NMR (CDCl$_3$) δ (ppm); 0.80-2.45 (11H, m), 2.27 (3H, s), 2.70-3.20 (2H, m), 2.86 (2H, t, J=7.0 Hz), 3.55-3.85 (1H, m), 3.76 (3H, s), 4.04 (2H, s), 4.14 (2H, t, J=6.8 Hz), 6.12 (1H, d, J=16.0 Hz), 6.40-6.80 (3H, m), 6.99 (1H, d, J=8.4 Hz).

Example 39 methyl 7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 1745, 1614, 1531, 1506.
$^1$H-NMR (CDCl$_3$) δ (ppm); 0.85-2.45 (14H, m), 2.27 (3H, s), 2.87 (2H, t, J=6.8 Hz), 3.00-3.35 (2H, m), 3.59 (3H, s), 4.15 (2H, t, J=6.8 Hz), 4.30-5.65 (3H, m), 6.00-7.55 (7H, m), 6.50 (1H, d, J=6.4 Hz), 7.03 (1H, d, J=8.4 Hz).

Example 40 tert-butylamine 7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 2739, 2635, 2548, 1655, 1630, 1560, 1506.
$^1$H-NMR (CDCl$_3$) δ (ppm); 0.98 (9H, s), 1.00-2.40 (14H, m), 2.27 (3H, s), 2.85 (2H, t, J=6.8 Hz), 2.90-3.30 (2H, m), 4.10 (2H, t, J=6.8 Hz), 4.20-5.20 (3H, m), 5.80-7.45 (12H, m).

Example 41

2-cinnamoyl-7-[2-(5-methyl-2-(trans-1-penten-1-yl)oxazol-4-yl)ethoxy]-1,2,3,4-tetrahydroisoquinoline-(3S)-carboxylic acid IR ν (Nujol) cm$^{-1}$; 1728, 1647, 1612, 1578, 1533, 1506.
$^1$H-NMR (DMSO-d$_6$) δ (ppm); 0.89 (3H, t, J=7.3 Hz), 1.20-1.70 (2H, ), 1.95-2.25 (2H, m), 2.26 (3H, s), 2.65-2.95 (2H, m), 2.95-3.15 (2H, m), 3.60-5.80 (1H, br), 3.95-4.35 (2H, m), 4.40-5.60 (3H, m), 6.19 (1H, d, J=16.5 Hz), 6.33-6.90 (3H, m), 7.11 (1H, d, J=8.4 Hz), 7.30-7.95 (7H, m).

Example 42 tert-butylamine 7-{2-[2-(3-ethyl-trans-1-penten-1-yl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 2735, 2633, 2544, 1653, 1624, 1599, 1551, 1506.
$^1$H-NMR (CDCl$_3$) δ (ppm); 0.87 (6H, t, J=7.2 Hz), 0.96 (9H, s), 1.20-1.63 (4H, m), 1.63-2.10 (4H, m), 2.28 (3H, s), 2.86 (2H, t, J=6.8 Hz), 2.90-3.30 (2H, m), 4.11 (2H, t, J=6.8 Hz), 4.40-5.30 (3H, m), 5.80-7.60 (12H, m).

Example 43 tert-butylamine 7-{2-[2-(3,3-dimethyl-trans-1-buten-1-yl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 3568, 2745, 2637, 2216, 1653, 1553.
$^1$H-NMR (CDCl$_3$) δ (ppm); 0.97 (18H, s), 1.60-2.00 (3H, m), 2.28 (3H, s), 2.86 (2H, t, J=6.5 Hz), 2.90-3.35 (2H, m), 4.11 (2H, t, J=6.5 Hz), 4.28-5.20 (3H, m), 5.90-7.48 (12H, m).

Example 44 tert-butylamine 7-{2-[2-(3,3-dimethyl-trans-1-penten-1-yl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 3400, 2745, 2635, 2544, 2220, 1651, 1622, 1553.
$^1$H-NMR (CDCl$_3$) δ (ppm); 0.82 (3H, t, J=7.3 Hz), 0.98 (9H, s), 1.05 (6H, s), 1.41 (2H, q, J=7.3 Hz), 1.63-1.94 (3H, m), 2.28 (3H, s), 2.86 (2H, t, J=6.8 Hz), 2.90-3.37 (2H, m), 4.11 (2H, t, J=6.8 Hz), 4.23-5.20 (3H, m), 6.09 (1H, d, J=16.3 Hz), 6.00-7.39 (11H, m).

Example 45 tert-butylamine 7-{2-[2-(4,4-dimethyl-trans-1-penten-1-yl)-5-methyloxazol-4-yl]ethoxy)-2-(2,4-hexadienoyl)-1,2,3,4-tetrahydroisoquinoline-(3S)-carboxylate IR ν (Nujol) cm$^{-1}$; 2733, 2635, 2550, 1657, 1634, 1611, 1558, 1506.
$^1$H-NMR (CDCl$_3$) δ (ppm); 0.94 (9H, s), 1.01 (9H, s), 1.65-1.95 (3H, m), 2.09 (2H, d, J=7.5 Hz). 2.28 (3H, s), 2.86

(2H, t, J=6.6 Hz), 2.90-3.30 (2H, m), 4.11 (2H, t, J=6.6 Hz), 4.25-5.20 (3H, m), 5.90-7.35 (12H, m).

Example 46 tert-butylamine 2-(2,4-hexadienoyl)-7-{2-[5-methyl-2-(3-methyl-trans-1-buten-1-yl)oxazol-4-yl)ethoxy}-1,2,3,4-tetrahydroisoquinoline-(3S)-carboxylate IR ν (Nujol) cm$^{-1}$; 2741, 2633, 2544, 1651, 1622, 1553, 1506.
$^1$H-NMR (CDCl$_3$) δ (ppm); 1.01 (9H, s), 1.08 (6H, d, J=6.7 Hz) 1.65-1.95 (3H, m), 2.28 (3H, s), 2.35-2.70 (1H, m), 2.86 (2H, t, J=6.6 Hz), 2.85-3.30 (2H, m), 4.11 (2H, t, J=6.6 Hz), 4.25-5.20 (3H, m), 5.85-8.00 (12H, m).

Example 47 tert-butylamine 2-(5-methyl-2-hexenoyl)-7-(2-[5-methyl-2-(trans-1-penten-1-yl)oxazol-4-yl]ethoxy}-1,2,3,4-tetrahydroisoquinoline-(3S)-carboxylate IR ν (Nujol) cm$^{-1}$; 3398, 2741, 2635, 2548, 1661, 1614, 1553.
$^1$H-NMR (CDCl$_3$) δ (ppm); 0.70-1.14 (18H, m), 1.14-2.20 (7H, m) 2.27 (3H, s), 2.85 (2H, br-t), 2.90-3.40 (2H, m), 4.10 (2H, br-t), 4.40-5.20 (3H, m), 5.80-7.10 (10H, m).

Example 48 tert-butylamine 2-(4,4-dimethyl-2-penthenoyl)-7-{2-[5-methyl-2-(trans-1-penten-1-yl)oxazol-4-yl]ethoxy}-1,2,3,4-tetrahydroisoquinoline-(3S)-carboxylate IR ν (Nujol) cm$^{-1}$; 2741, 2633, 1622, 1556, 1504.
$^1$H-NMR (CDCl$_3$) δ (ppm); 0.94 (3H, t, J=7.5 Hz), 1.05 (9H, s), 1.10 (9H, s), 1.20-1.70 (2H, m), 2.05-2.45 (2H, m), 2.28 (3H, s), 2.86 (2H, t, J=6.3 Hz), 2.95-3.30 (2H, m), 4.11 (2H, t, J=6.3 Hz), 4.30-5.20 (3H, m), 5.00-6.00 (3H, br), 6.00-7.20 (7H, m).

Example 49 tert-butylamine 2-(2,4-hexadienoyl)-7-{2-[5-methyl-2-(trans-2-thiophen-2-ylvinyl)oxazol-4-yl]ethoxy}-1,2,3,4-tetrahydroisoquinoline-(3S)-carboxylate IR ν (Nujol) cm$^{-1}$; 0.3420, 2737, 2633, 2548, 1651, 1622, 1558, 1504.
$^1$H-NMR (CDCl$_3$) δ (ppm); 0.97 (9H, s), 1.83 (3H, br-d), 2.31 (3H, s), 2.89 (2H, t, J=6.3 Hz), 2.90-3.23 (2H, m), 4.13 (2H, t, J=6.3 Hz), 4.30-5.20 (3H, m), 6.00-6.78 (10H, m), 6.85-7.37 (2H, m), 7.49 (1H, d, J=16.4 Hz).

Example 50

2-(2-heptenoyl)-7-{2-[5-methyl-2-phenylsulfanyloxazol-4-yl]ethoxy}-1,2,3,4-tetrahydroisoquinoline-(3S)-carboxylic acid IR ν (Nujol) cm$^{-1}$; 2571, 1732, 1657, 1614, 1583, 1506.
$^1$H-NMR (CDCl$_3$) δ (ppm); 0.91 (3H, br-t), 1.10-1.70 (4H, m), 2.82 (2H, t, J=6.8 Hz), 1.90-2.40 (2H, m), 2.22 (3H, s), 2.95-3.40 (2H, m), 4.07 (2H, t, J=6.8 Hz), 4.20-5.65 (3H, m), 6.32 (1H, d, J=16.2 Hz), 6.50-6.85 (4H, m), 7.04 (1H, d, J=7.7 Hz), 7.20-7.65 (5H, m).

Example 51 tert-butylamine 2-(2,4-hexadienoyl)-7-{2-[2-(trans-1-penten-1-yl)-5-propyloxazol-4-yl]ethoxy}-1,2,3,4-tetrahydroisoquinoline-(3S)-carboxylate IR ν (Nujol) cm$^{-1}$; 2731, 2633, 2546, 1630, 1553, 1504.
$^1$H-NMR (CDCl$_3$) δ (ppm); 0.91 (6H, t, J=7.0 Hz), 0.96 (9H, s), 1.25-2.00 (7H, m), 2.20 (2H, q, J=7.0 Hz), 2.60 (2H, t, J=7.0 Hz), 2.87 (2H, t, J=6.6 Hz), 2.90-3.30 (2H, m), 4.11 (2H, t, J=6.6 Hz), 4.25-5.20 (3H, m), 5.80-7.40 (12H, m).

Example 52 tert-butylamine 2-(2,2-difluorobutyryl)-7-{2-[5-methyl-2-(trans-1-penten-1-yl)oxazol-4-yl]ethoxy}-1,2,3,4-tetrahydroisoquinoline-(3S)-carboxylate IR ν (Nujol) cm$^{-1}$; 2745, 2638, 2552, 1661, 1614, 1564, 1506.
$^1$H-NMR (CDCl$_3$) δ (ppm); 0.75-2.20 (6H, m), 1.25-1.70 (2H, m), 1.85-2.45 (4H, m), 0.93 (9H, s), 1.26-2.70 (11H, m), 2.27 (3H, s), 2.86 (2H, t, J=6.6 Hz), 2.95-3.25 (2H, m), 4.11 (2H, t, J=6.6 Hz), 4.30-5.15 (3H, m), 6.17 (1H, d, J=16.3 Hz), 6.35-7.50 (7H, m).

Example 53 tert-butylamine 2-(4,4-difluoropentanoyl)-7-{2-[5-methyl-2-(trans-1-penten-1-yl)oxazol-4-yl]ethoxy}-1,2,3,4-tetrahydroisoquinoline-(3S)-carboxylate IR ν (Nujol) cm$^{-1}$; 3398, 2745, 2637, 2550, 1645, 1556.
$^1$H-NMR (CDCl$_3$) δ (ppm); 0.95 (3H, t, J=7.5 Hz), 0.99 (3H, s) 1.26-2.70 (11H, m), 2.28 (3H, s), 2.86 (2H, br-t), 3.00-3.41 (2H, m), 4.11 (2H, br-t), 4.36-4.70 (2H, m), 4.80-5.10 (1H, m), 5.57-6.14 (3H, br), 6.16 (1H, d, J=16.3 Hz), 6.41-6.80 (3H, m), 6.83-7.08 (1H, m).

Example 54

7-{2-[5-methyl-2-(trans-1-penten-1-yl)oxazol-4-yl]ethoxy}-2-(3,3,3-trifluoropropionyl)-1,2,3,4-tetrahydroisoquinoline-(3S)-carboxylic acid IR ν (Nujol) cm$^{-1}$; 2723, 2621, 1732, 1661, 1614, 1506.
$^1$H-NMR (CDCl$_3$) δ (ppm); 0.95 (3H, t, J=7.5 Hz), 1.20-1.75 (2H, m), 2.23 (2H, t, J=6.8 Hz), 2.34 (3H, s), 2.94 (2H, br-t), 3.00-3.60 (4H, m), 4.09 (2H, br-t), 4.30-5.50 (3H, —m), 6.36 (1H, d, J=16.0 Hz), 7.04 (1H, d, J=7.7 Hz), 6.50-6.95 (3H, m), 8.93 (1H, br-s).

Example 55 tert-butylamine 2-(2,4-hexadienoyl)-7-{2-[5-methyl-2-(2-methylsulfanylethyl)oxazol-4-yl]ethoxy}-1,2,3,4-tetrahydroisoquinoline-(3S)-carboxylate IR ν (Nujol) cm$^{-1}$; 2745, 2637, 2548, 1651, 1624, 1601, 1553, 1504.
$^1$H-NMR (CDCl$_3$) δ (ppm); 0.97 (9H, s), 1.65-2.00 (3H, m), 2.11 (3H, s), 2.25 (3H, s), 2.70-5.40 (6H, m), 2.85 (2H, t, J=6.8 Hz), 4.10 (2H, t, J=6.8 Hz), 4.25-5.20 (3H, m), 5.80-7.40 (12H, m).

Example 56 tert-butylamine 2-(2,4-hexadienoyl)-7-(2-{5-methyl-2-[2-trans-(1-methylcyclohexen-1-yl)vinyl]oxazol-4-yl}ethoxy)-1,2,3,4-tetrahydroisoquinoline-(3S)-carboxylate IR ν (Nujol) cm$^{-1}$; 2739, 2631, 2548, 1651, 1622, 1599, 1585, 1547, 1508.

$^1$H-NMR (CDCl$_3$) δ (ppm); 0.97 (9H, s), 1.05 (3H, s), 1.15-2.00 (13H, m), 2.28 (3H, s), 2.86 (2H, t, J=6.6 Hz), 2.90-3.40 (2H, m), 4.11 (2H, t, J=6.6 Hz), 4.25-5.20 (3H, m), 5.85-7.50 (12H, m).

Example 57 tert-butylamine 2-(2,4-hexadienoyl)-7-(2-{5-methyl-2-[2-trans-(1-methylcyclopentan-1-yl)vinyl]oxazol-4-yl]ethoxy)-1,2,3,4-tetrahydroisoquinoline-(3S)-carboxylate IR ν (Nujol) cm$^{-1}$; 2739, 2633, 2544, 1634, 1549, 1504.

$^1$H-NMR (CDCl$_3$) δ (ppm); 0.99 (9H, s), 1.14 (3H, s), 1.30-2.05 (11H, m), 2.28 (3H, s), 2.86 (2H, t, J=6.8 Hz), 2.90-3.40 (2H, m), 4.11 (2H, t, J=6.8 Hz), 4.25-5.20 (3H, m), 5.80-7.45 (12H, m).

Example 58

7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid (1) Methyl 7-(2-[5-methyl-2-(4-methyl-trans-1-penten-1-yl)oxazol-4-yl]ethoxy}-1,2,3,4-tetrahydroisoquinoline-(3S)-carboxylate (1.0 g) was dissolved in N,N-dimethylformamide (10 ml), and triethylamine (1.4 ml) and 5-bromo-1-pentene (1.2 ml) were added. The mixture was stirred at room temperature for 40 h, and triethylamine (1.05 ml) and 5-bromo-1-pentene (0.89 ml) were added. The mixture was further stirred for 26 h. Ethyl acetate (20 ml) was added, and the mixture was washed twice with water (50 ml), 10%-aqueous citric acid solution and saturated brine (10 ml each), and dried (Na$_2$SO$_4$). Ethyl acetate was evaporated under reduced pressure and the obtained residue was purified by silica gel column chromatography to give methyl 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylate as an oil (0.89 g).

IR ν (neat) cm$^{-1}$; 3449, 2953, 2928, 2870, 1738, 1641, 1614, 1533, 1506.

$^1$H-NMR (CDCl$_3$) δ (ppm); 0.94 (6H, d, J=6.3 Hz), 1.40-1.90 (3H, m), 1.90-2.33 (4H, m), 2.27 (3H, s), 2.50-3.17 (6H, m), 3.65 (3H, s), 3.70-4.25 (5H, m), 4.80-5.13 (2H, m), 5.45-6.00 (1H, m), 6.16 (1H, d, J=16.0 Hz), 6.36-6.79 (3H, m), 6.97 (1H, d, J=8.4 Hz).

(2) The compound (0.8 g) obtained in the above-mentioned (1) was dissolved in a mixture (23 ml) of tetrahydrofuran-methanol. (3:1), and 1M aqueous lithium hydroxide solution (5.66 ml) was added. The mixture was stirred for at room temperature 40 min and acidified with 10% aqueous citric acid solution. The solution was concentrated under reduced pressure and the precipitated gummy material was extracted with ethyl acetate (20 ml). The ethyl acetate layer was washed with saturated brine (20 ml) and dried (Na$_2$SO$_4$). Ethyl acetate was evaporated under reduced pressure and n-hexane was added to the residue. The precipitated crystals were collected by filtration to give the title compound (0.74 g).

IR ν (Nujol) cm$^{-1}$; 3400, 3057, 2725, 2664, 2565, 2494, 1626, 1551, 1508.

$^1$H-NMR (CDCl$_3$) δ (ppm); 0.93 (6H, d, J=6.4 Hz), 1.48-2.30 (7H, m), 2.28 (3H, s), 2.60-3.33 (6H, m), 3.72 (1H, br-t), 3.82-4.46 (4H, m), 4.80-5.20 (2H, m), 5.42-5.97 (1H, m), 6.15 (1H, d, J=16.1 Hz), 6.40-6.90 (3H, m), 7.08 (1H, d, J=8.4 Hz), 8.55-9.05 (1H, br).

Example 59

2-benzyl-7-{2-[5-methyl-2-(4-methyl-trans-1-penten-1-yl)oxazol-4-yl]ethoxy}-1,2,3,4-tetrahydroisoquinoline-(3S)-carboxylic acid (1) Methyl 2-benzyl-7-hydroxy-1,2,3,4-tetrahydroisoquinoline-3(S)-carboxylate (483 mg) and 2-[5-methyl-2-(4-methyl-trans-1-penten-1-yl)oxazol-4-yl]ethyl methanesulfonate (700 mg) were dissolved in toluene (15 ml), and potassium carbonate (674 mg) and tetraethylammonium fluoride hydrate (100 mg) were added. The mixture was stirred at 90° C. for 18 h. To the reaction mixture was added ethyl acetate (10 ml), and the mixture was washed successively with water (20 ml) and saturated brine (20 ml), and dried (Na$_2$SO$_4$). The solvent was evaporated under reduced pressure and the obtained residue was purified by silica gel column chromatography to give methyl 2-benzyl-7-{2-[5-methyl-2-(4-methyl-trans-1-penten-1-yl)oxazol-4-yl]ethoxy}-1,2,3,4-tetrahydroisoquinoline-(3S)-carboxylate (590 mg).

IR ν (neat) cm$^{-1}$; 3443, 3027, 2953, 2926, 2871, 2841, 1739, 1613, 1534, 1505.

$^1$H-NMR (CDCl$_3$) δ (ppm); 0.93 (6H, d, J=6.4 Hz), 1.48-2.00 (1H, m), 2.10 (2H, t, J=6.8 Hz), 2.26 (3H, s), 2.84 (2H, t, J=6.8 Hz), 3.08 (2H, d, J=4.6 Hz), 3.66 (3H, s), 3.70-4.30 (5H, m), 3.90 (2H, s), 6.15 (1H, d, J=16.1 Hz), 6.38-6.78 (3H, m), 6.98 (1H, d, J=8.2 Hz), 7.16-7.50 (5H, m).

(2) The compound of (1) (570 mg) obtained in the above-mentioned (1) was dissolved in a mixture (14 ml) of tetrahydrofuran-methanol (3:1), and 1M aqueous lithium hydroxide solution (3.5 ml) was added. The mixture was stirred at 40° C. for 1.5 h and acidified with 6M hydrochloric acid. The solution was concentrated under reduced pressure and the precipitated gummy material was extracted with ethyl acetate (15 ml). The ethyl acetate layer was washed with saturated brine (10 ml) and dried (Na$_2$SO$_4$). Ethyl acetate was evaporated under reduced pressure and n-hexane was added to the obtained residue. The mixture was stirred under ice-cooling for 30 min, and the precipitated crystals were collected by filtration to give the title compound (445 mg).

IR ν (Nujol) cm$^{-1}$; 3385, 3047, 1718, 1636, 1585, 1549, 1533, 1501.

$^1$H-NMR (CDCl$_3$) δ (ppm), 0.93 (6H, d, J=6.4 Hz), 1.46-1.99 (1H, m), 2.10 (2H, t, J=6.7 Hz), 2.27 (3H, s), 2.85 (2H, t, J=6.8 Hz), 3.19 (2H, d, J=6.1 Hz), 3.63-4.40 (5H, m), 4.03 (2H, s), 6.15 (1H, d, J=15.8 Hz), 0.6.36-6.85 (3H, m), 7.06 (1H, d, J=8.6 Hz), 7.20-7.60 (5H, m), 9.37 (1H, br-s).

Example 60

2-benzyl-7-{2-[2-(3,3-dimethyl-trans-1-buten-1-yl)-5-methyloxazol-4-yl]ethoxy}-1,2,3,4-tetrahydroisoquinoline-(3S)-carboxylic acid IR ν (Nujol) cm$^{-1}$; 3420, 1680, 1614, 1506.
$^1$H-NMR (DMSO-d$_6$) δ (ppm); 1.07 (9H, s), 2.23 (3H, s), 2.77 (2H, t, J=6.3 Hz), 2.80-3.10 (2H, m), 3.20-4.60 (8H, m), 6.07 (1H, d, J=16.5 Hz), 6.59 (1H, d, J=16.5 Hz), 6.40-6.80 (2H, m), 7.01 (1H, J=8.4 Hz), 7.32 (5H, br-s).

Example 61 tert-butylamine 2-(2,2-dimethylpropyl)-7-{2-[5-methyl-2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 3398, 2746, 2637, 2554, 1641, 1612, 1543.
$^1$H-NMR (CDCl$_3$) δ (ppm); 0.87 (9H, s), 0.93 (6H, d, J=6.6 Hz) 1.02 (9H, s), 1.48-2.00 (1H, m), 2.11 (2H, t, J=6.8 Hz), 2.28 (3H, s), 2.48 (2H, d, J=7.9 Hz), 2.60-3.20 (2H, m), 2.86 (2H, t, J=6.8 Hz), 3.30-3.53 (1H, m), 4.00 (2H, dd, J=16.6 Hz, 52.7 Hz), 4.11 (2H, t, J=6.8 Hz), 6.16 (1H, d, J=16.0 Hz), 6.37-7.00 (6H, m), 6.90 (1H, d, J=8.1 Hz).

Example 62

7-{2-[5-methyl-2-(trans-1-penten-1-yl)oxazol-4-yl]ethoxy}-2-(2,2,3,3,3-pentafluoropropyl)-1,2,3,4-tetrahydroisoquinoline-(3S)-carboxylic acid IR ν (Nujol) cm$^{-1}$; 1697, 1610, 1529, 1508.
$^1$H-NMR (DMSO-d$_6$) δ (ppm); 0.89 (3H, t, J=7.3 Hz), 1.20-1.70 (2H, m), 1.95-2.25 (2H, m), 2.25 (3H, s), 2.00-4.40 (1H, br), 2.79 (2H, m), 2.95-3.15 (2H, m), 3.30-4.40 (7H, m), 6.19 (1H, d, J=16.5 Hz), 6.33-6.90 (3H, m), 7.02 (1H, d, J=8.1 Hz).

Example 63

7-{2-[5-methyl-2-(trans-1-penten-1-yl)oxazol-4-yl]ethoxy}-2-(3,3,3-trifluoropropyl)-1,2,3,4-tetrahydroisoquinoline-(3S)-carboxylic acid IR ν (Nujol) cm$^{-1}$; 1616, 1506.
$^1$H-NMR (CDCl$_3$) δ (ppm); 0.93 (3H, t, J=6.8 Hz), 1.30-1.75 (2H, m), 2.10-2.70 (4H, m), 2.27 (3H, s), 2.75-3.40 (6H, m), 3.60-4.20 (5H, m), 5.80-8.00 (1H, br), 6.10-6.80 (4H, m), 7.02 (1H, d, J=8.1 Hz).

Example 64

2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic acid IR ν (Nujol) cm$^{-1}$; 3385, 3080, 2725, 2583, 1717, 1614, 1533, 1506.
$^1$H-NMR (CDCl$_3$) δ (ppm); 0.93 (6H, d, J=6.4 Hz), 1.48-1.99 (1H, m), 2.11 (2H, t, J=6.7 Hz), 2.28 (3H, s), 2.35-2.62 (2H, m), 2.70-3.35 (6H, m), 3.76 (1H, br-t), 3.85-4.46 (4H, m), 4.90-5.25 (2H, m), 5.45-5.98 (1H, m), 6.15 (1H, d, J=16.1 Hz), 6.40-6.86 (3H, m), 7.08 (1H, d, J=8.2 Hz), 8.60-9.00 (1H, br).

Example 65 tert-butylamine 2-(2,4-hexadienoyl)-7-{2-[2-(3-methoxy-trans-1-propen-1-yl)-5-methyloxazol-4-yl]ethoxy}-1,2,3,4-tetrahydroisoquinoline-(3S)-carboxylate IR ν (Nujol) cm$^{-1}$; 2737, 1652, 1624, 1599, 1555, 1587, 1506.
$^1$H-NMR (CDCl$_3$) δ (ppm); 1.00 (9H, s), 1.85-2.00 (3H, m), 2.29 (3H, s), 2.87 (2H, t, J=6.8 Hz), 2.90-3.25 (2H, m), 3.38 (3H, s), 3.95-4.20 (2H, m), 4.11 (2H, t, J=6.8 Hz), 4.30-5.20 (3H, m), 5.90-8.40 (12H, m).

Example 66 tert-butylamine 7-{2-[2-(5-fluoro-trans-1-penten-1-yl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 2735, 2631, 2544, 2432, 2365, 2212, 1651, 1624, 1599, 1553, 1504.
$^1$H-NMR (CDCl$_3$) δ (ppm); 0.99 (9H, s), 1.50-2.10 (5H, m), 2.15-2.55 (2H, m), 2.28 (3H, s), 2.80-3.40 (2H, m), 2.86 (2H, t, J=6.6 Hz), 4.11 (2H, t, J=6.6 Hz), 4.47 (2H, dt, J=47.0, 5.7 Hz), 4.50-5.20 (3H, m), 5.80-6.80 (9H, m), 6.85-7.25 (2H, m).

Example 67 tert-butylamine 7-[2-(2-cyclopentylidenemiethyl-5-methyloxazol-4-yl)ethoxy]-2-(2,4-hexadienoyl)-1,2,3,4-tetrahydroisoquinoline-(3S)-carboxylate IR ν (Nujol) cm$^{-1}$; 2737, 2631, 2544, 1653, 1624, 1587, 1553, 1506.
$^1$H-NMR (CDCl$_3$) δ (ppm); 0.96 (9H, s), 1.50-2.05 (7H, m), 2.28 (3H, s), 2.25-2.55 (2H, m), 2.55-3.30 (4H, m), 2.87 (2H, t, J=6.8 Hz), 4.12 (2H, t, J=6.8 Hz), 4.25-5.20 (3H, m), 5.80-7.40 (11H, m).

Example 68 tert-butylamine 7-[2-(2-cyclohexylidenemethyl-5-methyloxazol-4-yl)ethoxy]-2-(2,4-hexadienoyl)-1,2,3,4-tetrahydroisoquinoline-(3S)-carboxylate IR ν (Nujol) cm$^{-1}$; 2739, 2631, 2542, 1653, 1624, 1549, 1506.
$^1$H-NMR(CDCl$_3$) δ (ppm); 1.01 (9H, s), 1.40-2.00 (9H, m), 2.10-2.40 (2H, m), 2.27 (3H, s), 2.65-3.40 (6H, m), 2.86 (2H, t, J=6.6 Hz), 4.12 (2H, t, J=6.6 Hz), 4.25-5.20 (3H, m), 5.80-7.40 (11H, m), 5.93 (1H, s).

Example 69 tert-butylamine 2-cyclopentylideneacetyl-7-{2-[5-methyl-2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 2745, 2638, 2554, 1655, 1556, 1506.
$^1$H-NMR (CDCl$_3$) δ (ppm); 0.94 (6H, d, J=6.8 Hz), 0.97 (9H, s), 1.43-2.00 (5H, m), 2.11 (2H, t, J=6.7 Hz), 2.28 (3H, s), 2.30-2.8 (4H, m), 2.86 (2H, t, J=6.8 Hz), 2.90-3.40 (2H, m), 4.11 (2H, t, J=6.8 Hz), 4.20-5.20 (3H, m), 5.93-6.28 (1H, m), 6.40-6.80 (3H, m), 6.80-7.20 (4H, m).

Example 70 tert-butylamine 2-cyclohexylideneacetyl-7-(2-[5-methyl-2-(4-methyl-trans-1-penten-1-yl)oxazol-4-yl]ethoxy)-1,2,3,4-tetrahydroisoquinoline-(3S)-carboxylate IR ν (Nujol) cm$^{-1}$; 2743, 2637, 2554, 2216, 1636, 1556, 1506.

$^1$H-NMR (CDCl$_3$) δ (ppm); 0.93 (6H, d, J=6.4 Hz), 1.02 (9H, s) 1.33-1.80 (7H, m), 2.00-2.50 (6H, m), 2.28 (3H, s), 2.86 (2H, t, J=6.7 Hz), 2.95-3.42 (2H, m), 4.11 (2H, t, J=6.7 Hz), 4.27-5.20 (3H, m), 5.64 (1H, d, J=7.7 Hz), 6.16 (1H, d, J=14.8 Hz), 6.40-6.80 (3H, m), 6.80-7.30 (4H, m).

Example 71 methyl 7-{2-[2-(5-tert-butylsulfanyl-trans-1-penten-1-yl)-5-methyloxazol-4-yl]ethoxy}-1,2,3,4-tetrahydroisoquinoline-(3S)-carboxylate IR ν (neat) cm$^{-1}$; 2928, 2864, 1740, 1638, 1612, 1578, 1533, 1504.

$^1$H-NMR (CDCl$_3$) δ (ppm); 1.32 (9H, s), 1.60-2.00 (2H, m), 1.98 (1H, br-s), 2.15-2.40 (2H, m), 2.27 (3H, s), 2.56 (2H, t, J=7.2 Hz), 2.80-3.05 (2H, m), 2.86 (2H, t, J=6.7 Hz), 3.55-3.80 (1H, m), 3.76 (3H, s), 4.04 (2H, br-s), 4.16 (2H, t, J=6.7 Hz), 6.17 (1H, d, J=16.0 Hz), 6.40-6.80 (3H, m), 6.99 (1H, d, J=8.3 Hz).

Example 72 methyl 7-{2-[2-(5-tert-butylsulfanyl-trans-1-penten-1-yl)-5-methyloxazol-4-yl]ethoxy}-2-(2,4-hexadienoyl)-1,2,3,4-tetrahydroisoquinoline-(3S)-carboxylate IR ν (neat) cm$^{-1}$; 2957, 2926, 2862, 1740, 1655, 1612, 1506.

$^1$H-NMR (CDCl$_3$) δ (ppm); 1.32 (9H, s), 1.60-2.00 (5H, m), 2.15-2.40 (2H, m), 2.28 (3H, s), 2.57 (2H, t, J=7.5 Hz), 2.87 (2H, t, J=6.6 Hz), 3.00-3.25 (2H, m), 3.59 (3H, s), 4.15 (2H, t, J=6.6 Hz), 4.35-5.60 (3H, m), 5.90-6.85 (7H, m), 7.04 (1H, d, J=8.4 Hz), 7.15-7.50 (1H, m).

Example 73 tert-butylamine 7-{2-[2-(5-tert-butylsulfanyl-trans-1-penten-1-yl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 2743, 2635, 2548, 1742, 1655, 1628, 1601, 1555, 1506.

$^1$H-NMR (CDCl$_3$) δ (ppm); 1.00 (9H, s), 1.32 (9H, s), 1.60-2.00 (5H, m), 2.15-2.40 (2H, m), 2.28 (3H, s), 2.56 (2H, t, J=7.2 Hz), 2.86 (2H, t, J=6.3 Hz), 2.90-3.35 (2H, m), 4.11 (2H, t, J=6.3 Hz), 4.30-5.15 (3H, m), 5.90-7.35(12H, m).

Example 74 methyl 7-{2-[2-(5-dimethylamino-trans-1-penten-1-yl)-5-methyloxazol-4-yl]ethoxy)-2-(2,4-hexadienoyl)-1,2,3,4-tetrahydroisoquinoline-(3S)-carboxylate IR ν (neat) cm$^{-1}$; 3404, 2949, 2860, 2818, 2770, 1743, 1655, 1626, 1603, 1533, 1506.

$^1$H-NMR (CDCl$_3$) δ (ppm); 1.40-1.95 (5H, m), 2.10-2.40 (4H, m), 2.23 (6H, s), 2.28 (3H, s), 2.87 (2H, t, J=6.6 Hz), 3.05-3.25 (2H, m), 3.59 (3H, m), 4.14 (2H, t, J=6.6 Hz), 4.60-5.00 (2H, m), 5.40-5.70 (1H, m), 6.00-6.80 (7H, m), 6.90-7.35 (2H, m).

Example 75

Sodium 7-{2-[2-(5-dimethylamino-trans-1-penten-1-yl)-5-methyloxazol-4-yl]ethoxy}-2-(2,4-hexadienoyl)-1,2,3,4-tetrahydroisoquinoline-(3S)-carboxylate IR ν (Nujol) cm$^{-1}$; 3381, 2766, 2725, 1651, 1595, 1535, 1504.

$^1$H-NMR (CDCl$_3$) δ (ppm); 1.40-1.95 (5H, m), 2.05-2.60 (4H, m), 2.25 (9H, s), 2.65-3.10 (4H, m), 3.90-4.10 (2H, m), 4.40-4.80 (2H, m) 5.05-5.55 (1H, m), 5.80-6.75 (7H, m), 6.80-7.25 (2H, m).

Example 76 tert-butylamine 2-(2-hexenoyl)-7-{2-[5-methyl-2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 1661, 1616, 1558, 1506.

$^1$H-NMR (CDCl$_3$) δ (ppm); 0.75-2.20 (3H, m), 0.93 (6H, d, J=6.4 Hz), 1.02 (9H, s), 1.20-1.60 (2H, m), 1.60-1.95 (1H, m), 1.95-2.30 (4H, m), 2.10 (2H, t, J=6.6 Hz), 2.27 (3H, s), 2.86 (2H, t, J=6.8 Hz), 3.00-3.40 (2H, m), 4.10 (2H, t, J=6.8 Hz), 4.40-5.20 (3H, m), 6.15 (1H, d, J=16.1 Hz), 6.10-7.20 (9H, m).

Example 77 tert-butylamine 2-(2,4-hexadienoyl)-7-{2-[2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 3435, 2729, 2633, 2548, 2214, 1657, 1630, 1551, 1504.

$^1$H-NMR (CDCl$_3$) δ (ppm); 0.94 (6H, d, J=6.6 Hz), 0.97 (9H, s), 1.60-1.90 (4H, m), 2.13 (2H, t, J=6.8 Hz), 2.80-3.20 (2H, m), 3.03 (2H, t, J=6.6 Hz), 4.15 (2H, t, J=6.6 Hz), 4.25-5.20 (3H, m), 6.00-7.30(12H, m), 7.38 (1H, s).

Example 78 tert-butylamine 7-(2-[2-(trans-2-cyclopentylvinyl)oxazol-4-yl]ethoxy}-2-(2,4-hexadienoyl)-1,2,3,4-tetrahydroisoquinoline-(3S)-carboxylate $^1$H-NMR (CDCl$_3$) δ (ppm); 0.99 (9H, s), 1.20-2.05(11H, m), 2.38-2.73 (1H, m), 2.90-3.40 (2H, m), 2.94 (2H, t, J=6.5 Hz), 4.14 (2H, t, J=6.5 Hz), 4.26-5.20 (3H, m), 5.86-7.38 (12H, m), 7.50 (1H, s).

Example 79 tert-butylamine 7-{2-[2-(trans-2-cyclohexylvinyl)oxazol-4-yl]ethoxy}-2-(2,4-hexadienoyl)-1,2,3,4-tetrahydroisoquinoline-(3S)-carboxylate $^1$H-NMR (CDCl$_3$) δ (ppm); 0.98 (9H, s), 1.00-2.40(14H, m), 2.90-3.30 (2H, m), 2.94 (2H, t, J=6.8 Hz), 4.14 (2H, t, J=6.8 Hz), 4.20-5.20 (3H, m), 5.80-7.47(12H, m), 7.49 (1H, s).

Example 80 tert-butylamine 2-(2-heptenoyl)-7-{2-[2-(4-methyl-trans-1-penten-1-yl)oxazol-4-yl]ethoxy}-1,2,3,4-tetrahydroisoquinoline-(3S)-carboxylate $^1$H-NMR (CDCl$_3$) δ (ppm); 0.75-2.20 (3H, m), 0.93 (6H, d, J=6.4 Hz), 1.02 (9H, s), 1.20-1.60 (4H, m), 1.60-1.95 (1H, m), 1.95-2.30 (2H, m), 2.10 (2H, t, J=6.6 Hz), 2.95 (2H, t, J=6.8 Hz), 3.00-3.40 (2H, m), 4.15 (2H, t, J=6.8 Hz), 4.40-5.20 (3H, m), 6.15 (1H, d, J=16.1 Hz), 6.10-7.20 (9H, m), 7.48 (1H, s).

Example 81 tert-butylamine 2-(2-hexenoyl)-7-{2-[2-(4-methyl-trans-1-penten-1-yl)oxazol-4-yl]ethoxy}-1,2,3,4-tetrahydroisoquinoline-(3S)-carboxylate IR ν (Nujol) cm$^{-1}$; 3435, 2729, 2633, 2548, 2214, 1661, 1622, 1553, 1504.

$^1$H-NMR (DMSO-d$_6$) δ (ppm); 0.80-1.00 (3H, m), 0.90 (6H, d, J=6.2 Hz), 1.14 (9H, s), 1.20-1.90 (6H, m), 1.95-2.25 (2H, m), 2.70-3.40 (3H, m), 4.10-5.20 (8H, m), 6.10-6.85 (6H, m), 7.00 (1H, d, J=8.4 Hz), 7.78 (1H, s).

Example 82 tert-butylamine 2-(2,4-hexadienoyl)-7-{2-[2-(trans-1-hexen-1-yl)oxazol-4-yl]ethoxy}-1,2,3,4-tetrahydroisoquinoline-(3S)-carboxylate $^1$H-NMR (CDCl$_3$) δ (ppm); 0.75-1.16 (3H, m), 0.98 (9H, s), 1.20-1.60 (4H, m), 1.70-2.00 (3H, m), 2.07-2.40 (2H, m), 2.88-3.30 (2H, m), 2.95 (2H, t, J=6.5 Hz), 4.16 (2H, t, J=6.5 Hz), 4.25-5.20 (3H, m), 5.90-7.40(12H, m), 7.49 (1H, s).

Example 83 tert-butylamine 2-(2,4-hexadienoyl)-7-{2-[2-(1-methyl-trans-1-penten-1-yl)oxazol-4-yl]ethoxy}-1,2,3,4-tetrahydroisoquinoline-(3S)-carboxylate $^1$H-NMR (CDCl$_3$) δ (ppm); 0.80-1.08 (3H, m), 0.97 (9H, s), 1.11-1.70 (2H, m), 1.70-1.93 (3H, m), 1.93-2.35 (2H, m), 2.01 (3H, s), 2.90-3.40 (2H, m), 2.96 (2H, t, J=6.7 Hz), 4.14 (2H, t, J=6.7 Hz), 4.24-5.20 (3H, m), 5.92-7.38(11H, m), 7.50 (1H, s).

Example 84 tert-butylamine 2-(2,4-hexadienoyl)-7-{2-[2-(1-methyl-trans-1-buten-1-yl), oxazol-4-yl]ethoxy}-1,2,3,4-tetrahydroisoquinoline-(3S)-carboxylate $^1$H-NMR (CDCl$_3$) δ (ppm); 0.99 (9H, s), 1.05 (3H, t, J=7.5 Hz), 1.65-1.95 (3H, m), 2.01 (3H, s), 2.05-2.45 (2H, m), 2.90-3.30 (2H, m), 2.96 (2H, t, J=6.7 Hz), 4.15 (2H, t, J=6.7 Hz), 4.25-5.20 (3H, m), 5.90-8.30(13H, m)

Example 85 tert-butylamine 2-(2,4-hexadienoyl)-7-{2-[(5-methyl-trans-1-hexen-1-yl)oxazol-4-yl]ethoxy}-1,2,3,4-tetrahydroisoquinoline-(3S)-carboxylate $^1$H-NMR (CDCl$_3$) δ (ppm); 0.90 (6H, d, J=6.3 Hz), 0.97 (9H, s), 1.20-1.70 (3H, m), 1.70-1.98 (3H, m), 2.06-2.40 (2H, m), 2.90-3.25 (2H, m), 2.95 (2H, t, J=6.4 Hz), 4.15 (2H, t, J=6.4 Hz), 4.25-5.20 (3H, m), 5.72-7.38(12H, m), 7.50(1H, s).

Reference Example 1

Ethyl 2-tert-butoxycarbonyl-7-hydroxy-1,2,3,4-tetrahydroisoquinoline-(3S)-carboxylate (1) 3,5-Diiodo-L-tyrosine dihydrate (25 g) was suspended in conc. hydrochloric acid (250 ml), and 1,2-dimethoxyethane (18 ml) and 37% formalin (20 ml) were successively added. The mixture was heated to 75° C. over 30 min. To the reaction mixture were added conc. hydrochloric acid (120 ml), 1,2-dimethoxyethane (9 ml) and 37% formalin (10 ml), and the mixture was stirred at 75° C. for 18 h. The precipitated crystals were collected by filtration and washed with 1,2-dimethoxyethane (20 ml) to give 7-hydroxy-6,8-diiodo-1,2,3,4-tetrahydroisoquinoline-(3S)-carboxylic acid hydrochloride (12.8 g).

IR ν (Nujol) cm$^{-1}$; 1751, 1599, 1578.

$^1$H-NMR (CDCl$_3$) δ (ppm); 3.00-3.30 (2H, m), 4.05 (2H, s), 4.30 (1H, dd, J=5.9, 9.5 Hz), 7.71 (1H, s).

(2) The compound (12.8 g) obtained in the above-mentioned (1) was suspended in ethanol (500 ml) and conc. hydrochloric acid (10 ml) was added. The mixture was refluxed for 15 h. Ethanol was evaporated under reduced pressure, and ethyl acetate (300 ml) was added. The mixture was washed with saturated aqueous sodium hydrogen carbonate (100 ml) and saturated brine (100 ml), and dried (Na$_2$SO$_4$). Ethyl acetate was evaporated under reduced pressure to give ethyl 7-hydroxy-6,8-diiodo-1,2,3,4-tetrahydroisoquinoline-(3S)-carboxylate (11.11 g).

$^1$H-NMR (CDCl$_3$) δ (ppm); 1.29 (3H, t, J=7.0 Hz), 2.80-3.00 (2H, m), 3.30-4.10 (5H, m), 4.23 (2H, q, J=7.0 Hz), 7.46 (1H, s).

(3) 10% Pd—C (350 mg) was suspended in methanol (60 ml), and the compound (2.8 g) of (2) and triethylamine, (2.0 ml) were added. The mixture was subjected to catalytic hydrogenation at room temperature and 3.0 kgf/cm$^2$ for 3 h. Pd—C was filtered off and methanol was evaporated under reduced pressure. Ethyl acetate (100 ml) was added to the obtained residue, and the mixture was washed with saturated brine (100 ml) and dried (Na$_2$SO$_4$). Ethyl acetate was evaporated under reduced pressure to give ethyl 7-hydroxy-1,2,3,4-tetrahydroisoquinoline-(3S)-carboxylate (1.14 g).

IR ν (Nujol) cm$^{-1}$; 1732, 1607, 1516.

$^1$H-NMR (CDCl$_3$) δ (ppm); 1.28 (3H, t, J=7.0 Hz), 2.80-3.10 (3H, m) 3.60-3.80 (1H, m), 3.97 (2H, s), 4.05-4.20 (4H, m), 6.43 (1H, s), 6.50-6.80 (1H, m), 6.92 (1H, d, J=8.4 Hz).

(4) The compound (1.13 g) obtained in the above-mentioned (3) was dissolved in tetrahydrofuran (20 ml) and di-tert-butyl dicarbonate (1.5 g) was added. The mixture was stirred at room temperature for 1 h and ethyl acetate (30 ml) was added.

The mixture was washed with saturated brine (20 ml) and dried (Na$_2$SO$_4$). Ethyl acetate was evaporated under reduced pressure and the obtained residue was purified by column chromatography to give the title compound (1.51 g).

IR ν (Nujol) cm$^{-1}$; 3260, 1756, 1671, 1615, 1506.

$^1$H-NMR (CDCl$_3$) δ (ppm); 1.29 (3H, t, J=7.0 Hz), 1.47 (9H, s), 3.08 (2H, d, J=5.2 Hz), 4.21 (2H, q, J=7.0 Hz), 4.41 (1H, d, J=15.5 Hz), 4.60-5.25 (1H, m), 4.65 (1H, d, J=15.5 Hz), 5.00-6.00 (1H, br), 6.50-6.80 (2H, m), 6.98 (1H, d, J=8.1 Hz).

Reference Example 2 methyl 2-tert-butoxycarbonyl-7-hydroxy-1,2,3,4-tetrahydroisoquinoline-(3S)-carboxylate The title compound was obtained in the same manner as in Reference Example 1.

IR ν (Nujol) cm$^{-1}$; 3261, 1755, 1672, 1614, 1506.

$^1$H-NMR (CDCl$_3$) δ (ppm); 1.47 (9H, s), 3.08 (2H, d, J=5.2 Hz) 3.63 (3H, s), 4.40 (1H, d, J=16.5 Hz), 4.60-5.25 (1H, m), 4.66 (1H, d, J=16.5 Hz), 5.60-6.60 (1H, br), 6.50-6.80 (2H, m), 6.99 (1H, d, J=8.1 Hz).

Reference Example 3 methyl 2-(2,4-hexadienoyl)-7-hydroxy-1,2,3,4-tetrahydroisoquinoline-(3S)-carboxylate Methyl 7-hydroxy-1,2,3,4-tetrahydroisoquinoline-(3S)-carboxylate (1.24 g) was dissolved in methylene chloride (25 ml) and triethylamine (5.0 ml) was added, which was followed by dropwise addition of sorbic acid chloride (2.1 ml) under ice-cooling. This was stirred at the same temperature for 15 min, washed with 10% aqueous citric acid solution (20 ml), saturated aqueous sodium hydrogen carbonate (20 ml) and saturated brine (20 ml), and dried (Na$_2$SO$_4$). Methylene chloride was evaporated under reduced pressure and the obtained residue was purified by column chromatography. The obtained oil (1.04 g) was dissolved in methanol (20 ml), and 1M aqueous lithium hydroxide solution (3.0 ml) was added by portions at room temperature. After acidification with 10% aqueous citric acid solution, the mixture was extracted with ethyl acetate (50 ml). The ethyl acetate layer was washed with saturated brine (20 ml) and dried (Na$_2$SO$_4$). Ethyl acetate was evaporated under reduced pressure and the obtained residue was purified by column chromatography to give the title compound (0.65 g).

IR ν (neat) cm$^{-1}$; 3184, 1734, 1576, 1506.

$^1$H-NMR (CDCl$_3$) δ (ppm); 1.84 (3H, d, J=5.0 Hz), 2.80-3.40 (2H, m), 3.59 (3H, s), 4.30-5.10 (2H, m), 5.30-5.60 (1H, m), 5.70-6.50 (4H, m), 6.64 (1H, s), 6.68 (1H, d, J=7.9 Hz), 6.99 (1H, d, J=7.9 Hz), 7.15-7.50 (1H, m).

Reference Example 4 methyl 2-(2-heptenoyl)-7-hydroxy-1,2,3,4-tetrahydroisoquinoline-(3S)-carboxylate Methyl 7-hydroxy-1,2,3,4-tetrahydroisoquinoline-(3S)-carboxylate (0.9 g) was dissolved in methylene chloride (10 ml), and 2-heptenoic acid (1.39 g) and 1-ethyl-3-(3'-dimethylaminopropyl)carbodiimide hydrochloride (2.08 g) were added. The mixture was stirred at room temperature for 30 min. Methylene chloride (20 ml) was added, and the mixture was washed with 10% aqueous citric acid solution (20 ml) and saturated brine (20 ml), and dried (Na$_2$SO$_4$). Methylene chloride was evaporated under reduced pressure and the obtained residue was purified by column chromatography to give the title compound (1.15 g).

IR ν (neat) cm$^{-1}$; 3265, 1740, 1655, 1593, 1508.

$^1$H-NMR (CDCl$_3$) δ (ppm); 0.90 (3H, br-t), 1.10-1.70 (4H, m), 1.90-2.40 (2H, m), 3.00-3.40 (2H, m), 3.59 (3H, s), 4.35-5.65 (4H, m), 6.36 (1H, d, J=15.2 Hz), 6.55-6.80 (1H, m), 6.64 (1H, s), 6.80-7.20 (1H, m), 6.99 (1H, d, J=7.9 Hz).

Reference Example 5

2-(5-methyl-2-styryloxazol-4-yl)ethanol (1) β-methyl L-aspartate (20 g) was suspended in methylene chloride (400 ml), and cinnamoyl chloride (18.14 g) was added. Triethylamine (53 ml) was added dropwise at −5° C. and the mixture was stirred at the same temperature for 1.5 h. The reaction mixture was extracted 5 times with water (300 ml), and the aqueous layer was acidified with 6M hydrochloric acid and was extracted with ethyl acetate (500 ml). The ethyl acetate layer was washed with saturated brine (300 ml) and dried (Na$_2$SO$_4$). Ethyl acetate was evaporated under reduced pressure and the obtained residue (13.3 g) was dissolved in toluene (100 ml). Acetic anhydride (22.6 ml), N-methylmorpholine (21.1 ml) and 4-dimethylaminopyridine were added and the mixture was stirred at 65° C. for 5 h. Saturated aqueous sodium hydrogen carbonate was added to the reaction mixture, neutralized and two layers were separated. The toluene layer was washed with saturated brine (100 ml) and dried (Na$_2$SO$_4$). Toluene was evaporated under reduced pressure, and the obtained residue (9.1 g) was dissolved in toluene (90 ml). Phosphorus oxychloride (9.2 ml) was added and the mixture was refluxed for 6 h. The reaction mixture was poured into ice water, neutralized with potassium carbonate and two layers were separated. The toluene layer was washed with saturated brine (100 ml) and dried (Na$_2$SO$_4$). Toluene was evaporated under reduced pressure and the obtained residue was purified by column chromatography to give methyl (5-methyl-2-styryloxazol-4-yl)acetate (1.31 g).

IR ν (neat) cm$^{-1}$; 1742, 1641.

$^1$H-NMR (CDCl$_3$) δ (ppm); 2.33 (3H, s), 3.52 (2H, s), 3.73 (3H, s), 6.85 (1H, d, J=16.2 Hz), 7.15-7.60 (6H, m).

(2) The compound (1.31 g) obtained in the above-mentioned (1) was dissolved in diethyl ether (25 ml), and lithium aluminum hydride (0.23 g) was added by portions at 0° C. The mixture was stirred at the same temperature for 20 min. Water (5 ml) was added, an insoluble material was filtered off and two layers were separated. The diethyl ether layer was washed with saturated brine (15 ml) and dried (Na$_2$SO$_4$). Diethyl ether was evaporated under reduced pressure and the obtained residue was purified by column chromatography to give the title compound (0.55 g).

$^1$H-NMR (CDCl$_3$) δ (ppm); 2.31 (3H, s), 2.61 (2H, d, J=6.0 Hz), 3.20-3.50 (1H, br), 3.84 (2H, d, J=6.0 Hz), 6.84 (1H, d, J=16.2 Hz), 7.20-7.60 (6H, m).

Reference Example 6 methyl (5-methyl-2-styryloxazol-4-yl)acetate

Cinnamamide (0.5 g) and methyl 4-bromo-3-oxopentanoate (0.71 g) were dissolved in N,N-dimethylformamide (2.5 ml) and the mixture was stirred 100° C. for 15 h. Ethylacetate (50 ml) was added, and the mixture was washed with water (100 ml) and then with saturated brine (100 ml), and dried (Na$_2$SO$_4$). Ethyl acetate was evaporated under reduced pressure and the obtained residue was purified by column chromatography to give the title compound (0.1 g).

The IR and $^1$H-NMR were the same as those in Reference Example 5(1).

The following compounds were synthesized in the same manner as in Reference Examples 5 and 6.

Reference Example 7

2-(5-methyl-2-(trans-1-penten-1-yl)oxazol-4-yl)ethanol

IR ν (neat) cm$^{-1}$; 3350, 1664, 1654, 1641, 1534.
$^1$H-NMR (CDCl$_3$) δ (ppm); 0.95 (3H, t, J=7.0 Hz), 1.20-1.80 (2H, m), 2.00-2.40 (2H, m), 2.25 (3H, s), 2.64 (2H, t, J=5.7 Hz), 2.70-3.20 (1H, br) 3.86 (2H, t, J=5.7 Hz), 6.17 (1H, d, J=8.0 Hz), 6.64 (1H, dt, J=6.6, 8.0 Hz).

Reference Example 8

2-(5-methyl-2-pentyloxazol-4-yl)ethanol

IR ν (neat) cm$^{-1}$; 3341, 1576.
$^1$H-NMR (CDCl$_3$) δ (ppm); 0.90 (3H, br-t), 1.20-1.50 (4H, m), 1.50-1.95 (2H, m), 2.21 (3H, s), 2.45-2.80 (4H, m), 3.09 (1H, br-s), 3.85 (2H, t, J=5.7 Hz).

Reference Example 9

2-(2-cyclopentyl-5-methyloxazol-4-yl)ethanol

IR ν (neat) cm$^{-1}$; 3341, 1572.
$^1$H-NMR (CDCl$_3$) δ (ppm); 1.40-2.30 (8H, m), 2.21 (3H, s), 2.61 (2H, t, J=6.0 Hz), 2.95-3.30 (1H, m), 3.36 (1H, br-s), 3.84 (2H, t, J=6.0 Hz).

Reference Example 10

2-(2-cyclohexyl-5-methyloxazol-4-yl)ethanol

IR ν (neat) cm$^{-1}$; 3360, 1742, 1570, 1450.
$^1$H-NMR (CDCl$_3$) δ (ppm); 1.10-2.40 (11H, m), 2.21 (3H, s), 2.60-3.00 (1H, m), 2.61 (2H, t, J=5.8 Hz), 3.09 (1H, br-s), 3.84 (2H, t, J=5.8 Hz).

Reference Example 11

2-[5-methyl-2-(trans-1-penten-1-yl)oxazol-4-yl]ethyl methanesulfonate

2-[5-Methyl-2-(1-penten-1-yl)oxazol-4-yl]ethanol (1.03 g) was dissolved in methylene chloride (10 ml), and triethylamine (1.03 ml) was added. Methanesulfonyl chloride (0.41 ml) was added dropwise at 0° C., and the mixture was stirred at room temperature for 30 min. Ethyl acetate (100 ml) was added, and the mixture was washed with 10% aqueous citric acid solution (100 ml) and then with saturated brine (100 ml), and dried (Na$_2$SO$_4$). The solvent was evaporated under reduced pressure to give the title compound (1.1 g).

IR ν (neat) cm$^{-1}$; 1654, 1643, 1551, 1534.
$^1$H-NMR (CDCl$_3$) δ (ppm); 0.90 (3H, t, J=7.2 Hz), 1.20-1.80 (2H, m), 2.00-2.40 (2H, m), 2.27 (3H, s), 2.86 (2H, t, J=6.7 Hz), 2.94 (3H, s), 4.45 (2H, t, J=6.7 Hz), 6.16 (1H, d, J=16.0 Hz), 6.69 (1H, dt, J=16.0, 6.6 Hz).

Reference Example 12

2-(5-methyl-2-styrylthiazol-4-yl)ethyl methanesulfonate (1) Cinnamamide (3.27 g) was dissolved in tetrahydrofuran (33 ml), and Lawesson's reagent (4.94 g) was added. The mixture was refluxed for 3 h and methyl 4-bromo-3-oxopentanoate (6.97 g) was added. The mixture was further refluxed for 11 h. Tetrahydrofuran was evaporated under reduced pressure and ethyl acetate (300 ml) was added to the obtained residue. The mixture was washed with water (200 ml) and then with saturated brine (200 ml), and dried (Na$_2$SO$_4$). Ethyl acetate was evaporated under reduced pressure and the obtained residue was purified by column chromatography to give methyl (5-methyl-2-styrylthiazole-4-yl)acetate (2.9 g).

IR ν (Nujol) cm$^{-1}$; 1732, 1595, 1573, 1537.
$^1$H-NMR (CDCl$_3$) δ (ppm); 2.41 (3H, s), 3.72 (3H, s), 3.75 (2H, s), 7.15-7.60 (7H, m).

(2) The compound (2.85 g) obtained in the above-mentioned (1) was dissolved in toluene (16.7 ml), and 1.5M diisobutyl aluminum hydrate toluene solution (16.7 ml) was added dropwise at −10° C. The mixture was stirred at the same temperature for 1 h and water (5 ml) was added. An insoluble material was filtered off and two layers were separated. The toluene layer was washed with saturated brine (10 ml) and dried (Na$_2$SO$_4$) Toluene was evaporated under reduced pressure and the obtained crude 2-(5-methyl-2-styrylthiazol-4-yl) ethanol (2.8 g) was dissolved in methylene chloride (30 ml). Triethylamine (1.89 ml) was added, and methanesulfonyl chloride (0.97 ml) was added dropwise at 0° C. The mixture was stirred at room temperature for 20 min. Ethyl acetate (200 ml) was added, and the mixture was washed with 10% aqueous citric acid solution (200 ml) and then with saturated brine (100 ml), and dried (Na$_2$SO$_4$). The solvent was evaporated under reduced pressure and the obtained residue was purified by column chromatography to give the title compound (1.1 g).

$^1$H-NMR (CDCl$_3$) δ (ppm); 2.42 (3H, s), 2.91 (3H, s), 3.11 (2H, t, J=6.6 Hz), 4.57 (2H, t, J=6.6 Hz), 7.00-7.65 (7H, m).

Reference Example 13

2-[(1-phenylethylidene)aminooxy]ethanol

Acetophenone oxime (1.00 g) and 2-(2-bromoethoxy)-tetrahydropyrane (3.09 g) were dissolved in N,N-dimethylacetamide (30 ml), and potassium carbonate (7.16 g) was added. The mixture was stirred at 80° C. for 19 h. After allowing to cool, water (100 ml) was added to the reaction mixture. The mixture was extracted twice with ethyl acetate (50 ml). The ethylacetate layers were combined, washed with water (50 ml) and then with saturated brine (50 ml), and dried (Na$_2$SO$_4$). Ethyl acetate was evaporated under reduced pressure and the obtained residue was purified by column chromatography to give a colorless oil (2.01 g). The obtained oil (1.99 g) was dissolved in methanol (30 ml), and p-toluenesulfonic acid monohydrate (1.73 g) was added. The mixture was stirred at room temperature for 1 h. Methanol was evaporated under reduced pressure and saturated aqueous sodium hydrogen carbonate solution (30 ml) was added. The mixture was extracted twice with ethyl acetate (30 ml). The ethyl acetate layers were combined and washed with saturated aqueous sodium hydrogen carbonate solution (50 ml) and then with saturated brine (50 ml), and dried (Na$_2$SO$_4$). Ethyl acetate was evaporated under reduced pressure and the obtained residue was purified by column chromatography to give the title compound (1.09 g).

IR ν (neat) cm$^{-1}$; 3700-3100, 1445, 1369, 1315, 1043, 762, 694, 559.

$^1$H-NMR (CDCl$_3$) δ (ppm); 2.27 (3H, s), 3.8-4.1 (2H, m), 4.2-4.5 (2H, m), 7.2-7.5 (3H, m), 7.5-7.8 (2H, m).

The following compounds were synthesized in the same manner as in Reference Example 11.

Reference Example 14

2-[(1-phenylethylidene)aminooxy]ethyl methanesulfonate

IR ν (Nujol) cm$^{-1}$; 1354, 1177, 1069, 1018, 924, 804, 764, 696, 529.

$^1$H-NMR (CDCl$_3$) δ (ppm); 2.26 (3H, s), 3.02 (3H, s), 4.3-4.7 (4H, m), 7.2-7.5 (3H, m), 7.5-7.8 (2H, m).

Reference Example 15

2-(4-methyl-2-phenylsulfanylthiazol-5-yl)ethyl methanesulfonate (1) Thiophenol (1.90 ml) was dissolved in N,N-dimethylformamide (10 ml) Sodium hydride (60% oil suspension, 740 mg) was added by portions under ice-cooling, and the mixture was stirred at room temperature for 15 min. Thereafter, a solution of ethyl 2-chloro-4-methylthiazole-5-carboxylate (3.05 g) in N,N-dimethylformamide (10 ml) was added dropwise, and the mixture was stirred at the same temperature for 20 min. Water (50 ml) was added to the reaction mixture, and the mixture was extracted with ethyl acetate (50 ml). The ethyl acetate layer was washed twice with water (50 ml) and then with saturated brine (30 ml), and dried (Na$_2$SO$_4$). Ethyl acetate was evaporated under reduced pressure and the obtained residue was purified by column chromatography to give ethyl 4-methyl-2-phenylsulfanylthiazole-5-carboxylate (3.85 g).

IR ν (neat) cm$^{-1}$; 1713, 1531.

$^1$H-NMR (CDCl$_3$) δ (ppm); 1.28 (3H, t, J=7.2 Hz), 2.67 (3H, s), 4.24 (2H, t, J=7.2 Hz), 7.40-7.80 (5H, m).

(2) The compound (3.85 g) obtained in the above-mentioned (1) was dissolved in tetrahydrofuran (80 ml), and lithium aluminum hydride (630 mg) was added under ice-cooling by portions. The mixture was stirred at the same temperature for 15 min. Water (20 ml) and ethyl acetate (50 ml) were added, and an insoluble material was filtered off. Two layers were separated, and the ethyl acetate layer was washed with saturated brine (20 ml) and dried (Na$_2$SO$_4$). Ethyl acetate was evaporated under reduced pressure, and the obtained residue purified by column chromatography to give 4-methyl-2-phenylsulfanylthiazole-5-methanol (3.25 g).

IR ν (neat) cm$^{-1}$; 3265, 1582, 1555.

$^1$H-NMR (CDCl$_3$) δ (ppm); 2.31 (3H, s), 2.50 (1H, s), 4.65 (2H, s), 7.30-7.70 (5H, m).

(3) The compound (7.30 g) obtained in the above-mentioned (2) was dissolved in methylene chloride (100 ml). Triethylamine (6.40 ml) was added and methanesulfonyl chloride (2.90 ml) was added dropwise under ice-cooling, and the mixture was stirred at room temperature for 30 min. The reaction mixture was washed with cold water (20 ml) and dried (Na$_2$SO$_4$). Methylene chloride was evaporated under reduced pressure, and the obtained residue was dissolved in acetonitrile (100 ml). Sodium cyanide (2.26 g) and 18-crown-6 (1.50 g) were added, and the mixture was stirred at 60° C. for 2 h. Acetonitrile was evaporated under reduced pressure and ethyl acetate (100 ml) was added to the obtained residue. The mixture was washed twice with water (50 ml) and then with saturated brine (30 ml), and dried (Na$_2$SO$_4$). Ethyl acetate was evaporated under reduced pressure and the obtained residue was purified by column chromatography to give (4-methyl-2-phenylsulfanylthiazol-5-yl)acetonitrile (2.80 g).

IR ν (neat) cm$^{-1}$; 2254, 1582, 1555.

$^1$H-NMR (CDCl$_3$) δ (ppm); 2.36 (3H, s), 3.68 (2H, s), 7.40-7.70 (5H, m).

(4) The compound (2.80 g) obtained in the above-mentioned (3). was dissolved in conc. hydrochloric acid (5.6 ml) and the mixture was stirred at 100° C. for 20 min. Methanol (120 ml) was added to the reaction mixture and the mixture was refluxed for 1 h. Methanol was evaporated under reduced pressure and ethyl acetate (50 ml) was added to the obtained residue. The mixture was washed with water (50 ml), saturated aqueous sodium hydrogen carbonate (30 ml) and then with saturated brine (30 ml), and dried (Na$_2$SO$_4$). Ethyl acetate was evaporated under reduced pressure to give methyl (4-methyl-2-phenylsulfanylthiazol-5-yl)acetate (2.77 g).

IR ν (neat) cm$^{-1}$; 1740.

$^1$H-NMR (CDCl$_3$) δ (ppm); 2.33 (3H, s), 3.64 (2H, s), 3.69 (3H, s), 6.30-6.70 (5H, m).

(5) The compound (2.77 g) obtained in the above-mentioned (4) was dissolved in tetrahydrofuran (55 ml), and lithium aluminum hydride (376 mg) was added by portions under ice-cooling. The mixture was stirred at the same temperature for 15 min. Water (20 ml) and ethyl acetate (50 ml) were added, and an insoluble material was filtered off. Two layers were separated and the ethyl acetate layer was washed with saturated brine (20 ml) and dried (Na$_2$SO$_4$). Ethyl acetate was evaporated under reduced pressure and the obtained residue was purified by column chromatography to give 2-(4-methyl-2-phenylsulfanylthiazol-5-yl)ethanol (2.49 g).

IR ν (neat) cm$^{-1}$; 3302.

$^1$H-NMR (CDCl$_3$) δ (ppm); 1.60-2.00 (1H, br), 2.33 (3H, s), 2.89 (2H, t, J=6.1 Hz), 3.75 (2H, t, J=6.1 Hz), 7.30-7.70 (5H, m).

(6) The compound (2.49 g) obtained the above-mentioned (5) was dissolved in methylene chloride (25 ml), and triethylamine (2.0 ml) was added. Methanesulfonyl chloride (0.93 ml) was added dropwise, and after under ice-cooling, the mixture was stirred at the same temperature for 30 min. The mixture was washed with 10% aqueous citric acid solution (20 ml), saturated aqueous sodium hydrogen carbonate (20 ml) and then with saturated brine (20 ml), and dried (Na$_2$SO$_4$). Methylene chloride was evaporated under reduced pressure, and the obtained residue was purified by column chromatography to give the title compound (1.82 g).

IR ν (neat) cm$^{-1}$; 1582, 1551.

$^1$H-NMR (CDCl$_3$) δ (ppm); 2.34 (3H, s), 2.92 (3H, s), 3.09 (2H, t, J=6.6 Hz), 4.26 (2H, t, J=6.6 Hz), 7.30-7.80 (5H, m).

Reference Example 16 methyl 2-[5-methyl-2-(4-methyl-trans-1-penten-1-yl) oxazol-4-yl]acetate

5-Methyl-trans-2-hexanamide (5.7 g) was suspended in toluene (35 ml) and 4-bromopropionylmethyl acetate (14.0 g) was added. The mixture was refluxed for 14 h. Ethyl acetate (50 ml) was added, and the mixture was washed successively with water (50 ml) and saturated brine (50 ml), and dried (Na$_2$SO$_4$). The solvent was evaporated under reduced pressure and the obtained residue was purified by column chromatography to give the title compound (3.36 g).

IR ν (neat) cm$^{-1}$; 2957, 2928, 2870, 1746, 1643, 1551.

$^1$H-NMR (CDCl$_3$) δ (ppm); 0.94 (6H, d, J=6.3 Hz), 1.50-2.10 (1H, m), 2.11 (2H, t, J=6.9 Hz), 2.27 (3H, s), 3.48 (2H, s), 3.71 (3H, s), 6.17 (1H, d, J=16.0 Hz), 6.61 (1H, dt, J=6.9 Hz, 16.0 Hz).

Reference Example 17 methyl 2-[5-methyl-2-(4-methyl-trans-1-penten-1-yl)oxazol-4-yl]acetate (1) β-Methyl L-aspartate (44.68 g) was dissolved in water (220 ml), and sodium carbonate (42.54 g) was added. Tetrahydrofuran (110 ml) was added and 5-methyl-trans-2-hexenoyl chloride (42.8 g) was added dropwise. The mixture was stirred at room temperature for 15 h and water (22 ml) was added. The mixture was washed with ethyl acetate (110 ml), and the aqueous layer was adjusted to pH 2 with conc. hydrochloric acid and extracted with ethyl acetate (400 ml). The ethyl acetate layer was washed successively with water and saturated brine (150 ml each), and dried (Na$_2$SO$_4$). Ethyl acetate was evaporated under reduced pressure to give an oil (59.7 g). The obtained oil was dissolved in toluene (220 ml), and acetic anhydride (60 ml), pyridine (52 ml) and 4-dimethylaminopyridine (5.2 g) were added. The mixture was stirred at 65° C. for 5 h. The reaction mixture was washed with water (300 ml) and 1M hydrochloric acid (500 ml). Water (300 ml) was added to the toluene layer and the mixture was neutralized with sodium bicarbonate. Two layers were separated, and the toluene layer was washed with saturated brine (200 ml) and dried (Na$_2$SO$_4$). Toluene was evaporated under reduced pressure and n-hexane was added to the obtained residue. The precipitated crystals were collected by filtration to give methyl 3-(5-methyl-trans-2-hexenoylamino)-4-oxopentanoate (27.42 g).

IR ν (neat) cm$^{-1}$; 3329, 1747, 1720, 1666, 1626, 1531.

$^1$H-NMR (CDCl$_3$) δ (ppm); 0.93 (6H, d, J=6.4 Hz), 1.50-2.00 (1H, m), 2.09 (2H, t, J=7.0 Hz), 2.25 (3H, s), 2.78,3.06 (2H, ABq, J=4.4, 17.2 Hz), 3.69 (3H, s), 4.70-4.95 (1H, m), 5.83 (1H, d, J=15.1 Hz), 6.45-7.00 (1H, br), 6.88 (1H, dt, J=7.2 Hz, 15.1 Hz).

(2) The compound (0.8 g) obtained in the above-mentioned (1) was the above-mentioned (1) was dissolved in toluene (5.6 ml), and phosphorus oxychloride (0.58 ml) was added. The mixture was refluxed for 1 h. The reaction mixture was poured into ice water (10 ml), and after neutralization with sodium bicarbonate, two layers were separated. The toluene layer was washed with saturated brine (10 ml) and dried (Na$_2$SO$_4$). Toluene was evaporated under reduced pressure and the obtained residue was purified by column chromatography to give the title compound (0.9 g).

The IR and $^1$H-NMR were the same as those in Reference Example 16.

Reference Example 18

2-[5-methyl-2-(4-methyl-trans-1-penten-1-yl)oxazol-4-yl]ethanol

The compound (3.34 g) of Reference Example 16 was dissolved in toluene (30 ml) and 1.5M diisobutylaluminum hydride toluene solution (37.5 ml) was added dropwise at −70° C. The mixture was stirred at −70° C. to −40° C. for 1 h. The reaction mixture was poured into water (100 ml) and an insoluble material was filtered off, after which two layers were separated. The toluene layer was washed with saturated brine. (50 ml) and dried (Na$_2$SO$_4$). Toluene was evaporated under reduced pressure and the obtained residue was purified by column chromatography to give the title compound (1.75 g).

IR ν (neat) cm$^{-1}$; 3346, 2957, 2926, 2870, 1661, 1641, 1533.

$^1$H-NMR (CDCl$_3$) δ (ppm); 0.94 (6H, d, J=6.4 Hz), 1.50-2.10 (1H, m), 2.11 (2H, t, J=7.0 Hz), 2.25 (3H, s), 2.71 (2H, t, J=5.9 Hz), 2.81 (1H, br-s), 3.86 (2H, t, J=5.9 Hz), 6.16 (1H, d, J=16.0 Hz), 6.62 (1H, dt, J=7.0,16.0 Hz).

Reference Example 19

2-[5-methyl-2-(4-methyl-trans-1-penten-1-yl)oxazol-4-yl]ethyl methanesulfonate

The compound (1.73 g) of Reference Example 18 was dissolved in methylene chloride (20 ml) and triethylamine (2.3 ml) was added. Methanesulfonyl chloride (0.77 ml) was added dropwise at 0° C. and the mixture was stirred at room temperature for 20 min. Methylene chloride (30 ml) was added, washed with 10% aqueous citric acid solution (30 ml) and then with saturated brine (30 ml), and dried (Na$_2$SO$_4$). Methylene chloride was evaporated under reduced pressure and the obtained residue was purified by column chromatography to give the title compound (2.21 g).

IR ν (neat) cm$^{-1}$; 2959, 2928, 2870, 1643, 1535.

$^1$H-NMR (CDCl$_3$) δ (ppm); 0.94 (6H, d, J=6.4 Hz), 1.50-2.10 (1H, m), 2.12 (2H, t, J=7.0 Hz), 2.27 (3H, s), 2.87 (2H, t, J=6.7 Hz), 2.94 (3H, s), 4.45 (2H, t, J=6.6 Hz), 6.15 (1H, d, J=15.8 Hz), 6.62 (1H, dt, J=7.0,15.8 Hz).

The following compounds were synthesized in the same manner as in Reference Example 19.

Reference Example 20

2-[2-(trans-2-cyclohexylvinyl)-5-methyloxazol-4-yl]ethyl methanesulfonate

IR ν (neat) cm$^{-1}$; 2926, 2853, 1736, 1643, 1533.

$^1$H-NMR (CDCl$_3$) δ (ppm); 0.85-2.50 (11H, m), 2.26 (3H, s), 2.86 (2H, t, J=6.6 Hz), 2.94 (3H, s), 4.44 (2H, t, J=6.6 Hz), 6.11 (1H, d, J=16.1 Hz), 6.46 (1H, dd, J=6.6,16.1 Hz).

Reference Example 21

2-[2-(trans-1-hepten-1-yl)-5-methyloxazol-4-yl]ethyl methanesulfonate

IR ν (neat) cm$^{-1}$; 3628, 3420, 2959, 2930, 2860, 1738, 1643, 1576, 1533.

$^1$H-NMR (CDCl$_3$) δ (ppm); 0.75-1.10 (3H, m), 1.10-1.67 (4H, m), 2.04-2.40 (2H, m), 2.27 (3H, s), 2.86 (2H, t, J=6.7 Hz), 2.94 (1H, s), 4.45 (2H, t, J=6.7 Hz), 6.16 (1H, d, J=16.0 Hz), 6.64 (1H, dt, J=16.0 Hz, 6.8 Hz).

Reference Example 22

2-[2-(5-methyl-trans-2-hexen-1-yl)5-methyloxazol-4-yl]ethyl methanesulfonate

IR ν (neat) cm$^{-1}$; 3632, 3410, 2957, 2928, 2870, 1661, 1643, 1535.
$^1$H-NMR (CDCl$_3$) δ (ppm); 0.91 (6H, d, J=6.2 Hz), 1.13-1.90 (3H, m), 2.00-2.22 (2H, m), 2.26 (3H, s), 2.86 (2H, t, J=6.7 Hz), 2.94 (3H, s), 4.45 (2H, t, J=6.7 Hz), 6.20 (1H, d, J=15.7 Hz), 6.62 (1H, dt, J=15.7, 6.2 Hz).

Reference Example 23

2-[5-methyl-2-(1-methyl-trans-1-buten-1-yl)oxazol-4-yl]ethyl methanesulfonate

IR ν (neat) cm$^{-1}$; 2966, 2934, 2876, 1647, 1572, 1535.
$^1$H-NMR (CDCl$_3$) δ (ppm); 1.07 (3H, t, J=6.8 Hz), 2.00 (3H, s), 2.05-2.40 (2H, m), 2.27 (3H, s), 2.87 (2H, t, J=6.6 Hz), 2.94 (3H, s), 4.45 (2H, t, J=6.6 Hz), 6.45 (1H, br-t).

Reference Example 24

2-[5-methyl-2-(1-methyl-trans-1-penten-1-yl)oxazol-4-yl]ethyl methanesulfonate

IR ν (neat) cm$^{-1}$; 3393, 2961, 2932, 2872, 1647, 1535.
$^1$H-NMR (CDCl$_3$) δ (ppm); 0.96 (3H, t, J=7.0 Hz), 1.20-1.73 (2H, m), 2.00 (3H, s), 2.00-2.40 (2H, m), 2.27 (3H, s), 2.87 (2H, t, J=6.6 Hz), 2.94 (1H, s), 4.45 (2H, t, J=6.6 Hz), 6.46 (1H, dt, J=1.4, 7.0 Hz).

Reference Example 25

2-[2-(trans-2-cyclopentylvinyl)-5-methyloxazol-4-yl]ethyl methanesulfonate

IR ν (neat) cm$^{-1}$; 2955, 2870, 1736, 1645, 1533.
$^1$H-NMR (CDCl$_3$) δ (ppm); 1.20-2.00 (8H, m), 2.26 (3H, s), 2.36-2.78 (1H, m), 2.86 (2H, t, J=6.6 Hz), 2.94 (3H, s), 4.44 (2H, t, J=6.6 Hz), 6.14 (1H, d, J=15.8 Hz), 6.62 (1H, dd, J=15.8, 7.5 Hz).

Reference Example 26

2-{5-methyl-2-[2-trans-(1-methylcyclohexyl)vinyl]oxazol-4-yl}ethyl methanesulfonate IR ν (neat) cm$^{-1}$; 2928, 2853, 1645, 1531, 1508.
$^1$H-NMR (CDCl$_3$) δ (ppm); 1.06 (3H, s), 1.20-1.80 (10H, m), 2.28 (3H, s), 2.87 (2H, t, J=6.6 Hz), 2.95 (3H, s), 4.45 (2H, t, J=6.6 Hz), 6.12 (1H, d, J=16.5 Hz), 6.63 (1H, d, J=16.3 Hz).

Reference Example 27

2-{5-methyl-2-[2-trans-(1-methylcyclopentyl)vinyl]oxazol-4-yl}ethyl methanesulfonate IR ν (neat) cm$^{-1}$; 2957, 2872, 1645, 1551, 1533.
$^1$H-NMR (CDCl$_3$) δ (ppm); 1.15 (3H, s), 1.40-1.90 (8H, m), 2.27 (3H, s), 2.86 (2H, t, J=6.6 Hz), 2.94 (3H, s), 4.45 (2H, t, J=6.6 Hz), 6.13 (1H, d, J=16.3 Hz), 6.71 (H, d, J=16.3 Hz).

Reference Example 28

2-[5-methyl-2-(2-methylsulfanylethyl)oxazol-4-yl]ethyl methanesulfonate

IR ν (neat) cm$^{-1}$; 2922, 1651, 1576.
$^1$H-NMR (CDCl$_3$) δ (ppm); 2.12 (3H, s), 2.24 (3H, s), 2.60-3.20 (4H, m), 2.85 (2H, t, J=7.0 Hz), 2.94 (3H, s), 4.43 (2H, t, J=7.0 Hz).

Reference Example 29

2-[2-(3,3-dimethyl-trans-1-buten-1-yl)-5-methyloxazol-4-yl]ethyl methanesulfonate IR ν (neat) cm$^{-1}$; 2962, 2907, 2869, 1660, 1645, 1532.
$^1$H-NMR (CDCl$_3$) δ (ppm); 1.11 (9H, s), 2.27 (3H, s), 2.86 (2H, t, J=6.6 Hz), 2.94 (3H, s), 4.45 (2H, t, J=6.6 Hz), 6.11 (1H, d, J=16.2 Hz), 6.67 (1H, d, J=16.2 Hz).

Reference Example 30

2-[2-(4,4-dimethyl-trans-1-penten-1-yl)-5-methyloxazol-4-yl]ethyl methanesulfonate IR ν (neat) cm$^{-1}$; 2957, 2907, 2868, 1661, 1643, 1533.
$^1$H-NMR (CDCl$_3$) δ (ppm); 0.95 (9H, s), 2.10 (2H, d, J=7.5 Hz), 2.28 (3H, s), 2.87 (2H, t, J=6.6 Hz), 2.94 (3H, s), 4.45 (2H, t, J=6.6 Hz), 6.15 (1H, d, J=16.0 Hz), 6.65 (1H, dt, J=7.5, 16.0 Hz).

Reference Example 31

2-[2-(3-ethyl-trans-1-penten-1-yl)-5-methyloxazol-4-yl]ethyl methanesulfonate

IR ν (neat) cm$^{-1}$; 2963, 2928, 2876, 1643, 1578, 1551, 1533.
$^1$H-NMR (CDCl$_3$) δ (ppm); 0.86 (6H, t, J=6.8 Hz), 1.20-1.70 (4H, m), 1.70-2.20 (1H, m), 2.27 (3H, s), 2.87 (2H, t, J=6.6 Hz), 2.94 (1H, s), 4.45 (2H, t, J=6.6 Hz), 6.12 (1H, d, J=15.8 Hz), 6.41 (1H, dd, J=15.8, 7.9 Hz).

Reference Example 32

2-[2-(3,3-dimethyl-trans-1-penten-1-yl)-5-methyloxazol-4-yl]ethyl methanesulfonate IR ν (neat) cm$^{-1}$; 3034, 3005, 1643, 1545.
$^1$H-NMR (CDCl$_3$) δ (ppm); 0.83 (3H, t, J=7.4 Hz), 1.06 (6H, s), 1.43 (2H, q, J=7.4 Hz), 2.27 (3H, s), 2.87 (2H, t, J=6.7 Hz), 2.94 (1H, s), 4.45 (2H, t, J=6.7 Hz), 6.09 (1H, d, J=16.5 Hz), 6.59 (1H, d, J=16.5 Hz).

Reference Example 33

2-{5-methyl-2-[(trans-2-thiophen-2-yl)vinyl]oxazol-4-yl}ethyl methanesulfonate

IR ν (neat) cm$^{-1}$; 3628, 3420, 3107, 3020, 2924, 1734, 1636, 1547.
$^1$H-NMR (CDCl$_3$) δ (ppm); 2.31 (3H, s), 2.90 (2H, t, J=6,5 Hz) 2.95 (3H, s), 4.78 (2H, t, J=6.5 Hz), 6.64 (1H, d, J=16.1 Hz), 7.02 (1H, dd, J=4.6, 3.2 Hz), 7.16 (1H, d, J=3.2 Hz), 7.29 (1H, d, J=4.6 Hz), 7.52 (1H, d, J=16.1 Hz).

Reference Example 34

2-(5-methyl-2-phenylsulfanyloxazol-4-yl)ethyl methanesulfonate

IR ν (neat) cm$^{-1}$; 2928, 1507.
$^1$H-NMR (CDCl$_3$) δ (ppm); 2.25 (3H, s), 2.86 (2H, t, J=6.5 Hz), 2.90 (3H, s), 4.44 (2H, t, J=6.5 Hz), 7.30-7.75 (5H, m).

Reference Example 35

2-[2-(3-methoxy-trans-1-propen-1-yl)-5-methyloxazol-4-yl]ethyl methanesulfonate

IR ν (neat) cm$^{-1}$; 2930, 1354.
$^1$H-NMR (CDCl$_3$) δ (ppm); 2.28 (3H, s), 2.87 (2H, t, J=6.4 Hz), 2.94 (3H, s), 3.39 (3H, s), 4.45 (2H, t, J=6.5 Hz), 6.30-6.80 (2H, m).

Reference Example 36

2-[2-(5-fluoro-trans-1-penten-1-yl)-5-methyloxazol-4-yl]ethyl methanesulfonate

IR ν (neat) cm$^{31}$ $^1$; 2964, 2928, 2860, 1663, 1643, 1578, 1535.
$^1$H-NMR (CDCl$_3$) δ (ppm); 1.60-2.15 (2H, m), 2.20-2.50 (2H, m), 2.27 (3H, s), 2.86 (2H, t, J=6.6 Hz), 2.94 (3H, s), 4.45 (2H, t, J=6.6 Hz), 4.49 (2H, dt, J=5.8, 47.2 Hz), 6.21 (1H, d, J=16.0 Hz), 6.63 (1H, dt, J=16.0, 6.4 Hz).

Reference Example 37

2-[2-(2-cyclohexylidenemethyl)-5-methyloxazol-4-yl]ethyl methanesulfonate

IR ν (Nujol) cm$^{-1}$; 1651, 1545, 1506.
$^1$H-NMR (CDCl$_3$) δ (ppm); 1.45-1.85 (6H, br), 2.10-2.45 (2H, br), 2.26 (3H, s), 2.65-3.00 (2H, br), 2.86 (2H, t, J=6.6 Hz), 2.93 (3H, s), 4.46 (2H, t, J=6.6 Hz), 5.92 (1H, s).

Reference Example 38

2-[2-(2-cyclopentylidenemethyl)-5-methyloxazol-4-yl]ethyl methanesulfonate

IR ν (neat) cm$^{-1}$; 2957, 2870, 1659, 1645, 1576, 1545, 1526.
$^1$H-NMR (CDCl$_3$) δ (ppm); 1.50-2.00 (4H, m), 2.27 (3H, s), 2.30-3.00 (4H, m), 2.87 (2H, t, J=6.6 Hz), 2.93 (3H, s), 4.46 (2H, t, J=6.6 Hz), 6.10-6.25 (1H, m).

Reference Example 39

2-[2-(5-tert-butylsulfanyl-trans-1-penten-1-yl)-5-methyloxazol-4-yl]ethyl methanesulfonate IR ν (neat) cm$^{-1}$; 2961, 2928, 2862, 1641, 1578, 1535.
$^1$H-NMR (CDCl$_3$) δ (ppm); 1.32 (9H, s), 1.55-1.95 (2H, m), 2.15-2.40 (2H, m), 2.27 (3H, s), 2.57 (2H, t, J=7.0 Hz), 2.86 (2H, t, J=6.6 Hz), 2.94 (3H, s), 4.44 (2H, t, J=6.6 Hz), 6.18 (1H, d, J=16.0 Hz), 6.61 (1H, dt, J=16.0, 6.4 Hz)

Reference Example 40

2-[2-(5-dimethylamino-trans-1-penten-1-yl)-5-methyloxazol-4-yl]ethyl methanesulfonate IR ν (neat) cm$^{-1}$; 2941, 2862, 2818, 2775, 1643, 1533.
$^1$HNNR (CDCl$_3$) δ (ppm); 1.40-1.90 (2H, m), 2.10-2.50 (4H, m) 2.22 (6H, s), 2.27 (3H, s), 2.86 (2H, t, J=6.6 Hz), 2.94 (3H, s), 4.45 (2H, t, J=6.6 Hz), 6.18 (1H, d, J=16.1 Hz), 6.63 (1H, dt, J=16.1, 6.4 Hz).

Reference Example 41

2-[2-(4-methyl-trans-1-penten-1-yl)oxazol-4-yl]ethyl methanesulfonate

IR ν (neat) cm$^{-1}$; 2959, 2930, 2872, 1661, 1597, 1549.
$^1$H-NMR (CDCl$_3$) δ (ppm); 0.95 (6H, d, J=6.4 Hz), 1.50-2.00 (1H, m), 2.14 (2H, t, J=6.8 Hz), 2.96 (3H, s), 2.96 (2H, t, J=6.7 Hz), 4.48 (2H, t, J=6.7 Hz), 6.21 (1H, d, J=16.0 Hz), 6.70 (1H, dt, J=16.0, 7.2 Hz), 7.40 (1H, s).

Experimental Example 1

Using male KK-A$^y$ mice, which were spontaneously diabetic models, which had developed diabetes due to insulin resistance, and which showed high plasma glucose, hypertriglyceridemia and hyperinsulihemia, the pharmacological activity of the test. compounds was examined.

Test Method

Blood was drawn under a non-fasting state from the tail vein of male KK-A$^y$ mice, and the glucose and triglyceride levels of the plasma were measured using commercially available assay kits (glucose CII-test WAKO and triglyceride G-test WAKO, Wako Pure Chemical Industries, Ltd.). The mice were grouped (5 mice per group) into a control group and an administration group, such that the mean and standard deviation of the body weight and the plasma glucose and plasma triglyceride levels in each group were nearly the same. The test compounds (compounds of Examples 1, 2, 4, 8, 20, 22, 24, 27, 30, 33, 36, 37, 40, 45, 47, 52, 56, 58 and 64) were suspended in 5% gum arabic solution and administered (10 mg/kg/day) orally to the administration group for 4 consecutive days. The 5% gumarabic solution was orally administered to the control group. Blood was drawn under a non-fasting state from the tail vein 24 hours after the final administration and the glucose and triglyceride levels of the plasma were measured. The decrease in the plasma glucose and triglyceride levels was calculated from the following formula. The results are shown in Table 1.

Decrease (%)=[(mean of control group−mean of test compound administration group)/mean of control group]×100

Results

TABLE 1

| Test compound | Decrease (%) in glucose level | Decrease (%) in triglyceride level |
|---|---|---|
| Example 1 | 46.1 | 45.3 |
| Example 2 | 40.3 | 40.5 |
| Example 4 | 40.3 | 40.5 |
| Example 8 | 57.2 | 71.1 |
| Example 20 | 57.7 | 65.6 |
| Example 22 | 45.3 | 51.4 |

TABLE 1-continued

| Test compound | Decrease (%) in glucose level | Decrease (%) in triglyceride level |
|---|---|---|
| Example 24 | 52.8 | 50.7 |
| Example 27 | 53.4 | 36.5 |
| Example 30 | 55.4 | 57.0 |
| Example 33 | 58.2 | 68.3 |
| Example 36 | 39.8 | 27.5 |
| Example 37 | 53.2 | 50.1 |
| Example 40 | 54.3 | 37.0 |
| Example 45 | 38.7 | 32.6 |
| Example 47 | 29.9 | 10.9 |
| Example 52 | 26.6 | 19.1 |
| Example 56 | 21.0 | 11.9 |
| Example 58 | 25.1 | 23.2 |
| Example 64 | 29.4 | 25.1 |

Experimental Example 2

Using db/db mice genetically showing high plasma glucose, hypertriglyceridemia, insulin resistance and obesity, the pharmacological activity of the test compounds of Examples 1, 2 and 20 was examined.

Test Method

Blood was drawn under a non-fasting state from the tail vein of male db/db mice, the glucose level and triglyceride level of the plasma were measured using commercially available assay kits (glucose CII-test WAKO and triglyceride G-test WAKO, Wako Pure Chemical Industries, Ltd.). The mice were grouped (6 mice per group) into a control group and test compound (compounds of Examples 1, 2 and 20) administration group (3 mg/kg/day), such that the mean and standard deviation of the body weight and the plasma glucose and plasma triglyceride levels in each group were nearly the same. The test compound was suspended in 0.5% methylcellulose solution and administered orally for 2 consecutive weeks from the next day. The 0.5% methylcellulose solution was orally administered to the control group. Blood was drawn under a non-fasting state from the tail vein 24 hours after the final administration and the glucose and triglyceride levels of the plasma were measured. The decrease in the plasma glucose and triglyceride levels was calculated from the following formula. The results are shown in Table 2.

Decrease (%)=[(mean of control group−mean of test compound administration group)/mean of control group]×100

Results

TABLE 2

| Test compound | Decrease (%) in glucose level | Decrease (%) in triglyceride level |
|---|---|---|
| Example 1 | 21.3 | 62.7 |
| Example 2 | 57.2 | 78.1 |
| Example 20 | 54.0 | 72.0 |

Experimental Example 3

Using 7-week-old male ICR mice, toxicity by repeat administration was examined.

Test Method

The mice were grouped (7 mice per group) into a control group and test compound (compounds of Examples 2 and 20) administration groups (30 and 100 mg/kg/day), such that the mean and the standard deviation of the body weight of the mice were nearly the same. The test compound was suspended in 0.5% methylcellulose solution and administered orally for 2 consecutive weeks from the next day. The 0.5% methylcellulose solution was orally administered to the control group. At 24 hours after the final administration, Evans blue (100 μg/mouse) was administered from the tail vein and, 5 min later, the blood was drawn from the orbital venous plexus with anesthesia. Using EDTA-added blood, hematocrit value and erythrocyte count were measured. Using the plasma, Evans blue concentration was measured, from which plasma volume was calculated. The liver and heart were removed and wet weight was measured.

Results

There was found no significant difference in the body weight, hematocrit value, erythrocyte count, plasma volume, weight of the liver and the heart of the test compound (compounds of Examples 2 and 20) administration (30 and 100 mg/kg/day) groups from those of the control group.

Experimental Example 4

Using 6-week-old female Wistar rats, toxicity by repeat administration was examined.

Test Method

The rats were grouped (6 rats per group) into a control group and test compound (compounds of Examples 2 and 20) administration groups (30 and 100 mg/kg/day), such that the mean and the standard deviation of the body weight of the rats were nearly the same. The test compound was suspended in 0.5% methylcellulose solution and administered orally for 2 consecutive weeks from the next day. The 0.5% methylcellulose solution was orally administered to the control group. The rats were fasted for 16 hr from the last day of administration, anesthetized by intraperitoneal administration of pentobarbital sodium (50 mg/kg) 24 hr after the final administration and the blood was drawn. Using EDTA-added blood, hematocrit value and erythrocyte count were measured, and using serum, AST (GOT) and ALT (GPT) were measured. In addition, the white fat around the uterus, and the liver and heart were removed and the wet weights thereof were measured.

Results

There was found no significant difference in the hematocrit value, erythrocyte count, weight of the white fat around the uterus, and the liver and heart, and AST (GOT) and ALT (GPT) of the test compound (compounds of Examples 2 and 20) administration (30 and 100 mg/kg/day) groups from those of the control group.

Experimental Example 5

The superior water-solubility of the compound of the present invention was confirmed by determining the solubility of the compound in water.

Test Method

The pulverized test compound (compounds of Examples 2, 20, 22, 24, 27, 30, 40 or 65, 25 mg) was added to a buffer (1.0 ml, pH 7.0) and the mixture was shaken at 25° C. for 1 hr and passed through a membrane filter. The concentration of the test compound in the filtrate was measured by high performance liquid chromatography. The results are shown in Table 3.

Results

TABLE 3

| Test compound | Solubility (mg/ml) |
|---|---|
| Example 2 | 10.0 |
| Example 20 | 25 or above |
| Example 22 | 25 or above |
| Example 24 | 18.7 |
| Example 27 | 25 or above |
| Example 30 | 17.3 |
| Example 40 | 18.7 |
| Example 65 | 20.5 |

INDUSTRIAL APPLICABILITY

The novel heterocyclic compound having the above-mentioned formula (I) of the present invention and a pharmaceutically acceptable salt thereof have a hypoglycemic action, a blood hypolipidemic action, an insulin resistance improving action and a PPAR activating action, and are useful as a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases or an agent for the prophylaxis or treatment of syndrome X.

This application is based on patent application No. 2001-161489 filed in Japan, the contents of which are hereby incorporated by reference.

What is claimed is:

1. A novel heterocyclic compound of the formula (I):

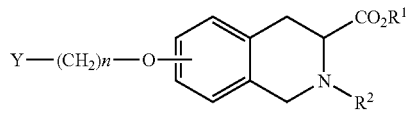

wherein
R$^1$ is a hydrogen atom or C$_{1-6}$ alkyl;
R$^2$ is a hydrogen atom, —CO—R$^3$ wherein R$^3$ is C$_{2-6}$ alkyl optionally substituted by halogen, —CO—C(R$^4$)═C (R$^4$)—R$^5$ wherein R$^4$ is optionally the same as the other R$^4$ and is a hydrogen atom or C$_{1-4}$ alkyl and R$^5$ is C$_{1-8}$ alkyl, C$_{2-8}$ alkenyl, aryl or an aromatic heterocycle, —CO—C≡C—R$^6$ wherein R$^6$ is C$_{1-8}$ alkyl,

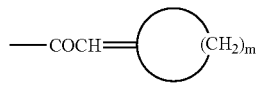

wherein m is an integer of 2 to 7, aryl, optionally substituted aryl C$_{1-3}$ alkyl, C$_{1-6}$ alkyl optionally substituted by halogen, C$_{2-6}$ alkenyl, C$_{3-8}$ cycloalkyl or C$_{3-8}$ cycloalkyl C$_{1-3}$ alkyl;

Y is

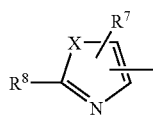

wherein R$^7$ is a hydrogen atom or C$_{1-4}$ alkyl,
R$^8$ is C$_{5-8}$ alkyl, C$_{4-8}$ cycloalkyl, C$_{1-4}$ alkylthio C$_{1-6}$ alkyl, R$^{10}$—C(R$^9$)═C(R$^9$)— wherein R$^9$ is optionally the same as the other R$^9$ and is a hydrogen atom or C$_{1-4}$ alkyl and R$^{10}$ is C$_{1-6}$ alkyl optionally substituted by halogen, C$_{2-8}$ alkenyl, aryl, an aromatic heterocycle, C$_{3-8}$ cycloalkyl, C$_{3-8}$ cycloalkyl C$_{1-3}$ alkyl, C$_{1-4}$ alkoxy C$_{1-6}$ alkyl, C$_{1-4}$ alkylthio C$_{1-6}$ alkyl or C$_{1-6}$ alkyl substituted by (R$^9$)$_2$N— wherein R$^9$ is optionally the same as the other R$^9$ and is a hydrogen atom or C$_{1-4}$ alkyl,
R$^{12}$—CO—N(R$^{11}$)— wherein R$^{11}$ is a hydrogen atom or C$_{1-4}$ alkyl and R$^{12}$ is C$_{1-6}$ alkyl or aryl, R$^{13}$-Z- wherein R$^{13}$ is C$_{1-8}$ alkyl or aryl and Z is an oxygen atom or a sulfur atom, or

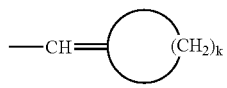

wherein k is an integer of 2 to 7 and
X is an oxygen atom or a sulfur atom,
or R$^{15}$—C(R$^{14}$)═N—O— wherein R$^{14}$ is a hydrogen atom or C$_{1-4}$ alkyl and R$^{15}$ is aryl or an aromatic heterocycle;
Y—(CH$_2$)$_n$—O— is bonded to the 6- or 7-position of a tetrahydroisoquinoline skeleton; and
n is an integer of 1 to 4
or a pharmaceutically acceptable salt thereof.

2. The novel heterocyclic compound of claim 1, wherein, in the formula (I), R$^2$ is an optionally substituted aryl C$_{1-3}$ alkyl, C$_{1-6}$ alkyl optionally substituted by halogen, C$_{2-6}$ alkenyl, C$_{3-8}$ cycloalkyl, C$_{3-8}$ cycloalkyl C$_{1-3}$ alkyl or

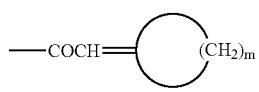

wherein m is an integer of 2 to 7,
or a pharmaceutically acceptable salt thereof.

3. The novel heterocyclic compound of claim 1, wherein, in the formula (I), Y is

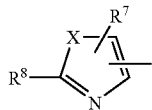

wherein $R^7$ is a hydrogen atom or $C_{1-4}$ alkyl,
$R^8$ is $C_{1-4}$ alkylthio $C_{1-6}$ alkyl, $R^{10}$—C($R^9$)=C($R^9$)— wherein $R^9$ is optionally the same as the other $R^9$ and is a hydrogen atom or $C_{1-4}$ alkyl and $R^{10}$ is $C_{1-6}$ alkyl optionally substituted by halogen, $C_{3-8}$ cycloalkyl, $C_{3-8}$ cycloalkyl $C_{1-3}$ alkyl, $C_{1-4}$ alkoxy $C_{1-6}$ alkyl, $C_{1-4}$ alkylthio $C_{1-6}$ alkyl, or $C_{1-6}$ alkyl substituted by $(R^9)_2N$— wherein $R^9$ is optionally the same as the other $R^9$ and is a hydrogen atom or $C_{1-4}$ alkyl, or

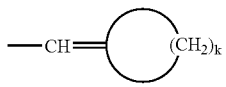

wherein k is an integer of 2 to 7, and
X is an oxygen atom or a sulfur atom,
or a pharmaceutically acceptable salt thereof.

4. The novel heterocyclic compound of claim 1, wherein, in the formula (I),
$R^2$ is a hydrogen atom, —CO—$R^3$ wherein $R^3$ is $C_{2-6}$ alkyl optionally substituted by halogen, —COC($R^4$)=C($R^4$)—$R^5$ wherein $R^4$ is optionally the same as the other $R^4$ and is a hydrogen atom or $C_{1-4}$ alkyl and $R^5$ is $C_{1-8}$ alkyl, $C_{2-8}$ alkenyl, aryl or aromatic heterocycle, —CO—C≡C—$R^6$ wherein $R^6$ is $C_{1-8}$ alkyl, or aryl, and Y is

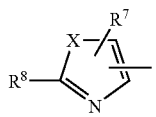

wherein $R^7$ is a hydrogen atom or $C_{1-4}$ alkyl,
$R^8$ is $C_{5-8}$ alkyl, $C_{4-8}$ cycloalkyl, $R^{10}$—C($R^9$)=C($R^9$)— wherein $R^9$ is optionally the same as the other
$R^9$ and is a hydrogen atom or $C_{1-4}$ alkyl and $R^{10}$ is $C_{1-6}$ alkyl, $C_{2-8}$ alkenyl, aryl or an aromatic heterocycle, $R^{12}$—CO—N($R^{11}$)— wherein $R^{11}$ is a hydrogen atom or $C_{1-4}$ alkyl and $R^{12}$ is $C_{1-6}$ alkyl or aryl, or $R^{13}$-Z- wherein $R^{13}$ is $C_{1-8}$ alkyl or aryl and Z is an oxygen atom or a sulfur atom, and
X is an oxygen atom or a sulfur atom, or
$R^{15}$—C($R^{14}$)=N—O— wherein $R^{14}$ is a hydrogen atom or $C_{1-4}$ alkyl and $R^{15}$ is aryl or an aromatic heterocycle,
or a pharmaceutically acceptable salt thereof.

5. The novel heterocyclic compound of claim 2 or 3, wherein, in the formula (I), Y—(CH$_2$)n—O— is bonded to the 7-position of a tetrahydroisoquinoline skeleton and n is 2, or a pharmaceutically acceptable salt thereof.

6. The novel heterocyclic compound of claim 4, wherein, in the formula (I), Y—(CH$_2$)n—O— is bonded to the 7-position of a tetrahydroisoquinoline skeleton and n is 2, or a pharmaceutically acceptable salt thereof.

7. The novel heterocyclic compound of claim 6, wherein, in the formula (I), Y is

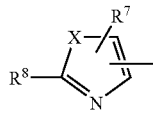

wherein $R^7$ is a hydrogen atom or $C_{1-4}$ alkyl, and
$R^8$ is $R^{10}$—C($R^9$)=C($R^9$)— wherein $R^9$ is optionally the same as the other $R^9$ and is a hydrogen atom or $C_{14}$ alkyl and $R^{10}$ is $C_{1-6}$ alkyl, $C_{2-8}$ alkenyl or aryl,
or a pharmaceutically acceptable salt thereof.

8. The novel heterocyclic compound of claim 6, wherein, in the formula (I), Y is

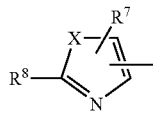

wherein $R^7$ is a hydrogen atom or $C_{1-4}$ alkyl, and
$R^8$ is $R^{13}$-Z- wherein $R^{13}$ is $C_{1-8}$ alkyl or aryl and Z is a sulfur atom,
or a pharmaceutically acceptable salt thereof.

9. The novel heterocyclic compound of claim 6, wherein, in the formula (I), Y is

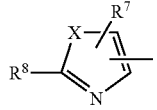

wherein $R^7$ is a hydrogen atom or $C_{1-4}$ alkyl, and
$R^8$ is $C_{5-8}$ alkyl or $C_{4-8}$ cycloalkyl,
or a pharmaceutically acceptable salt thereof.

10. The novel heterocyclic compound of claim 5, wherein, in the formula (I), Y is

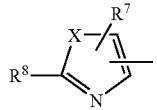

wherein $R^7$ is a hydrogen atom or $C_{1-4}$ alkyl, and
$R^8$ is $R^{10}$—C($R^9$)=C($R^9$)— wherein $R^9$ is optionally the same as the other $R^9$ and is a hydrogen atom or $C_{1-4}$ alkyl and $R^{10}$ is $C_{3-8}$ cycloalkyl,
or a pharmaceutically acceptable salt thereof.

11. The novel heterocyclic compound of any one of claims 7 to 9, wherein, in the formula (I), $R^2$ is —CO—C($R^4$)=C($R^4$)—$R^5$ wherein $R^4$ is a hydrogen atom and $R^5$ is $C_{1-8}$ alkyl or $C_{2-8}$ alkenyl,
or a pharmaceutically acceptable salt thereof.

12. The novel heterocyclic compound of any one of claims 7 to 9, wherein, in the formula (I), $R^2$ is —CO—C≡C—$R^6$ wherein $R^6$ is $C_{1-8}$ alkyl,
or a pharmaceutically acceptable salt thereof.

13. The novel heterocyclic compound of claim 6, wherein, in the formula (I), Y is

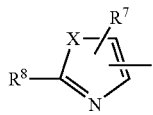

wherein $R^7$ is $C_{1-4}$ alkyl, $R^8$ is $R^{10}$—C($R^9$)=C($R^9$)— wherein $R^9$ is optionally the same as the other $R^9$ and is a hydrogen atom or $C_{1-4}$ alkyl and $R^{10}$ is $C_{1-6}$ alkyl, and X is an oxygen atom, or a pharmaceutically acceptable salt thereof.

14. The novel heterocyclic compound of claim 6, wherein, in the formula (I), Y is

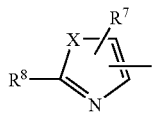

wherein $R^7$ is $C_{1-4}$ alkyl, $R^8$ is $R^{10}$—C($R^9$)=C($R^9$)— wherein $R^9$ is a hydrogen atom and $R^{10}$ is aryl, and X is an oxygen atom, or a pharmaceutically acceptable salt thereof.

15. The novel heterocyclic compound of claim 4, wherein, in the formula (I), Y is selected from the following (a) to (n):

(a)
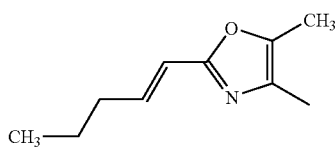

(b)
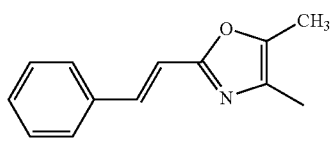

(c)
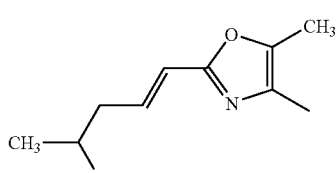

(d)
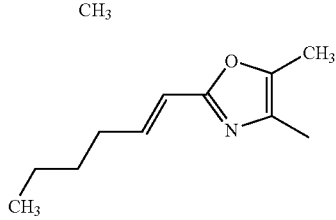

-continued (e)
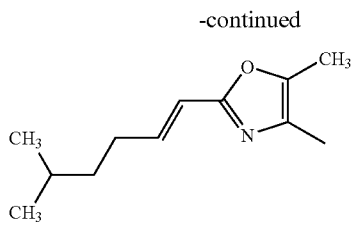

(f)
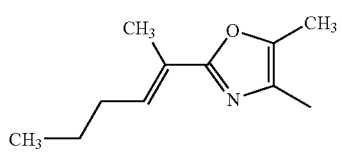

(g)
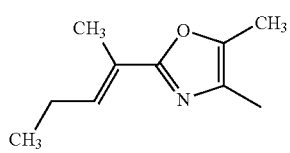

(h)
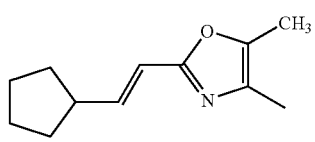

(i)
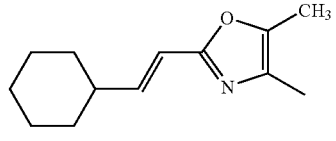

(j)
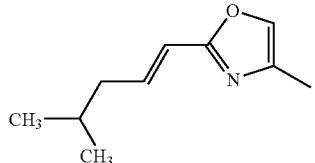

(k)
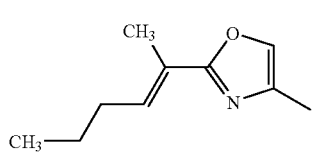

(l)
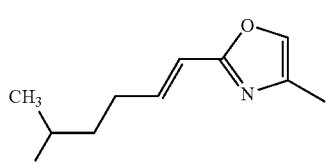

(m)
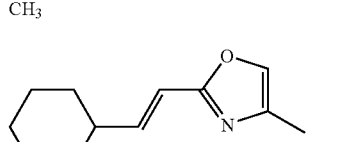

and (n)
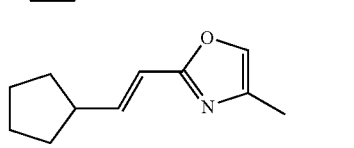

or a pharmaceutically acceptable salt thereof.

16. The novel heterocyclic compound of claim 1, wherein the compound of the formula (I) is any of the following (1) to (16):

(1) 2-(2,4-hexadienoyl)-7-[2-(5-methyl-2-styryloxazol-4-yl)ethoxy]-1,2,3,4-tetrahydroisoquinoline-(3S)-carboxylic acid,
(2) 2-(2-heptenoyl)-7-[2-(5-methyl-2-styryloxazol-4-yl)ethoxy]-1,2,3,4-tetrahydroisoquinoline-(3S)-carboxylic acid,
(3) 2-(2-hexynoyl)-7-[2-(5-methyl-2-styryloxazol-4-yl)ethoxy]-1,2,3,4-tetrahydroisoquinoline-(3S)-carboxylic acid,
(4) 7-[2-(5-methyl-2-styryloxazol-4-yl)ethoxy]-2-pentafluoropropionyl-1,2,3,4-tetrahydroisoquinoline-(3S)-carboxylic acid,
(5) 2-(2-heptenoyl)-7-[2-(5-methyl-2-styrylthiazol-4-yl)ethoxy]-1,2,3,4-tetrahydroisoquinoline-(3S)-carboxylic acid,
(6) 2-(2,4-hexadienoyl)-7-[2-(5-methyl-2-(1-penten-1-yl)oxazol-4-yl)ethoxy]-1,2,3,4-tetrahydroisoquinoline-(3S)-carboxylic acid,
(7) 2-(2-heptenoyl)-7-[2-(5-methyl-2-(1-penten-1-yl)oxazol-4-yl)ethoxy]-1,2,3,4-tetrahydroisoquinoline-(3S)-carboxylic acid,
(8) 2-(2-hexynoyl)-7-[2-(5-methyl-2-(1-penten-1-yl)oxazol-4-yl)ethoxy]-1,2,3,4-tetrahydroisoquinoline-(3S)-carboxylic acid,
(9) 2-(2,4-hexadienoyl)-7-[2-(5-methyl-2-(1,3-pentadien-1-yl)oxazol-4-yl)ethoxy]-1,2,3,4-tetrahydroisoquinoline-(3S)-carboxylic acid,
(10) 2-(2,4-hexadienoyl)-7-[2-(5-methyl-2-pentyloxazol-4-yl)ethoxy]-1,2,3,4-tetrahydroisoquinoline-(3S)-carboxylic acid,
(11) 7-[2-(2-cyclopentyl-5-methyloxazol-4-yl)ethoxy]-2-(2,4-hexadienoyl)-1,2,3,4-tetrahydroisoquinoline-(3S)-carboxylic acid,
(12) 7-[2-(2-cyclohexyl-5-methyloxazol-4-yl)ethoxy]-2-(2,4-hexadienoyl)-1,2,3,4-tetrahydroisoquinoline-(3S)-carboxylic acid,
(13) 7-[2-(2-benzoylaminothiazol-5-yl)ethoxy]-2-(2-heptenoyl)-1,2,3,4-tetrahydroisoquinoline-(3S)-carboxylic acid,
(14) 7-[2-(2-butyrylaminothiazol-5-yl)ethoxy]-2-(2-heptenoyl)-1,2,3,4-tetrahydroisoquinoline-(3S)-carboxylic acid,
(15) 2-(2-heptenoyl)-7-[2-(4-methyl-2-phenylsulfanylthiazol-5-yl)ethoxy]-1,2,3,4-tetrahydroisoquinoline-(3S)-carboxylic acid, and
(16) 2-(2-heptenoyl)-7-[2-(1-phenylethylideneaminoxy)ethoxy]-1,2,3,4-tetrahydroisoquinoline-(3S)-carboxylic acid, or a pharmaceutically acceptable salt thereof.

17. The novel heterocyclic compound of claim 1, wherein the compound of the formula (I) is any of the following (1) to (3):

(1) 7-[2-(5-methyl-2-styryloxazol-4-yl)ethoxy]-2-pentafluoropropionyl-1,2,3,4-tetrahydroisoquinoline-(3S)-carboxylic acid,
(2) 2-(2-heptenoyl)-7-[2-(5-methyl-2-(trans-1-penten-1-yl)oxazol-4-yl)ethoxy]-1,2,3,4-tetrahydroisoquinoline-(3S)-carboxylic acid, and
(3) 2-(2-hexynoyl)-7-[2-(5-methyl-2-(trans-1-penten-1-yl)oxazol-4-yl)ethoxy]-1,2,3,4-tetrahydroisoquinoline-(3S)-carboxylic acid, or a pharmaceutically acceptable salt thereof.

18. The novel heterocyclic compound of claim 1, wherein the compound of the formula (I) is any of the following (1) to (17):

(1) 2-(2,4-hexadienoyl)-7-{2-[5-methyl-2-(4-methyl-1-penten-1-yl)oxazol-4-yl]ethoxy}-1,2,3,4-tetrahydroisoquinoline-(3S)-carboxylic acid,
(2) 2-(2-heptenoyl)-7-{2-[5-methyl-2-(4-methyl-1-penten-1-yl)oxazol-4-yl]ethoxy}-1,2,3,4-tetrahydroisoquinoline-(3S)-carboxylic acid,
(3) 2-(2,4-hexadienoyl)-7-{2-[2-(1-hexen-1-yl)-5-methyloxazol-4-yl]ethoxy}-1,2,3,4-tetrahydroisoquinoline-(3S)-carboxylic acid,
(4) 2-(2,4-hexadienoyl)-7-{2-[5-methyl-2-(5-methyl-1-hexen-1-yl)oxazol-4-yl]ethoxy}-1,2,3,4-tetrahydroisoquinoline-(3S)-carboxylic acid,
(5) 2-(2,4-hexadienoyl)-7-{2-[5-methyl-2-(1-methyl-1-penten-1-yl)oxazol-4-yl]ethoxy}-1,2,3,4-tetrahydroisoquinoline-(3S)-carboxylic acid,
(6) 2-(2,4-hexadienoyl)-7-{2-[5-methyl-2-(1-methyl-1-buten-1-yl)oxazol-4-yl]ethoxy}-1,2,3,4-tetrahydroisoquinoline-(3S)-carboxylic acid,
(7) 2-(2-hexenoyl)-7-{2-[5-methyl-2-(4-methyl-1-penten-1-yl)oxazol-4-yl]ethoxy}-1,2,3,4-tetrahydroisoquinoline-(3S)-carboxylic acid,
(8) 7-{2-[5-methyl-2-(1-penten-1-yl)oxazol-4-yl]ethoxy}-2-(2,2,3,3,3-pentafluoropropionyl)-1,2,3,4-tetrahydroisoquinoline-(3S)-carboxylic acid,
(9) 7-{2-[2-(4,4-dimethyl-1-penten-1-yl)-5-methyloxazol-4-yl]ethoxy}-2-(2,4-hexadienoyl)-1,2,3,4-tetrahydroisoquinoline-(3S)-carboxylic acid,
(10) 2-(2,4-hexadienoyl)-7-{2-[5-methyl-2-(3-methyl-1-buten-1-yl)oxazol-4-yl]ethoxy}-1,2,3,4-tetrahydroisoquinoline-(3S)-carboxylic acid,
(11) 2-(2,4-hexadienoyl)-7-(2-{5-methyl-2-[2-(1-methylcyclohexan-1-yl)vinyl]oxazol-4-yl}ethoxy)-1,2,3,4-tetrahydroisoquinoline-(3S)-carboxylic acid,
(12) 7-{2-[2-(3,3-dimethyl-1-buten-1-yl)-5-methyloxazol-4-yl]ethoxy}-2-(2,4-hexadienoyl)-1,2,3,4-tetrahydroisoquinoline-(3S)-carboxylic acid,
(13) 2-(2,4-hexadienoyl)-7-{2-[2-(3-methoxy-1-propen-1-yl)-5-methyloxazol-4-yl]ethoxy}-1,2,3,4-tetrahydroisoquinoline-(3S)-carboxylic acid,
(14) 7-{2-[2-(2-cyclopentylvinyl)-5-methyloxazol-4-yl]ethoxy}-2-(2,4-hexadienoyl)-1,2,3,4-tetrahydroisoquinoline-(3S)-carboxylic acid,
(15) 7-{2-[2-(2-cyclohexylvinyl)-5-methyloxazol-4-yl]ethoxy}-2-(2,4-hexadienoyl)-1,2,3,4-tetrahydroisoquinoline-(3S)-carboxylic acid,
(16) 2-(3-butenyl)-7-{2-[5-methyl-2-(4-methyl-1-penten-1-yl)oxazol-4-yl]ethoxy}-1,2,3,4-tetrahydroisoquinoline-(3S)-carboxylic acid, and
(17) 7-{2-[5-methyl-2-(4-methyl-1-penten-1-yl)oxazol-4-yl]ethoxy}-2-(4-pentenyl)-1,2,3,4-tetrahydroisoquinoline-(3S)-carboxylic acid, or a pharmaceutically acceptable salt thereof.

19. The novel heterocyclic compound of claim 1, wherein the compound of the formula (I) is any of the following (1) to (8):

(1) 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic acid,
(2) 2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic acid,
(3) 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, (4) 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylic acid,
(5) 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid,
(6) 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylic acid,
(7) 2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylic acid, and
(8) 2-(2-hexenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid,
or a pharmaceutically acceptable salt thereof.

20. The novel heterocyclic compound of claim 1, wherein the compound of the formula (I) is any of the following (1) to (6):
(1) 7-{2-[5-methyl-2-(trans-1-penten-1-yl)oxazol-4-yl]ethoxy}-2-(2,2,3,3,3-pentafluoropropionyl)-1,2,3,4-tetrahydroisoquinoline-(3S)-carboxylic acid,
(2) 7-{2-[2-(4,4-dimethyl-trans-1-penten-1-yl)-5-methyloxazol-4-yl]ethoxy}-2-(2,4-hexadienoyl)-1,2,3,4-tetrahydroisoquinoline-(3S)-carboxylic acid,
(3) 2-(2,4-hexadienoyl)-7-{2-[5-methyl-2-(3-methyl-trans-1-buten-1-yl)oxazol-4-yl]ethoxy}-1,2,3,4-tetrahydroisoquinoline-(3S)-carboxylic acid,
(4) 2-(2,4-hexadienoyl)-7-(2-{5-methyl-2-[2-trans-(1-methylcyclohexan-1-yl)vinyl]oxazol-4-yl}ethoxy)-1,2,3,4-tetrahydroisoquinoline-(3S)-carboxylic acid,
(5) 7-{2-[2-(3,3-dimethyl-trans-1-buten-1-yl)-5-methyloxazol-4-yl]ethoxy}-2-(2,4-hexadienoyl)-1,2,3,4-tetrahydroisoquinoline-(3S)-carboxylic acid, and
(6) 2-(2,4-hexadienoyl)-7-{2-[2-(3-methoxy-trans-1-propen-1-yl)-5-methyloxazol-4-yl]ethoxy}-1,2,3,4-tetrahydroisoquinoline-(3S)-carboxylic acid,
or a pharmaceutically acceptable salt thereof.

21. The novel heterocyclic compound of claim 1, wherein the compound of the formula (I) is the following (1) or (2):
(1) 7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylic acid,
(2) 7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylic acid,
or a pharmaceutically acceptable salt thereof.

22. The novel heterocyclic compound of claim 1, wherein the compound of the formula (I) is the following (1) or (2):
(1) 2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic acid,
(2) 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid,
or a pharmaceutically acceptable salt thereof.

23. The novel heterocyclic compound of claim 1, wherein the compound of the formula (I) is any of the following (1) to (9):
(1) 2-(2,4-hexadienoyl)-7-{2-[2-(4-methyl-trans-1-penten-1-yl)oxazol-4-yl]ethoxy}-1,2,3,4-tetrahydroisoquinoline-(3S)-carboxylic acid,
(2) 7-{2-[2-(trans-2-cyclopentylvinyl)oxazol-4-yl]ethoxy}-2-(2,4-hexadienoyl)-1,2,3,4-tetrahydroisoquinoline-(3S)-carboxylic acid,
(3) 7-{2-[2-(trans-2-cyclohexylvinyl)oxazol-4-yl]ethoxy}-2-(2,4-hexadienoyl)-1,2,3,4-tetrahydroisoquinoline-(3S)-carboxylic acid,
(4) 2-(2-heptenoyl)-7-{2-[2-(4-methyl-trans-1-penten-1-yl)oxazol-4-yl]ethoxy}-1,2,3,4-tetrahydroisoquinoline-(3S)-carboxylic acid,
(5) 2-(2-hexenoyl)-7-{2-[2-(4-methyl-trans-penten-1-yl)oxazol-4-yl]ethoxy}-1,2,3,4-tetrahydroisoquinoline-(3S)-carboxylic acid,
(6) 2-(2,4-hexadienoyl)-7-{2-[2-(trans-1-hexen-1-yl)oxazol-4-yl]ethoxy}-1,2,3,4-tetrahydroisoquinoline-(3S)-carboxylic acid,
(7) 2-(2,4-hexadienoyl)-7-{2-[2-(1-methyl-trans-1-penten-1-yl)oxazol-4-yl]ethoxy}-1,2,3,4-tetrahydroisoquinoline-(3S)-carboxylic acid,
(8) 2-(2,4-hexadienoyl)-7-{2-[2-(1-methyl-trans-1-buten-1-yl)oxazol-4-yl]ethoxy}-1,2,3,4-tetrahydroisoquinoline-(3S)-carboxylic acid, and
(9) 2-(2,4-hexadienoyl)-7-{2-[(5-methyl-trans-1-hexen-1-yl)oxazol-4-yl]ethoxy}-1,2,3,4-tetrahydroisoquinoline-(3S)-carboxylic acid,
or a pharmaceutically acceptable salt thereof.

24. A pharmaceutical composition containing the novel heterocyclic compound of claim 1, or a pharmaceutically acceptable salt thereof together with a pharmaceutically acceptable additive.

25. A pharmaceutical composition comprising the novel heterocyclic compound of claim 1, or a pharmaceutically acceptable salt thereof, together with an agent selected from the group consisting of a hypoglycemic agent, a hypolipidemic agent, an insulin resistance improver, a therapeutic agent of diabetes, a therapeutic agent of diabetic complications, a glucose tolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.

26. A method for treatment of diabetes, diabetic complication, hyperglycemia, diseases caused by insulin resistance glucose intolerance, or diseases caused by insulin resistance, which comprises administering a pharmaceutically effective amount of the heterocyclic compound of claim 1 or a pharmaceutically acceptable salt thereof to a patient in need thereof.

27. A method for producing a pharmaceutical composition for treatment of diabetes, diabetic complication, hyperlipidemia, arteriosclerosis, hyperglycemia, glucose intolerance, diseases caused by insulin resistance, obesity, inflammation, PPAR-mediated disease or syndrome X, which comprises mixing the novel heterocyclic compound of claim 1 or a pharmaceutically acceptable salt thereof together with a pharmaceutically acceptable additive.

* * * * *